(12) United States Patent
Scheffler et al.

(10) Patent No.: US 11,740,201 B2
(45) Date of Patent: *Aug. 29, 2023

(54) SENSOR INTERROGATION

(71) Applicant: MSA TECHNOLOGY, LLC, Cranberry Township, PA (US)

(72) Inventors: Towner Bennett Scheffler, Lansdale, PA (US); Michael Alvin Brown, Cranberry Township, PA (US); Brian Keith Davis, Butler, PA (US)

(73) Assignee: MSA Technology, LLC, Cranberry Township, PA (US)

( * ) Notice: Subject to any disclaimer, the term of this patent is extended or adjusted under 35 U.S.C. 154(b) by 307 days.

This patent is subject to a terminal disclaimer.

(21) Appl. No.: 17/163,710

(22) Filed: Feb. 1, 2021

(65) Prior Publication Data
US 2021/0148849 A1 May 20, 2021

Related U.S. Application Data

(63) Continuation of application No. 13/796,652, filed on Mar. 12, 2013, now Pat. No. 10,908,111, which is a
(Continued)

(51) Int. Cl.
*G01N 27/404* (2006.01)
*G01N 27/26* (2006.01)
(Continued)

(52) U.S. Cl.
CPC ......... *G01N 27/26* (2013.01); *G01N 27/4175* (2013.01); *G01N 33/007* (2013.01); *G01N 33/497* (2013.01); *Y10T 29/49826* (2015.01)

(58) Field of Classification Search
CPC .. G01N 27/26; G01N 27/4175; G01N 33/007; G01N 33/497
See application file for complete search history.

(56) References Cited

U.S. PATENT DOCUMENTS 4,555,930 A 12/1985 Leach
5,064,516 A 11/1991 Rupich
(Continued)

FOREIGN PATENT DOCUMENTS

GB 2356708 5/2001
WO WO2004011924 A1 2/2004
(Continued)

OTHER PUBLICATIONS

A.J. Bard and L. R. Faulkner, Electrochemical Methods: Fundamentals and Applications, John Wiley & Sons: New York (1980), pp. 553-576.
(Continued)

*Primary Examiner* — Alexander S Noguerola
(74) *Attorney, Agent, or Firm* — BARTONY & ASSOCIATES LLC

(57) ABSTRACT

A system includes a system housing including an inlet, at least one gas sensor responsive to a first analyte gas other than oxygen within the system housing and in fluid connection with the inlet, and a sensor responsive to oxygen within the system housing and in fluid connection with the inlet. The sensor responsive to oxygen is formed to be chemically separate from the at least one gas sensor responsive to the first analyte gas other than oxygen. The sensor responsive to oxygen is responsive to a change in the concentration of oxygen arising from creation of a driving force in the vicinity of the inlet to provide an indication of a state of a transport path between the inlet of the system and the at least one gas sensor responsive to the first analyte gas other than oxygen.

8 Claims, 34 Drawing Sheets

Related U.S. Application Data continuation-in-part of application No. 13/650,613, filed on Oct. 12, 2012, now Pat. No. 9,410,940.

(60) Provisional application No. 61/698,153, filed on Sep. 7, 2012, provisional application No. 61/547,245, filed on Oct. 14, 2011.

(51) Int. Cl.
  *G01N 33/00* (2006.01)
  *G01N 33/497* (2006.01)
  *G01N 27/417* (2006.01)

(56) References Cited

U.S. PATENT DOCUMENTS

| | | | |
|---|---|---|---|
| 5,298,146 | A | 3/1994 | Braden |
| 5,667,653 | A | 9/1997 | Schneider |
| 5,932,079 | A | 8/1999 | Haupt |
| 5,944,969 | A | 8/1999 | Scheffler |
| 6,092,992 | A | 7/2000 | Imblum |
| 6,177,001 | B1 | 1/2001 | Meyer |
| 6,428,684 | B1 | 8/2002 | Warburton |
| 6,896,781 | B1 | 5/2005 | Shen |
| 7,413,645 | B2 | 8/2008 | Scheffler |
| 10,908,111 | B2 * | 2/2021 | Scheffler .............. G01N 33/007 |
| 2001/0045119 | A1 | 11/2001 | Warburton |
| 2002/0036137 | A1 | 3/2002 | Slater |
| 2006/0042353 | A1 | 3/2006 | Marquis |
| 2008/0134752 | A1 | 6/2008 | Krellner |
| 2008/0302673 | A1 | 12/2008 | Scheffler |
| 2010/0252455 | A1 | 10/2010 | Pratt |
| 2011/0100090 | A1 | 5/2011 | Zanella, Sr. |
| 2011/0100813 | A1 | 5/2011 | Davis |

FOREIGN PATENT DOCUMENTS

| | | |
|---|---|---|
| WO | WO20050114162 | 12/2005 |
| WO | WO2008094118 A1 | 8/2008 |
| WO | WO20140143175 | 9/2014 |

OTHER PUBLICATIONS

Drager Sensor, 23560 Lubeck, Germany, Feb. 1, 2007, pp. 2-4, Retrieved from the Internet on Jan. 16, 2013: URL: http://www.draeger.com/media/10/02/45/10024547/draegersensor_xs_ec_co2_ds_9023376 _de_en.pdf.

MGD—Murco Gas Detector—Check I Calibration Procedure, Dublin, Ireland, Jan. 1, 2010, pp. 1-6, Retrieved from the Internet on Jan. 16, 2013: URL:http://www.murcogasdetection.com/assets/pdfs/calibration/MGD-Check-Callibration-Manual-web-2010.pdf.

ST-IAM—Sensor Transmitter Integrated Area Monitor—Check I Calibration Procedure, Dublin, Ireland, Jan. 1, 2010, pp. 1-6, Retrieved from the Internet on Jan. 16, 2013: URL:http://www.murcogasdetection.com/assets/pdfs/calibration/STIAM-Check-Callibration-Manual-web-2010.pdf.

Mosely, P.T. and Tofield, B.C., ed., Solid State Gas Sensors, Adams Hilger Press, Bristol, England, 17-31, (1987).

Firth, J.G. et al., The Principles of the Detection of Flammable Atmospheres by Catalytic Devices, Combustion and Flame, 21, 303-311,(1973).

Cullis, C.F., and Firth, J.G., Eds., Detection and Measurement of Hazardous Gases, Heinemann, Exeter, 29-67, (1981).

Stetter, J. R. and Zaromb, S., J., A Dynamic Coulometric Technique for Gas Analysis, Electroanal. Chem., 148, (1983), 271-277.

Alving, K. et al., Performance of a new hand-held device for exhaled nitric oxide measurement in adults and children, Respiratory Research 2006, 7:67.

Zirconia Oxygen Analysis, accessed Aug. 10, 2018 (Year: 2018).*

Scheffler, Towner Bennett et al. Written Opinion and International Search Report dated Feb. 18, 2014, of the counterpart PCT application PCT/US2013/064739 filed on Oct. 12, 2013.

* cited by examiner

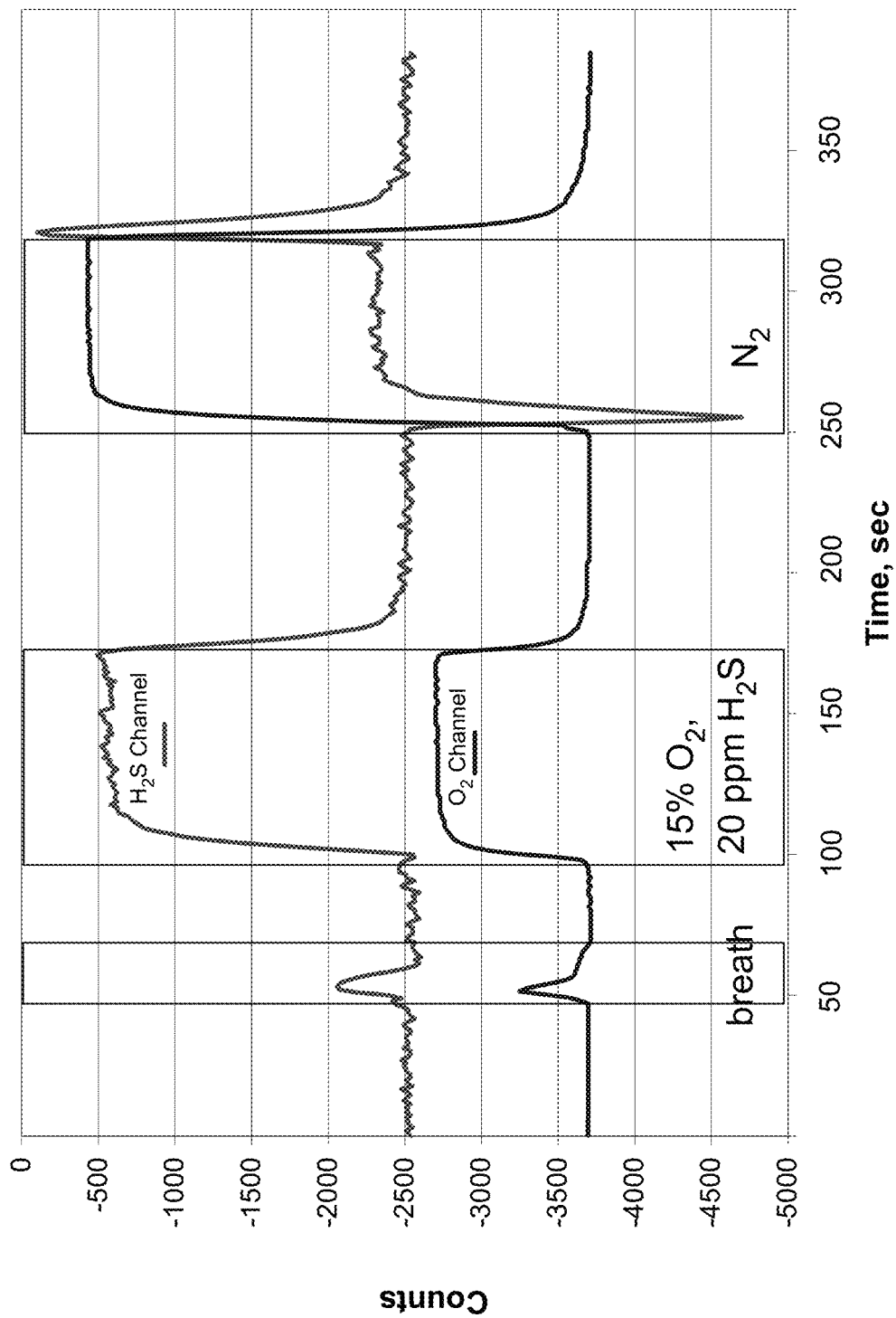

Fig. 13A
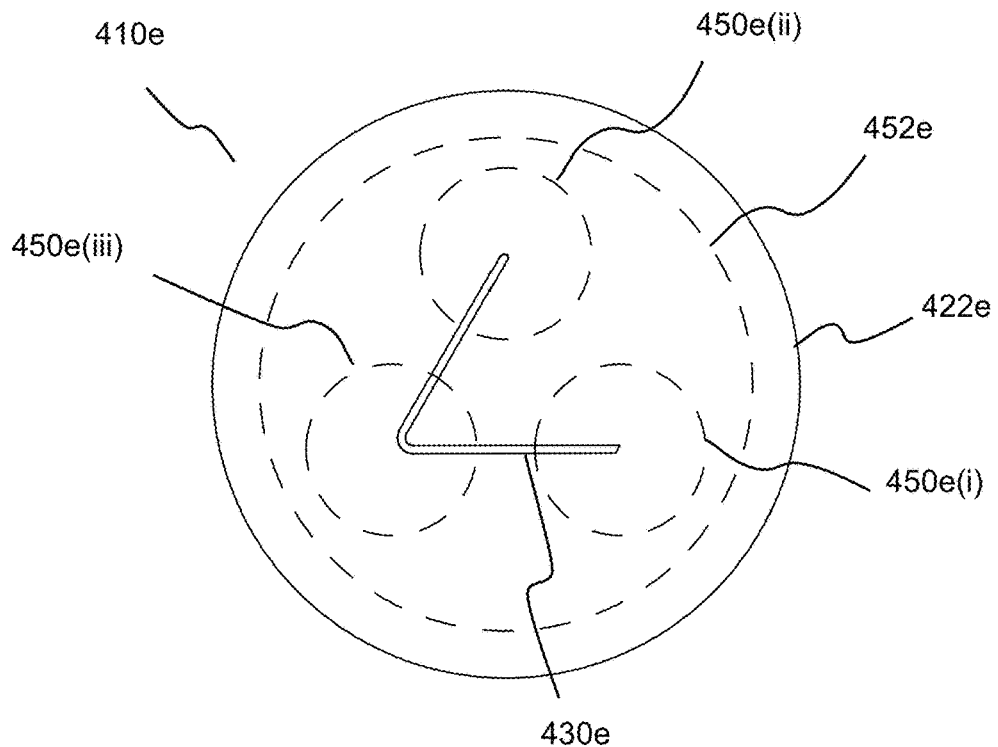
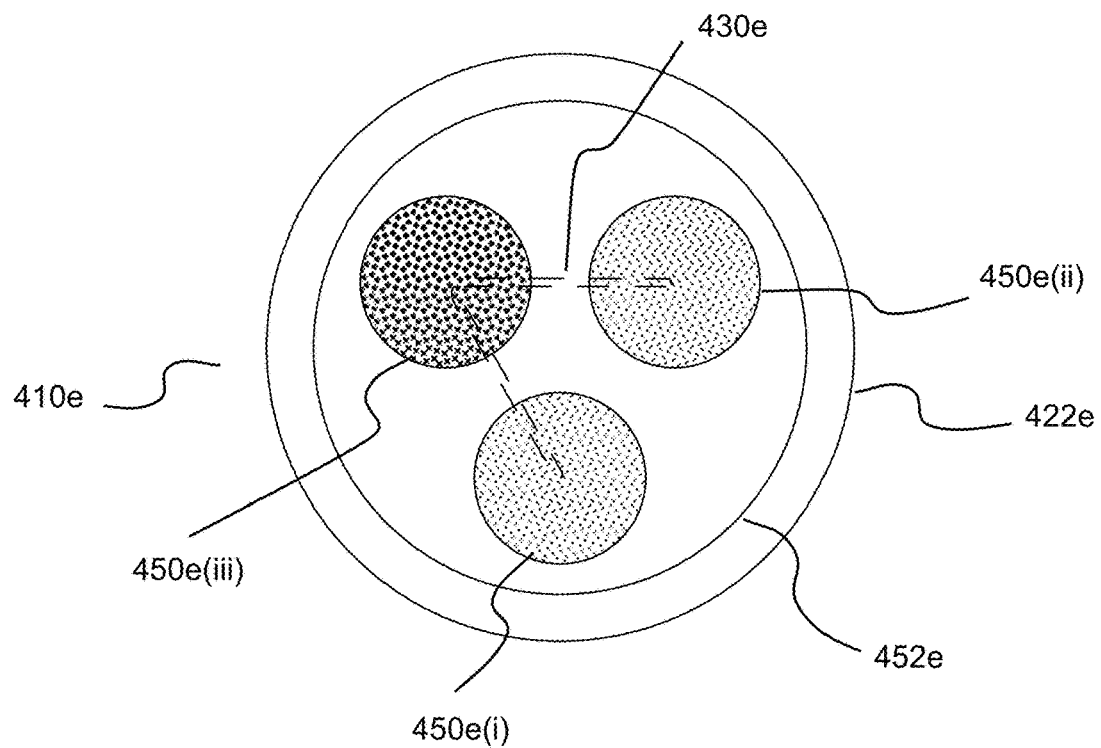
Fig. 13B

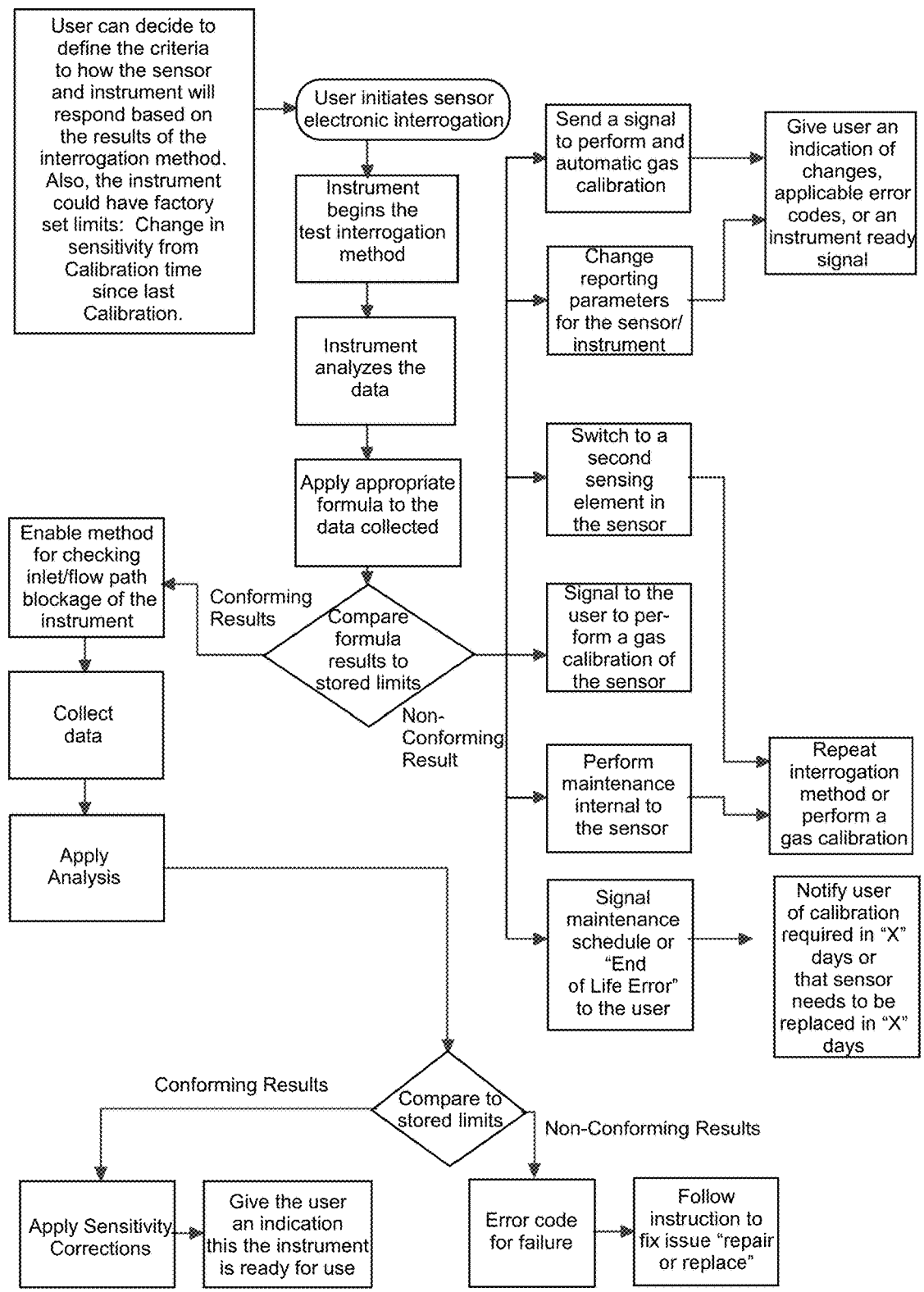
Fig. 14A — Decision tree for Life and Health followed by a check for inlet blockage.

Decision tree for Inlet Blockage testing followed by Life and health

SENSOR INTERROGATION

CROSS-REFERENCE TO RELATED APPLICATIONS

This application is a continuation application of U.S. patent application Ser. No. 13/796,652, filed Mar. 12, 2013, which is a continuation-in-part application of U.S. patent application Ser. No. 13/650,613, filed Oct. 12, 2012, which claims the benefit of U.S. Provisional Patent Application Ser. No. 61/547,245, filed Oct. 14, 2011, and U.S. Provisional Patent Application Ser. No. 61/698,153, filed Sep. 7, 2012, the disclosures of which are incorporated herein by reference.

BACKGROUND

The following information is provided to assist the reader in understanding certain technology including, for example, the devices, systems and/or methods disclosed below and representative environments in which such technology may be used. The terms used herein are not intended to be limited to any particular narrow interpretation unless clearly stated otherwise in this document. References set forth herein may facilitate understanding of the technology or the background thereof. The disclosure of all references cited herein are incorporated by reference.

Prudence dictates that gas detection instrumentation be tested regularly for functionality. It is a common practice to, for example, perform a "bump check," or functionality check on portable gas detection instrumentation on a daily basis. The purpose of this test is to ensure the functionality of the entire gas detection system, commonly referred to as an instrument. A periodic bump check or functionality check may also be performed on a permanent gas detection instrument to, for example, extend the period between full calibrations. Gas detection systems include at least one gas sensor, electronic circuitry and a power supply to drive the sensor, interpret its response and display its response to the user. The systems further include a housing to enclose and protect such components. A bump check typically includes: a) applying a gas of interest (usually the target gas or analyte gas the instrument is intended to detect); b) collecting and interpreting the sensor response; and c) indicating to the end user the functional state of the system (that is, whether or not the instrument is properly functioning).

Such bump tests are performed regularly and, typically, daily. Bump checks provide a relatively high degree of assurance to the user that the gas detection device is working properly. The bump check exercises all the necessary functionalities of all parts of the gas detection device in the same manner necessary to detect an alarm level of a hazardous gas. In that regard, the bump check ensures that there is efficient gas delivery from the outside of the instrument, through any transport paths (including, for example, any protection and/or diffusion membranes) to contact the active sensor components. The bump check also ensures that the detection aspect of the sensor itself is working properly and that the sensor provides the proper response function or signal. The bump check further ensures that the sensor is properly connected to its associated power supply and electronic circuitry and that the sensor signal is interpreted properly. Moreover, the bump check ensures that the indicator(s) or user interface(s) (for example, a display and/or an annunciation functionality) of the gas detection instrument is/are functioning as intended.

However, a periodic/daily bump check requirement has a number of significant drawbacks. For example, such bump checks are time consuming, especially in facilities that include many gas detection systems or instruments. The bump check also requires the use of expensive and potentially hazardous calibration gases. Further, the bump check also requires a specialized gas delivery system, usually including a pressurized gas bottle, a pressure reducing regulator, and tubing and adapters to correctly supply the calibration gas to the instrument. The requirement of a specialized gas delivery system often means that the opportunity to bump check a personal gas detection device is limited in place and time by the availability of the gas delivery equipment.

SUMMARY

In a number of aspects hereof, devices, systems and methods of testing the operational state or functionality of a system are provided. In a number of embodiments, the system includes at least one gas sensor for detecting an analyte gas (for example, an electrochemical sensor or a combustible gas sensor). The gas sensor is disposed within a housing of the system and is in fluid connection with an inlet system of the housing. The system further includes at least one sensor (which may be the same as or different from the gas sensor) within the housing and in fluid connection with the inlet system that is responsive to at least one driving force created, for example, in the vicinity of the inlet system. In a number of embodiments, the driving force is created other than by application of the at least one analyte gas or a simulant gas thereof to the system. The response of sensor responsive to the driving force provides an indication of a state of a transport path between the inlet system and sensor responsive to the driving force. The response of the sensor responsive to the driving force is not used to calibrate the gas sensor for detecting the analyte, but to test the state of one or more transport paths of the system. In many embodiments hereof, the sensor responsive to the driving force need not be an analytical sensor.

The driving force may, for example, be a change in the concentration of a gas, a change in humidity, a change in temperature, a change in pressure, or a change in flow/diffusion. In a number of embodiments, the driving force is created by exhalation of breath in the vicinity of the inlet system. Exhaled breath causes, for example, a change in flow, a change in temperature, a change in pressure, a change in humidity, and/or a change in gas concentrations, which may be measured by the sensor responsive to the driving force. The sensor may, for example, be responsive to changes in carbon dioxide concentration or changes in oxygen associated with the application of exhaled breath. The sensor responsive to the presence of exhaled breath may, for example, be an electrochemical sensor or a combustible gas sensor. In a number of other embodiments, the driving force is created by reducing or eliminating flow or diffusion (for example, by at least partially blocking the inlet system). In a number of such embodiments, the sensor responsive to the driving force is a sensor which causes a reaction of oxygen. Such a sensor may, for example, be an electrochemical sensor or a combustible gas sensor.

In a number of embodiments, devices, systems and/or methods are further provided to electronically interrogate the at least one gas sensor for detecting the analyte gas to determine the operational state or functionality thereof. In a number of embodiments hereof, the electronic interrogation proceeds without the application of the analyte gas or a simulant therefor to the system. For example, in the case that the sensor for detecting the analyte gas is an electrochemical sensor, electronic interrogation may include simulating the presence of the analyte gas electronically and measuring a response of an electrochemical sensor to the electronic simulation. In a number of embodiments, a constant current is caused to flow between a first working electrode and a counter electrode of the electrochemical sensor, and the measured response is a potential difference. In a number of embodiments, a constant potential difference is maintained between a first working electrode and a counter electrode of the electrochemical sensor, and the measured response is a current. The electrochemical sensor may, for example, be an amperometric sensor.

In the case that the at least one sensor for detecting the analyte is a combustible gas sensor, an electronic interrogation test for a sensing element of a combustible gas sensor may include measuring the reactance or capacitance of the sensing element. The measured reactance and/or capacitance may be related to an operational state or functionality of the sensing element.

In a number of embodiments, combination of a flow or transport path test hereof and a sensor electronic interrogation test hereof may reduce or eliminate the need for bump testing a sensor system as described above. Moreover, the time period between gas calibrations may be extended in a number of embodiments hereof.

In one aspect, a method is provided of testing a system having at least one electrochemical sensor for detecting an analyte gas within a housing of the system. The housing of the system has an inlet. The at least one electrochemical sensor includes an electrically active working electrode in fluid connection with the inlet of the system. The method includes biasing the electrically active working electrode at a first potential to detect the analyte gas and biasing the electrically active working electrode at a second potential, different from the first potential, such that the at least one electrochemical sensor is sensitive (at the second potential) to a driving force created in the vicinity of the inlet to test at least one transport path of the system. The method may further include creating the driving force in the vicinity of the inlet of the housing of the system and measuring a response of the electrically active working electrode to the driving force. In a number of embodiments, the driving force includes (a) application of exhaled breath or (b) restricting entry of molecules into the inlet. The method may, for example, further include returning the electrically active working electrode to the first potential.

In a number of embodiments, the electrically active working electrode is responsive to carbon dioxide at the second potential. In a number of other embodiments, the electrically active working electrode is responsive to oxygen at the second potential.

The method may, for example, further include electronically interrogating the at least one electrochemical sensor to test the functionality thereof to detect the analyte gas. In a number of embodiments, the method further includes simulating the presence of the analyte gas electronically and measuring a response of the at least one electrochemical sensor to the electronic simulation. A constant current may, for example, be caused to flow between the electrically active working electrode and a counter electrode of the at least one electrochemical sensor, and the measured response may be a potential difference. A constant potential difference may, for example, be maintained between the electrically active working electrode and a counter electrode of the at least one electrochemical sensor and the measured response is a current.

The at least one electrochemical sensor may, for example, be an amperometric sensor. In a number of embodiments, the at least one electrochemical sensor includes a sensor housing comprising at least one inlet into an interior of the sensor housing, and the electrically active working electrode is positioned within the sensor housing. The electrically active working electrode may, for example, include an eletrocatalytically active material deposited upon a porous membrane through which gas can diffuse.

In another aspect, a system for detecting an analyte gas includes a system housing including an inlet system, an electrochemical gas sensor within the housing and in fluid connection with the inlet system. The electrochemical sensor includes a working electrode responsive to the analyte gas. The system further includes a control system in electrical connection with the working electrode. The control system is operative to bias the working electrode at a first potential at which the electrochemical gas sensor is responsive to the analyte and operative to the working electrode at a second potential, different from the first potential, at which the electrochemical gas sensor is sensitive to a driving force created in the vicinity of the inlet system to test at least one transport path of the system. As described above, the driving force may, for example, include (a) application of exhaled breath or (b) restricting entry of molecules into the inlet system. In a number of embodiments, the working electrode is responsive to carbon dioxide at the second potential or the working electrode is responsive to oxygen at the second potential.

The control system may, for example, be adapted to cause or to effect electronic interrogation of the electrochemical sensor to test the functionality thereof to detect the analyte gas. The control system may, for example, be adapted to simulate the presence of the analyte gas electronically and measure a response of the electrochemical gas sensor to the electronic simulation. In a number of embodiments, the control system is adapted to cause a constant current to flow between the working electrode and a counter electrode of the electrochemical gas sensor, and the measured response is a potential difference. The control system may also be adapted to maintain a constant potential difference between the working electrode and a counter electrode of the electrochemical sensor, and the measured response may be a current.

In a number of embodiments of the system, the electrochemical gas sensor is an amperometric sensor. As described above, the electrochemical gas sensor may, for example, include a sensor housing comprising at least one inlet into an interior of the sensor housing, and the working electrode may, for example, be positioned within the sensor housing. The working electrode may, for example, include an eletrocatalytically active material deposited upon a porous membrane through which gas can diffuse.

In a further aspect, an electrochemical sensor for detecting an analyte gas in an environment includes a working electrode responsive to the analyte gas and a control system in electrical connection with the working electrode. The control system is operative to bias the working electrode at a first potential at which the electrochemical sensor is responsive to the analyte gas and to bias the working electrode at a second potential, different from the first potential, at which the sensor is sensitive to a driving force created in the vicinity of the inlet to test at least one transport path from the environment to the working electrode.

In another aspect, a method of operating a sensor system including at least one sensor for detecting an analyte gas and a control system includes electronically interrogating the sensor to determine the operational status thereof and, upon determining that the operational status is non-conforming based upon one or more predetermined thresholds, the control system initiating an automated calibration of the sensor with the analyte gas or a simulant gas. The control system may, for example, be in operative connection with a system including a container of the analyte gas or the simulant gas. The control system may, for example, cause or signal the system including the container to release the analyte gas or the simulant gas for use during the automated calibration. The control system may, for example, be in operative connection with a gas generation system to generate the analyte gas or the simulant gas for use during the automated calibration. The control system may signal or cause the gas generation system to generate the analyte gas or the simulant gas to effect the calibration. The method may, for example, further include changing at least one reporting parameter of the sensor after the automated calibration. In a number of embodiments, the sensor is an electrochemical sensor or a combustible gas sensor.

Control systems hereof may, for example, include control circuitry and/or one or more processors (for example, microprocessors). In a number of embodiments, the electronic interrogations hereof may, for example, be initiated by a user or by a control system hereof (either with or without user intervention). In any embodiments hereof including a control system having a computer processor, one or more actions to be effected by the control system may, for example, be embodied in software stored in a memory system in communicative connection with the processor.

In another aspect, a method of operating a sensor system including at least one sensor for detecting an analyte gas and a control system includes electronically interrogating the at least one sensor to determine the operational status thereof and changing at least one reporting parameter of the sensor via the control system on the basis of results of electronically interrogating the at least one sensor. The at least one reporting parameter may, for example, include a range, a resolution, a cross-sensitivity parameter, a set point, and/or an alarm signal. In a number of embodiments, the sensor is an electrochemical sensor or a combustible gas sensor.

In a further aspect, a method of operating a sensor system including a first sensor to detect a first gas analyte, a second sensor and a control system includes electronically interrogating at least the first sensor to determine the operational status thereof and, based upon the results of the electronic interrogation, the control system switching from the first sensor to the second sensor to detect the first gas analyte. For example, the first sensor may be determined to be inoperative to detect the first gas analyte on the basis of the electronic interrogation. In a number of embodiments, the first sensor is an electrochemical sensor and the second sensor is an electrochemical sensor or a combustible gas sensor.

In another aspect, a method of operating a sensor system including a first sensor to detect a first gas analyte and a control system includes electronically interrogating the first sensor to determine the operational status thereof and, based upon the results of the electronic interrogation, the control system switching the first sensor from detecting the first gas analyte to detecting a second gas analyte that is different from the first gas analyte. The first sensor may, for example, be determined to be inoperative to detect the first gas analyte on the basis of the electronic interrogation, but may still be operative to detect the second gas analyte. The first sensor may be an electrochemical sensor, and the second sensor may be an electrochemical sensor. The first sensor may, for example, be a combustible sensor.

In another aspect, a method of operating a sensor system including at least a first sensor to detect a first gas analyte and a control system includes electronically interrogating the sensor to determine the operational status thereof and, based upon the results of the electronic interrogation, the control system initiating an automated maintenance procedure for the sensor. The first sensor may, for example, be an electrochemical sensor including a first working electrode responsive to the first gas analyte. The maintenance procedure may, for example, include altering a bias potential of the first working electrode. In a number of embodiments, the maintenance procedure includes (a) altering the bias potential of the first working electrode to increase a sensitivity of the first working electrode to the first gas analyte, (b) altering the bias potential of the first working electrode to enhance an ability of the first working electrode to discriminate against a gas other than the first gas analyte, or (c) altering the bias potential of the first working electrode to remove contaminant from the first working electrode.

In another aspect, a method is provided of operating a system including at least a first sensor to detect a first gas analyte. The first sensor is positioned within a housing which has at least one inlet. The system further includes a control system. The method includes testing a state of at least one transport path of the system by creating a driving force in the vicinity of the at least one inlet of the housing other than by application of the first gas analyte or a simulant gas for the analyte and adjusting an output of the at least first sensor via the control system at least in part on the basis of the results of the test of the state of the at least one transport path. The method may, for example, include measuring the rate of change of sensor response to the driving force and correlating the rate of change of sensor response to a correction factor for sensitivity of the first sensor to the gas analyte. In a number of embodiments, a peak in the rate of change of sensor response to the driving force is correlated to a correction factor for sensitivity of the first sensor to the gas analyte. The first sensor may, for example, include an electrochemical sensor or a combustible gas sensor. Correlation to a correction factor may, for example, include reference to a look-up table or use of an algorithm or formula.

In another aspect, a system includes at least one sensor for detecting an analyte gas and a control system. The control system is operational to or adapted to electronically interrogate the sensor to determine the operational status thereof. Upon a determination that the operational status is non-conforming based upon one or more predetermined thresholds, the control system initiates an automated calibration of the sensor with the analyte gas or a simulant gas. The control system may, for example, be in operative connection with a system comprising a container of the analyte gas or the simulant gas. The control system may signal or cause the system including the container to release the analyte gas or the simulant gas for use during the automated calibration. The control system may be in operative connection with a gas generation system to generate the analyte gas or the simulant gas for use during the automated calibration. The control system may signal or cause the gas generation system to generate the analyte gas or the simulant gas to generate that gas to initiate a calibration. The control system may, for example, be adapted to change at least one reporting parameter of the sensor after the automated calibration.

In a number of embodiments, the sensor is an electrochemical sensor or a combustible gas sensor.

In a further aspect, a system includes at least one sensor for detecting an analyte gas and a control system. The control system is operational to or adapted to electronically interrogate the at least one sensor to determine the operational status thereof, and the control system is further adapted to change at least one reporting parameter of the sensor on the basis of results of electronically interrogating the at least one sensor. The at least one reporting parameter may, for example, be a range, a resolution, a cross-sensitivity parameter, a set point, and/or an alarm signal. The sensor may, for example, be an electrochemical sensor or a combustible gas sensor.

In another aspect, a system includes a first sensor to detect a first gas analyte, a second sensor and a control system. The control system is operational to or adapted to electronically interrogate at least the first sensor to determine the operational status thereof and, based upon the results of the electronic interrogation, the control system is further adapted to switch from the first sensor to the second sensor to detect the first gas analyte. The first sensor may be an electrochemical sensor, and the second sensor may be an electrochemical sensor. The first sensor may be a combustible gas sensor, and the second sensor may be combustible gas sensor.

In another aspect, a system includes a first sensor to detect a first gas analyte and a control system. The control system is operational to or adapted to electronically interrogate the first sensor to determine the operational status thereof and, based upon the results of the electronic interrogation, the control system is further adapted to switch the first sensor from detecting the first gas analyte to detecting a second gas analyte that is different from the first gas analyte. In a number of embodiments, the first sensor is an electrochemical sensor, and the second sensor is an electrochemical sensor. In a number of embodiments, the first sensor is a combustible sensor.

In another aspect, a system includes at least a first sensor to detect a first gas analyte and a control system. The control system is operational to or is adapted to electronically interrogate the sensor to determine the operational status thereof. Based upon the results of the electronic interrogation, the control system is further adapted to initiate an automated maintenance procedure for the sensor. In a number of embodiments, the first sensor is an electrochemical sensor comprising a first working electrode responsive to the first gas analyte. The maintenance procedure may, for example, include altering a bias potential of the first working electrode. In a number of embodiments, the maintenance procedure includes: (a) altering the bias potential of the first working electrode to increase a sensitivity of the first working electrode to the first gas analyte, (b) altering the bias potential of the first working electrode to enhance an ability of the first working electrode to discriminate against a gas other than the first gas analyte, or (c) altering the bias potential of the first working electrode to remove a contaminant from the first working electrode. In a number of embodiments, the first sensor is a combustible sensor.

In another aspect, a system includes at least a first sensor to detect a first gas analyte positioned within a housing having at least one inlet. The system further includes a control system. The control system is operational to or adapted to test or interrogate a state of at least one transport path of the system by creating a driving force in the vicinity of the at least one inlet of the housing other than by application of the first analyte or a simulant gas for the analyte. The system is further adapted to adjust an output of the at least first sensor at least in part on the basis of the results of the test of the state of the at least one transport path. In a number of embodiments, a rate of change of sensor response to the driving force is measured and correlated to a correction factor for sensitivity of the first sensor to the gas analyte. A peak in the rate of change of sensor response to the driving force may, for example, be correlated to a correction factor for sensitivity of the first sensor to the gas analyte. The first sensor may, for example, be an electrochemical sensor or a combustible gas sensor.

In another aspect, a method of operating a sensor system including a first sensor to detect a first gas analyte includes electronically interrogating at least the first sensor to determine the operational status thereof and, based upon the results of the electronic interrogation, notifying the user of at least one of a need to calibrate the sensor with the first gas analyte or a simulant gas for the first gas analyte or a need to perform maintenance other than calibration.

In another aspect, a system includes at least a first sensor to detect a first gas analyte positioned within a housing having at least one inlet. The system further includes a control system. The control system is operational to or adapted to electronically interrogate at least the first sensor to determine the operational status thereof. Based upon the results of the electronic interrogation, the control system is further adapted to notify the user of at least one of a need to calibrate the sensor with the first gas analyte or a simulant gas for the first gas analyte or a need to perform maintenance other than calibration.

In a further aspect, a method of operating a sensor system including a first sensor to detect a first gas analyte includes electronically interrogating at least the first sensor to determine the operational status thereof and based upon the results of the electronic interrogation, notifying the user of an end of life of the sensor, which is, for example, to occur in a determined period of time.

In a further aspect, a system includes at least a first sensor to detect a first gas analyte positioned within a housing having at least one inlet. The system further includes a control system. The control system is operational to or adapted to electronically interrogate at least the first sensor to determine the operational status thereof. Based upon the results of the electronic interrogation, the control system is further adapted to notify the user of an end of life of the sensor, which is, for example, to occur in a determined period of time.

In another aspect, a method of operating a system having at least one sensor for detecting an analyte gas (for example, an analyte other than oxygen) in an ambient atmosphere and a sensor responsive to oxygen includes providing a volume in fluid connection with the sensor responsive to oxygen. The volume has a state, sometimes referred to herein as an open state, in which the volume is in fluid connection with the ambient atmosphere and at least a first restricted state, in which entry of molecules from the ambient atmosphere into the volume is restricted as compared to the open state. The method further includes placing the volume in the open state, subsequently placing the volume in the first restricted state, and measuring a dynamic output of the sensor responsive to oxygen while the volume is in the first restricted state. The dynamic output provides an indication of the status of one or more transport paths of the system. The molecules from the ambient atmosphere may, for example, be prevented from entering the volume in the first restricted state.

In a number of embodiments, the system further includes a control system to control whether the volume is in the open state or in the first restricted state. The control system may, for example, be activated from a position remote from the position of the system. The control system may, for example, be adapted to place the volume in the open state or in the first restricted state on the basis of a predetermined programming. This may, for example, be automated (that is, without human intervention), and may be based, for example, upon a periodic schedule or a triggering event.

The at least one sensor for detecting an analyte gas other than oxygen may, for example, be an electrochemical sensor and the method may, for example, further include electronically interrogating the electrochemical sensor. Electronic interrogation of the electrochemical sensor may, for example, include simulating the presence of the analyte gas electronically and measuring a response of the electrochemical sensor to the electronic simulation. The electrochemical sensor may, for example, be an amperometric sensor.

In a number of embodiments, the electrochemical sensor is also the sensor responsive to oxygen and the electrochemical sensor includes a first working electrode responsive to the analyte gas and a second working electrode responsive to oxygen. The electrochemical sensor may, for example, include a sensor housing including at least one inlet into an interior of the sensor housing. The first working electrode and the second working electrode may, for example, be positioned within the sensor housing.

In a number of embodiments, the sensor responsive to oxygen is an electrochemical gas sensor. In a number of embodiments, the sensor responsive to oxygen is a non-analytical sensor In another aspect, a system to detect an analyte gas in an ambient atmosphere includes a sensor to detect the analyte gas, a sensor responsive to oxygen, a volume in fluid connection with the sensor responsive to oxygen, and a restrictor mechanism to place the volume in an open state in which the volume is in fluid connection with the ambient atmosphere and in at least a first restricted state in which entry of molecules from the ambient atmosphere into the volume is restricted as compared to the open state. The system further includes a processing system to measure a dynamic output of the sensor responsive to oxygen while the volume is in the first restricted state. The dynamic output provides an indication of the status of one or more transport paths of the system. The processing system may, for example, include a processor such as a microprocessor and/or other electronic circuitry. In a number of embodiments, the molecules from the ambient atmosphere are prevented from entering the volume in the first restricted state.

The system may for example include a control system in operative connection with the restrictor mechanism to control whether the volume is in the open state or in the first restricted state. The control system may, for example, be activated from a position remote from the position of the system. In a number of embodiments, the control system is adapted to place the volume in the open state or in the first restricted state on the basis of predetermined programming (for example, embodied in software programming).

In a number of embodiments, the system further includes at least one electrochemical sensor to detect the analyte gas, a system to simulate the presence of the analyte gas electronically, and a system to measure a response of the electrochemical sensor to the electronic simulation. A constant current may, for example, be caused to flow between a first working electrode and a counter electrode of the electrochemical sensor, and the measured response may a potential difference. A constant potential difference may, for example, be maintained between a first working electrode and a counter electrode of the electrochemical sensor, and the measured response may be a current.

The electrochemical sensor may, for example, be an amperometric sensor. The electrochemical sensor may, for example, also be the sensor responsive to oxygen, and the electrochemical sensor may include a first working electrode responsive to the analyte gas and a second working electrode responsive to oxygen. In a number of embodiments, the electrochemical sensor includes a sensor housing including at least one inlet into an interior of the sensor housing. The first working electrode and the second working electrode may, for example, be positioned within the sensor housing.

The sensor responsive to oxygen may, for example, be an electrochemical gas sensor. In a number of embodiments, the sensor responsive to oxygen is a non-analytical sensor.

The system may, for example, further include a housing in which the sensor to detect the analyte gas and the sensor responsive to oxygen are disposed. The housing may, for example, include an inlet, and the restrictor mechanism may be in operative connection with the inlet to at least partially block the inlet from fluid connection with the ambient atmosphere in the first restricted state.

In a further aspect, a method of operating a system including a housing having an inlet and a sensor disposed within the housing, includes providing a first state in which the inlet is in fluid connection with an ambient atmosphere and at least a second state in which entry of molecules from the ambient atmosphere into the volume is more restricted compared to the first state, placing the inlet in the first state, subsequently placing the inlet in the second state, and measuring a dynamic output or response of the sensor while the inlet is in the second state. The dynamic output provides an indication of the status of one or more transport paths of the system.

In another aspect, a system includes a system housing including an inlet, at least one gas sensor responsive to a first analyte gas other than oxygen within the system housing and in fluid connection with the inlet, and a sensor responsive to oxygen within the system housing and in fluid connection with the inlet. The sensor responsive to oxygen is formed to be chemically separate from the at least one gas sensor responsive to the first analyte gas other than oxygen. The sensor responsive to oxygen is responsive to a change in the concentration of oxygen arising from creation (for example, application) of a driving force in the vicinity of the inlet to provide an indication of a state of a transport path between the inlet of the system and the at least one gas sensor responsive to the first analyte gas other than oxygen. The driving force may, for example, include application of exhaled breath or closing of the inlet from fluid connection with the environment surrounding the housing.

The sensor responsive to oxygen may, for example, include an electrochemically active electrode responsive to oxygen. In a number of embodiments, the sensor responsive to oxygen is non-analytically responsive to oxygen (that is, the sensor is a non-analytical sensor).

The system may, for example, further include an electrochemical gas sensor analytically responsive to oxygen within the housing and in fluid connection with the inlet. The electrochemical gas sensor analytically responsive to oxygen may, for example, be formed separately from the at least one gas sensor responsive to the first analyte gas other than oxygen and the sensor responsive to oxygen.

The system may, for example, further include a system to electronically interrogate at least one gas sensor responsive to the at least one analyte gas other than oxygen to test the functionality thereof to detect the at least one analyte gas other than oxygen. The system may include one or more systems to electronically interrogate multiple sensors of the system.

In a number of embodiments, the at least one gas sensor responsive to the at least one analyte gas other than oxygen is an electrochemical gas sensor. The system may, for example, further include a system to simulate the presence of the analyte gas electronically in operative connection with the electrochemical gas sensor responsive to the at least one analyte gas other than oxygen and a system to measure a response of the electrochemical gas sensor responsive to the at least one analyte gas other than oxygen to the electronic simulation. A constant current may, for example, be caused to flow between a first working electrode and a counter electrode of the electrochemical gas sensor responsive to the at least one analyte gas other than oxygen, and the measured response may be a potential difference. A constant potential difference may, for example, be maintained between a first working electrode and a counter electrode of the electrochemical gas sensor responsive to the at least one analyte gas other than oxygen, and the measured response may be a current. The electrochemical gas sensor responsive to the at least one analyte gas other than oxygen may, for example, be an amperometric sensor.

In another aspect, a method of fabricating a system includes providing a system housing which includes an inlet, disposing at least one gas sensor responsive to a first analyte gas other than oxygen within the system housing and in fluid connection with the inlet, and disposing a sensor responsive to oxygen within the system housing and in fluid connection with the inlet. The sensor responsive to oxygen is formed to be chemically separate from the at least one gas sensor responsive to the first analyte gas other than oxygen. The sensor responsive to oxygen is responsive to a change in the concentration of oxygen arising from creation of a driving force in the vicinity of the inlet to provide an indication of a state of a transport path between the inlet of the system and the at least one gas sensor responsive to the first analyte gas other than oxygen.

In another aspect, a method of operating a system is provided wherein the system includes a system housing including an inlet, at least one gas sensor responsive to a first analyte gas other than oxygen within the system housing and in fluid connection with the inlet, and a sensor responsive to oxygen within the system housing and in fluid connection with the inlet. The sensor responsive to oxygen is formed to be chemically separate from the at least one gas sensor responsive to the first analyte gas other than oxygen. The method includes creation of a driving force in the vicinity of the inlet that causes a change in the concentration of oxygen in the vicinity of the sensor responsive to oxygen. The associated response of the sensor responsive to oxygen provides an indication of a state of a transport path between the inlet of the system and the at least one gas sensor responsive to the first analyte gas other than oxygen. The driving force may, for example, include application of exhaled breath or restricting/closing the inlet from fluid connection with the environment surrounding the housing.

As described above, the sensor responsive to oxygen may, for example, include an electrochemically active electrode responsive to oxygen. In a number of embodiments, the sensor responsive to oxygen is non-analytically response to oxygen.

An electrochemical gas sensor analytically responsive to oxygen may, for example, be disposed within the housing and in fluid connection with the inlet. The electrochemical gas sensor analytically responsive to oxygen may, for example, be formed chemically separately from the at least one gas sensor responsive to the first analyte gas other than oxygen and from the sensor responsive to oxygen.

The method may further include electronically interrogating the at least one gas sensor responsive to the at least one analyte gas other than oxygen to test the functionality thereof to detect the at least one analyte gas other than oxygen. Other sensors of the system may also be electronically interrogated. In a number of embodiments, the at least one gas sensor responsive to the at least one analyte gas other than oxygen is an electrochemical gas sensor, and the method further includes providing a system to simulate the presence of the analyte gas electronically in operative connection with the electrochemical gas sensor responsive to the at least one analyte gas other than oxygen and providing a system to measure a response of the electrochemical gas sensor responsive to the at least one analyte gas other than oxygen to the electronic simulation.

In a further aspect, a system includes a first gas sensor responsive to a first analyte gas, a second gas sensor responsive to the first analyte gas, and a control system adapted to operate the first gas sensor in a sensing mode wherein a signal from the first gas sensor is representative of a concentration of the first analyte gas measured by the first gas sensor and in an interrogation mode wherein the first gas sensor is interrogated to test the functionality of the first gas sensor. The control system is also adapted to operate the second gas sensor in a sensing mode (wherein a signal from the second gas sensor is representative of a concentration of the first analyte gas measured by the second gas sensor) and in an interrogation mode (wherein the second gas sensor is interrogated to test the functionality of the second gas sensor). The control system places the first gas sensor in the interrogation mode only if the second gas sensor is in the sensing mode, and places the second gas sensor in the interrogation mode only if the first gas sensor is in the sensing mode. The first sensor may, for example, be a first electrochemical sensor, and the second sensor may be a second electrochemical gas sensor. The system may, for example, further include a system to simulate the presence of the analyte gas electronically in operative connection with the first electrochemical gas sensor to interrogate the first electrochemical gas sensor during the interrogation mode and in operative connection with the second electrochemical gas sensor to interrogate the second electrochemical gas sensor during the interrogation mode and a system to measure a response of the first electrochemical gas sensor to the electronic simulation and a system to measure a response of the second electrochemical gas sensor to the electronic simulation.

In still a further aspect, a method of operating a sensor including a first gas sensor responsive to a first analyte gas and a second gas sensor responsive to the first analyte gas includes operating the first gas sensor in a sensing mode (wherein a signal from the first gas sensor is representative of a concentration of the first analyte gas measured by the first gas sensor) and in an interrogation mode (wherein the first gas sensor is interrogated to test the functionality of the first gas sensor); operating the second gas sensor in a sensing mode (wherein a signal from the second gas sensor is representative of a concentration of the first analyte gas measured by the second gas sensor) and in an interrogation mode (wherein the second gas sensor is interrogated to test the functionality of the second gas sensor); and placing the first gas sensor in the interrogation mode only if the second gas sensor is in the sensing mode and placing the second gas sensor the interrogation mode only if the first gas sensor is in the sensing mode.

In a number of embodiments, the first sensor is a first electrochemical sensor and the second sensor is a second electrochemical gas sensor. The method may, for example, further include simulating the presence of the analyte gas electronically during the interrogation mode of the first electrochemical gas sensor to interrogate the first electrochemical gas sensor; simulating the presence of the analyte gas electronically during the interrogation mode of the second sensor to interrogate the second electrochemical gas sensor; measuring a response of the first electrochemical gas sensor to the electronic simulation thereof; and measuring a response of the second electrochemical gas sensor to the electronic simulation thereof.

Systems and methods hereof may further include a pump in fluid connection with the inlet or inlet system to pump gas from the ambient atmosphere into the housing via an inlet or inlet system. In such systems and methods, a system to detect a pump fault may be provided in operative connection with the pump.

The present devices, systems and/or methods, along with the attributes and attendant advantages thereof, will best be appreciated and understood in view of the following detailed description taken in conjunction with the accompanying drawings.

BRIEF DESCRIPTION OF THE DRAWINGS

FIG. 4 illustrates a study of the response of the sensor of FIG. 3A, wherein the first working electrode is sensitive to hydrogen sulfide and the second working electrode is sensitive to oxygen, when challenged with exhaled breath, followed by a mixture of 15 vol-% oxygen and 20 ppm hydrogen sulfide, followed by nitrogen.

FIG. 13A illustrates a top view of an embodiment of a sensor including redundant working electrode/channels for detecting a single analyte and a non-analytical working electrode which is sensitive to a driving force to effect a flow path test hereof.

FIG. 13B illustrates a bottom view of a portion of the sensor of FIG. 13A illustrating the dispersion of the electrocatalytic materials for the first analytical working electrode, the second working analytical electrode and the non-analytical working electrode on a single porous support.

FIG. 14A illustrates a flow chart of an embodiment of a sensor/system interrogation process hereof.

DETAILED DESCRIPTION

It will be readily understood that the components of the embodiments, as generally described and illustrated in the figures herein, may be arranged and designed in a wide variety of different configurations in addition to the described exemplary embodiments. Thus, the following more detailed description of the exemplary embodiments, as represented in the figures, is not intended to limit the scope of the embodiments, as claimed, but is merely representative of exemplary embodiments.

Reference throughout this specification to "one embodiment" or "an embodiment" (or the like) means that a particular feature, structure, or characteristic described in connection with the embodiment is included in at least one embodiment. Thus, the appearance of the phrases "in one embodiment" or "in an embodiment" or the like in various places throughout this specification are not necessarily all referring to the same embodiment.

Furthermore, described features, structures, or characteristics may be combined in any suitable manner in one or more embodiments. In the following description, numerous specific details are provided to give a thorough understanding of the embodiments. One skilled in the relevant art will recognize, however, that the various embodiments can be practiced without one or more of the specific details, or with other methods, components, materials, et cetera. In other instances, well known structures, materials, or operations are not shown or described in detail to avoid obfuscation.

As used herein and in the appended claims, the singular forms "a," "an", and "the" include plural references unless the context clearly dictates otherwise. Thus, for example, reference to "a transport path" includes a plurality of such transport paths and equivalents thereof known to those skilled in the art, and so forth, and reference to "the transport path" is a reference to one or more such transport paths and equivalents thereof known to those skilled in the art, and so forth.

Figure 1:
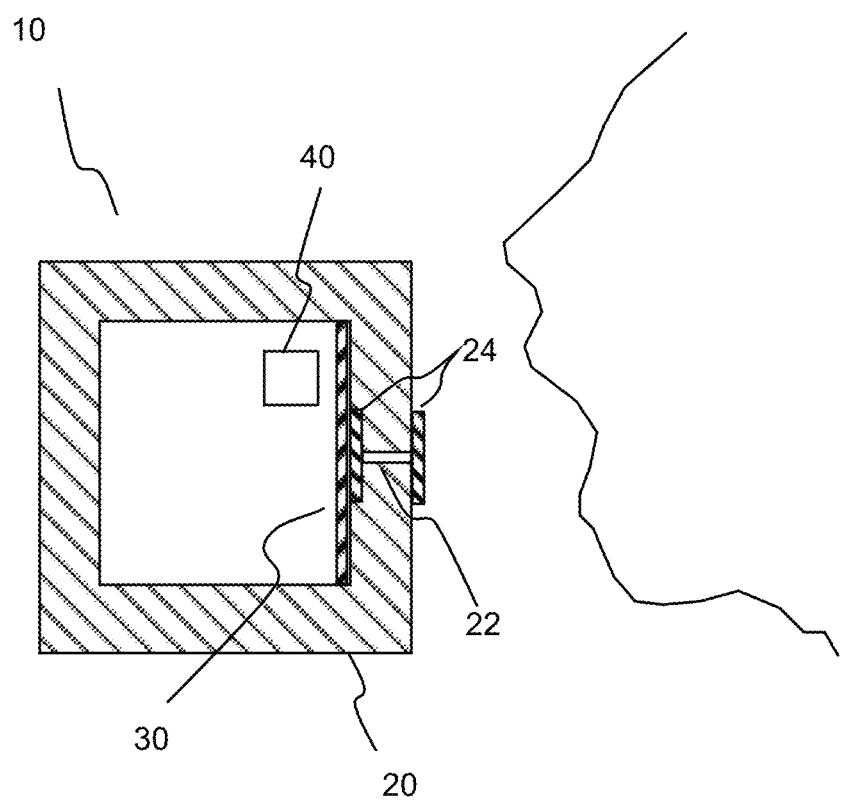
FIG. 1 illustrates a user exhaling in a manner that the user's exhaled breath impinges upon an inlet of a system including a housing enclosing a sensor that is sensitive to at least one property of exhaled breath.

As, for example, illustrated schematically in FIG. 1, in a number of embodiments, the devices, systems and/or methods hereof are operable to test transport properties of a gas detection or other system 10 via application of a driving force other than an analyte gas or a simulant gas (that is, a gas simulating the analyte gas by evoking a response from an analytical electrode of the system) from a container to one or more inlets 22 or an inlet system of an enclosing housing 20 of system 10. In a number of embodiments, the driving force may, for example, be the application of exhaled breath to inlet(s) 22. Housing 20 may, for example, include a mass transport path into an interior thereof (for example, a diffusion path) in fluid connection with inlet 22. System 10, may, for example, include, one or more filters 24 in fluid connection with inlet 22 either external or internal to housing 20. The path may, for example, include or be in fluid connection with a mass transport or diffusion member or barrier 30 (for example, a membrane through which gas is mobile (for example, via diffusion) but through which a liquid has limited or no mobility). Housing 20 encloses a sensor 40 which is sensitive to the presence of exhaled breath. For example, sensor 40 may be sensitive to an environmental gas (the concentration of which is changed by the presence of exhaled breath), to a gas within exhaled breath, to a change in humidity, to a change in temperature, to a change in pressure, to a change in flow etc. A response of sensor 40 to exhaled breath provides a measurement of the transport properties and/or functionality of one or more transport paths of system 10. Filter 24 may, for example, be used to filter out interferent gasses (that is, gasses other than the analyte gas to which the sensor is responsive) or to filter out inhibitors or poisons.

In a number of representative embodiments discussed herein, devices, systems and/or methods hereof decrease or eliminate the necessity to bump check a gas detection instrument with stored calibration (for example, an analyte or a simulant) gas. Such representative embodiments of systems, devices and/or methods may, for example, combine an internal, electronic check or interrogation of sensor functionality, connection, and/or correction without the application of an analyte gas or a simulant therefor (as, for example, described in U.S. Pat. No. 7,413,645) with a transport path test using, for example, a "secondary" sensor sensitive responsive to a driving force other than the presence of an analyte gas or a simulant gas (for example, a driving force/variable change arising from the presence of exhaled human breath as described above).

Many gas detection devices, instruments or systems (for example, portable gas detection instruments) include amperometric electrochemical gas sensors. These sensors are often referred to as "fuel cell" type sensors, which refers to a primary principle of operation. Such electrochemical gas sensors are typically combined or integrated into a device, system or instrument with a battery or other power supply, appropriate electronic driving circuitry (for example, including a potentiostat), a display, and one or more alarms (or other means of communicating to the user the presence of a dangerous level of harmful or toxic gas or a condition of dangerous oxygen depletion or enrichment). The sensor, circuitry and displays are typically contained in a rugged, sealed housing. As used in connection with such an instrument, the term "sealed" refers to protection of the sensor, circuitry, and displays from harmful environmental hazards (for example, dusts, condensing vapors, such as paints or coatings, and water and/or other liquids). However, the sealed housing must continually provide for the efficient transfer of the target or analyte gas(es) from outside the instrument housing into a housing of the sensor itself. Often, this result is accomplished with one or more porous diffusion membranes that keep dusts, vapors, and liquids out of the instrument housing, but allow one or more analyte gases of interest to be transported into the sensor itself. This transport is typically accomplished by gaseous diffusion or by pumping an analyte gas stream into or across the face of the sensor.

As described above, the need to bump check a gas detection system/device with a calibration or simulant gas from a container is decreased or eliminated by providing a sensor (for example, a secondary sensor) that is sensitive to or responds to a driving force or variable change in the vicinity of the inlet of the system, such as, for example, the presence of exhaled breath. In a number of embodiments, components which make a sensor responsive to oxygen are provided in an amperometric electrochemical sensor (which is functional to detect an analyte other than oxygen). Exhaled human breath typically includes 4 to 5 volume-percent (vol-%) of carbon dioxide ($CO_2$) and 15.8 to 16.8 vol-% oxygen ($O_2$). In contrast, ambient air includes approximately 20.8 vol-% $O_2$ and 0.035 vol-% $CO_2$. Thus, when a user exhales in the vicinity of one or more inlets into the housing of the detection system or instrument, the exhaled breath displaces the volume of gas (ambient air) within a diffusion volume in a sensor therein with the exhaled breath. A response to the decreased concentration of oxygen in exhaled breath as compared to ambient air may be used to test the transport properties of whatever gas transport path or mechanism may be used in the gas detection device (for example, including one or more gas diffusion membranes). The same result may, for example, be accomplished by incorporating, within or along with, for example, a toxic gas, a combustible or other sensor channel, a sensing element (which may be the same as or different from the sensing element for the analyte) that responds to any or all components of exhaled breath. For example, a similar result may be obtained by including a sensor or sensing functionality that responds to the increased concentration of $CO_2$ in exhaled breath as compared to ambient air. In that regard, exhaled breath contains approximately 5 vol % $CO_2$, as compared to ambient air, which contains approximately 600 ppm $CO_2$ (0.06 vol-%). A sensor or sensing system to measure $CO_2$ concentration may, for example, include an electrochemical sensor and/or a non-dispersive infrared sensor.

Amperometric or fuel cell-type gas sensors typically include at least two electrocatalytic electrodes (an anode and a cathode), at least one of which is a gas diffusion electrode or working electrode. The working electrode can be either the anode or the cathode in any given sensor. The gas diffusion electrode typically includes fine particles of an electrocatalytic material adhered to one side of a porous or gas-permeable membrane.

The electrocatalytic side of the working electrode is in ionic contact with the second electrode (the counter electrode, whether the anode or the cathode) via an electrolyte (for example, a liquid electrolyte, a solid electrolyte, a quasi-solid state electrolyte or an ionic liquid). A liquid electrolyte is typically a solution of a strong electrolyte salt dissolved in a suitable solvent, such as water. An organic solvent may also be used. Quasi-solid state electrolytes can, for example, include a liquid electrolyte immobilized by a high-surface-area, high-pore-volume solid. The working electrode and the counter electrode are also in electrical contact via an external circuit used to measure the current that flows through the sensor.

Additionally, although by no means necessary, a third or reference electrode, is often included. The reference electrode is constructed in a way that its potential is relatively invariant over commonly occurring environmental conditions. The reference electrode serves as a fixed point in potential space against which the operating potential of the working electrode may be fixed. In this way, electrochemical reactions that would not normally be accessible may be used to detect the analyte gas of interest. This result may be accomplished via control and driving circuitry which may, for example, include a potentiostat.

Figure 2A:
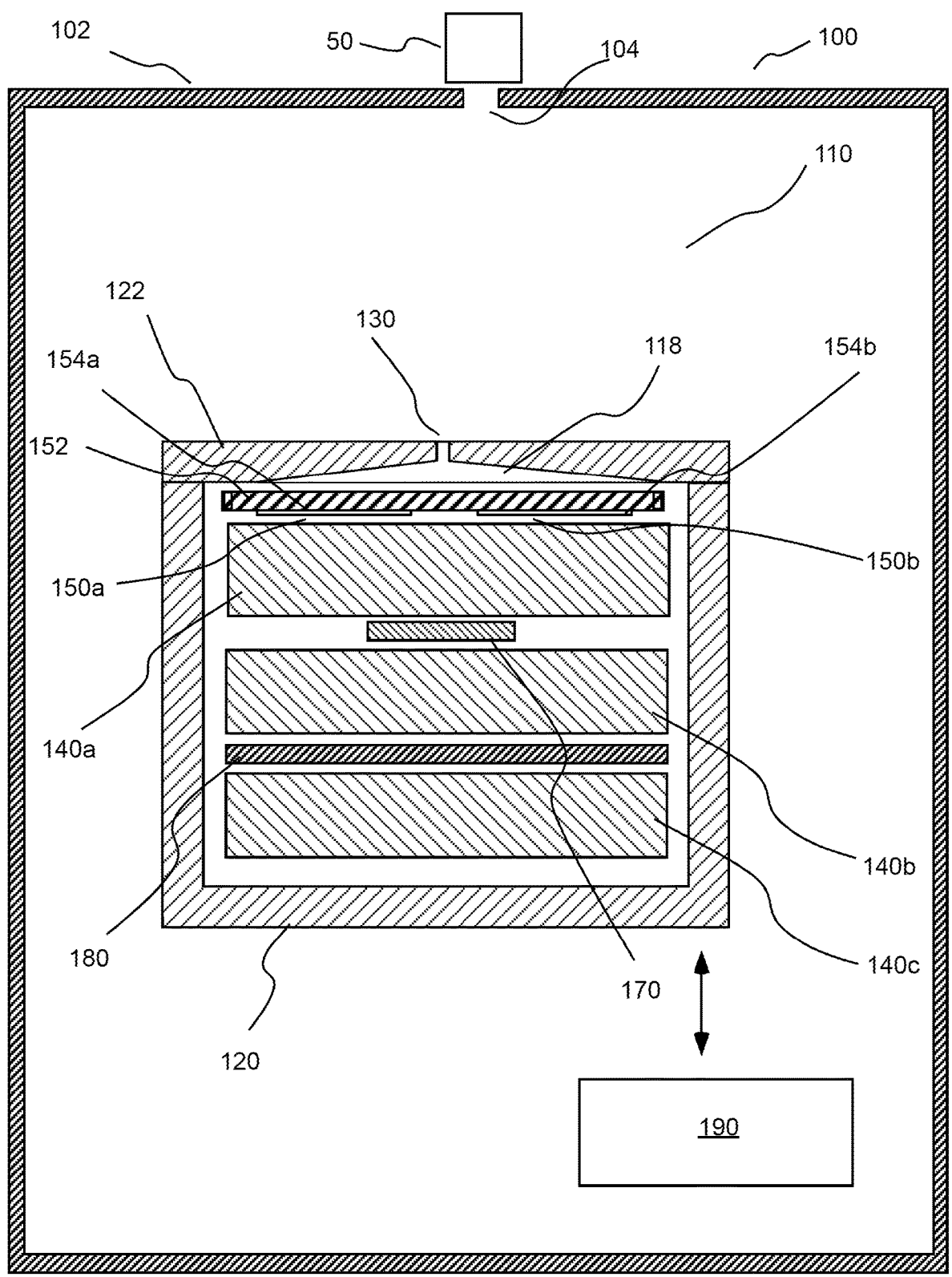
FIG. 2A illustrates a schematic, cross-sectional view of an embodiment of a system or instrument including at least one sensor which includes a first working electrode sensitive or responsive to an analyte and a second electrode sensitive or responsive to a driving force associated, for example, with the presence of exhaled breath.
Figure 2B:
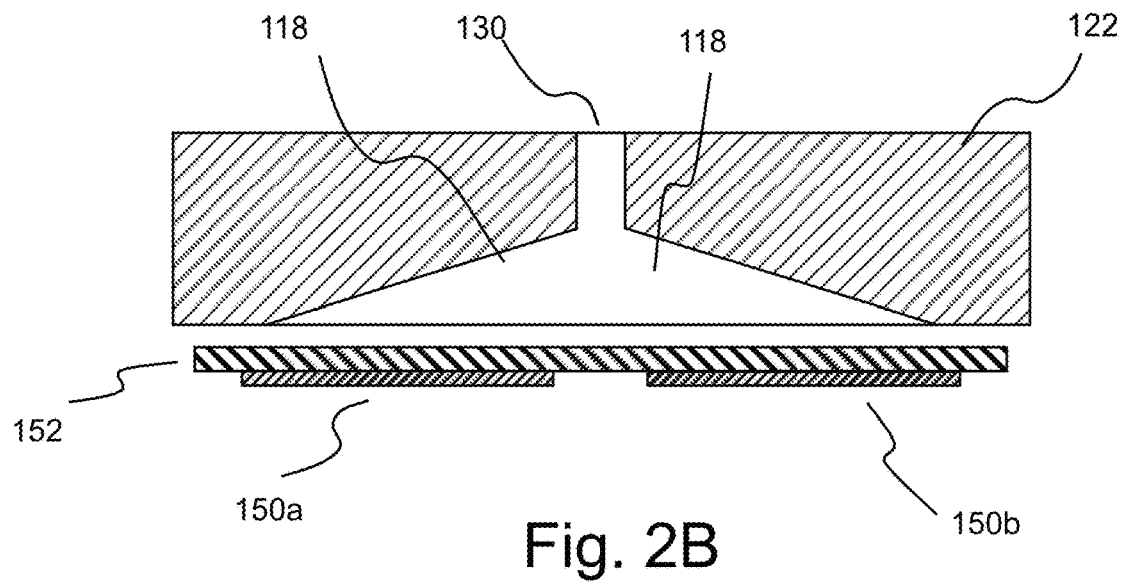
FIG. 2B illustrates an enlarged side, cross-sectional view of a portion of the sensor of FIG. 2A including a housing lid in which a gas inlet hole is formed to be in fluid connection with a gas diffusion space and a porous gas diffusion membrane, wherein the first working electrode and the second working electrode are formed on or attached to an interior side of the diffusion membrane.
Figure 2C:
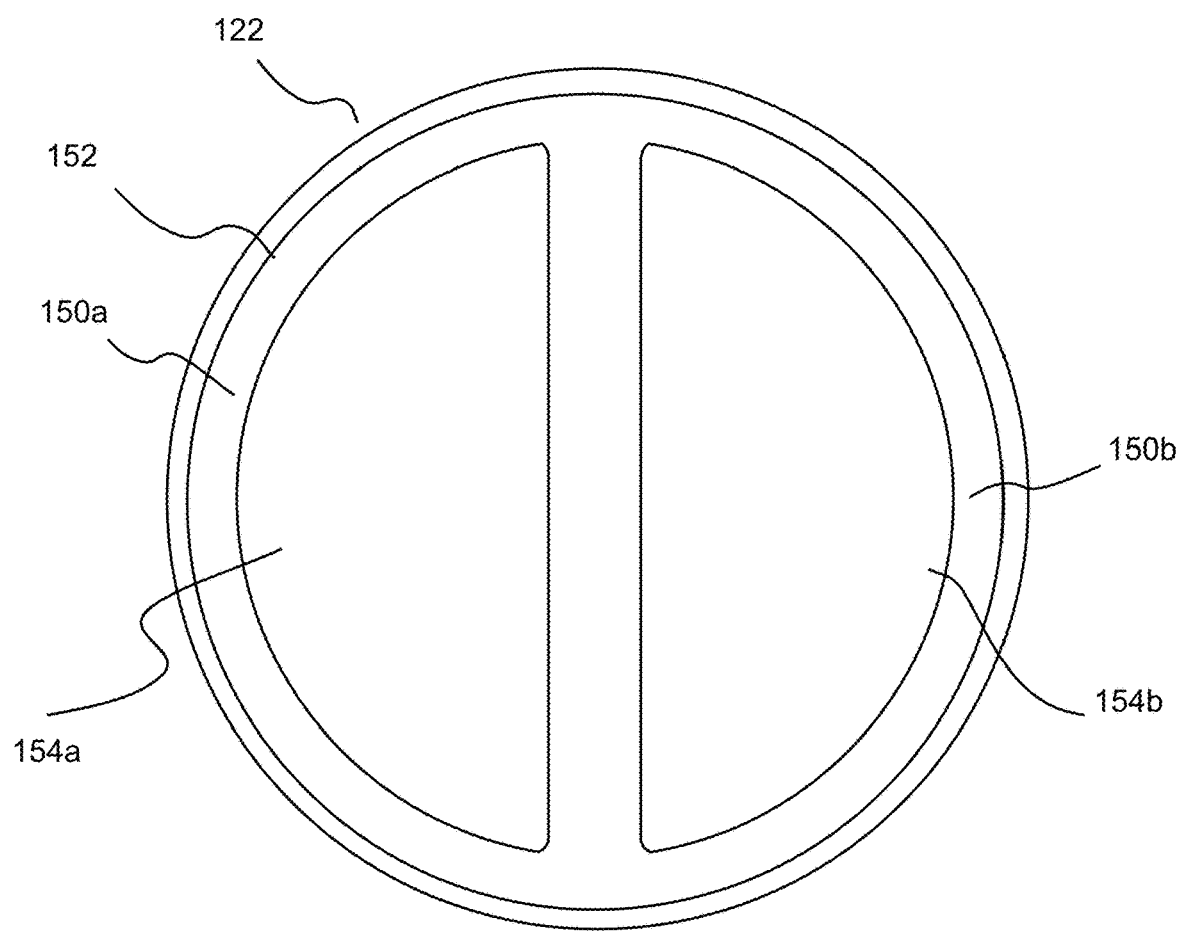
FIG. 2C illustrates a bottom view of the portion of the sensor illustrated in FIG. 2B.

FIGS. 2A through 2C illustrate a schematic diagram of an instrument or system 100 including at least one electrochemical sensor or sensor system 110. System 100 includes a system housing 102 including an inlet or inlet system 104 which places an interior of system housing 102 in fluid connection with the ambient environment. In the illustrated embodiment, electrochemical sensor system 110 includes at least one primary sensor responsive to at least one analyte gas. System 100 further includes at least one secondary sensor which is responsive to a driving force or variable change outside of system housing 102 in the vicinity of inlet 104 other than a change in concentration of the analyte gas or a simulant gas (that is, a gas other than the analyte gas to which the primary sensor is responsive) applied to system 100 from a container. A system 50 for creating such a driving force or variable change is illustrated schematically in FIG. 2A. System 50 may, for example, change the concentration of a gas, change humidity, change temperature, change pressure, change flow or diffusion etc. in the vicinity of system inlet 104. The secondary sensor is responsive to the driving force created by system 50. The response of the secondary sensor to the driving force is indicative of the state of the path or transport path between inlet 104 and the secondary sensor. In general, the transport path is the path via which a gas is transported from outside housing 102 (via inlet 104) to the secondary sensor (whether by, for example, diffusion or pumping). The transport path between inlet 104 and the secondary sensor and the transport path between inlet 104 and the primary sensor may, for example, be the same or similar and are exposed to generally the same conditions over the life of system 100. The secondary sensor may, for example, be positioned in close proximity to the primary sensor. The response of the secondary sensor to the driving forces provides an indication of the state of the transport between system inlet 104 and the primary sensor.

In a number of representative embodiments described herein, system 50 represents a person who exhales in the vicinity of inlet 104. In the case of exhaled breath, the driving force may be any one of (or more than one of), for example, a change in the concentration of a gas (for example, oxygen or carbon dioxide), a change in humidity, a change in temperature, a change in pressure, or a change in flow. The secondary sensor may thus include a gas sensor, a humidity sensor, a temperature sensor, a pressure sensor and/or a flow sensor. In the case that, for example, the secondary sensor is a humidity sensor, a temperature sensor, a pressure sensor or a flow sensor, system 50 need not be a person who exhales in the vicinity of system inlet 104. System 50 may, for example, be any system or device suitable to create a change in humidity, a change in temperature, a change in pressure, or a change in flow. The degree of change in the variable of interest may, for example, be controlled to monitor for a corresponding response of the secondary sensor. In the case of a change in temperature, system 50 may, for example, include a heating element. In the case of a change in pressure or a change in flow, system 50 may, for example, include a small, manually operated air pump such as a bellows.

In a number of representative embodiments hereof, the secondary sensor includes a gas sensor responsive to the concentration of a gas which is changed by exhalation in the vicinity of system inlet 104. In several such embodiments, sensor 110 includes a housing 120 having a gas inlet 130 (formed in a lid 122 of sensor housing 120) for entry of analyte gas and human breath into sensor 110. In the illustrated embodiment, inlet 130 is in fluid connection with a gas diffusion volume or space 118. Electrolyte saturated wick materials 140a, 140b and 140c separate a first working electrode 150a (responsive to the presence of analyte gas) and a second working electrode 150b (responsive to the presence of human breath) from reference electrode(s) 170 and counter electrode(s) 180 within sensor 110 and provide ionic conduction therebetween via the electrolyte absorbed therein. First working electrode 150a, reference electrode 170 and counter electrode 180, in cooperation with electrolyte saturated wick materials 140a, 140b and 140c form a portion of the primary sensor. Second working electrode 150b, reference electrode 170 and counter electrode 180, in cooperation with electrolyte saturated wick materials 140a, 140b and 140c form a portion of the secondary sensor. Electronic circuitry 190 as known in the art is provided, for example, to maintain a desired potential between working electrodes 150a and 150b and reference electrode(s) 170, to process an output signal from sensor 110 and to connect/communicate with other components of system 100 (including, for example, one or more displays, communication systems, power supplies etc.).

In the illustrated embodiment, first working electrode 150a and second working electrode 150b are located to be generally coplanar within sensor housing 120. In the illustrated embodiment, first working electrode 150a is formed by depositing a first layer of catalyst 154a on a diffusion membrane 152 (using, for example, catalyst deposition technique known in the sensor arts). Second working electrode 150b is also formed by depositing a second layer of catalyst 154b on diffusion membrane 152 (using, for example, catalyst deposition techniques known in the sensor arts). Methods of fabricating electrodes on diffusion membranes are, for example, described in U.S. Patent Application Publication No. 2011/0100813. Catalyst layers 154a and 154b may or may not be formed using the same electrocatalytic material. It is immaterial whether second gas diffusion or working electrode 150b is operated as an anode or cathode with respect to the operation of first gas diffusion or working electrode 150a.

Figure 3A:
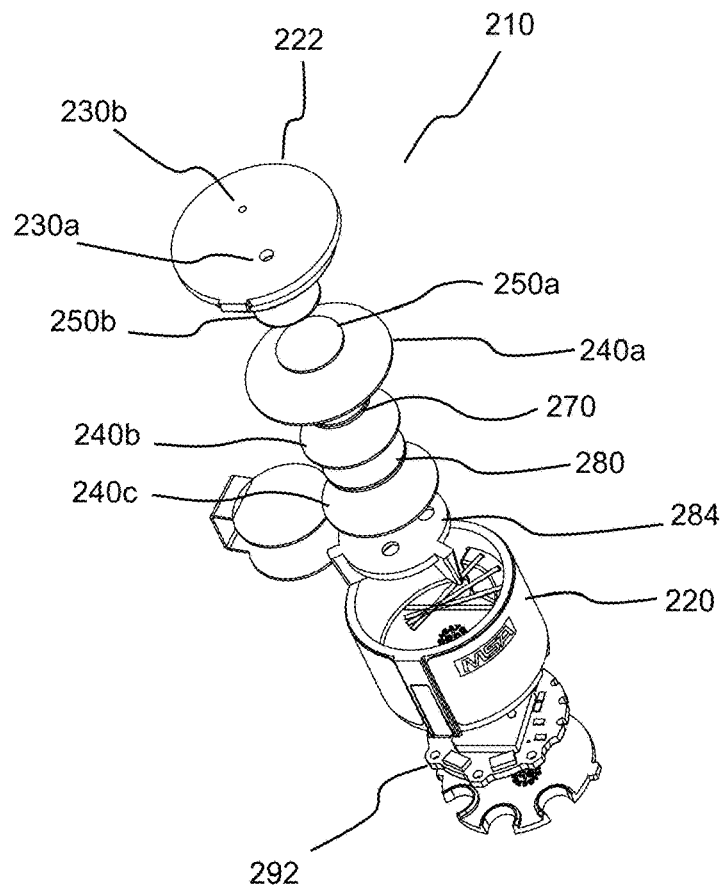
FIG. 3A illustrates a perspective exploded view of another embodiment of a sensor including a first working electrode sensitive or responsive to an analyte and a second electrode sensitive or responsive to the presence of exhaled breath, wherein the first working electrode is formed on a first diffusion membrane and the second working electrode is formed on a second diffusion membrane.
Figure 3B:
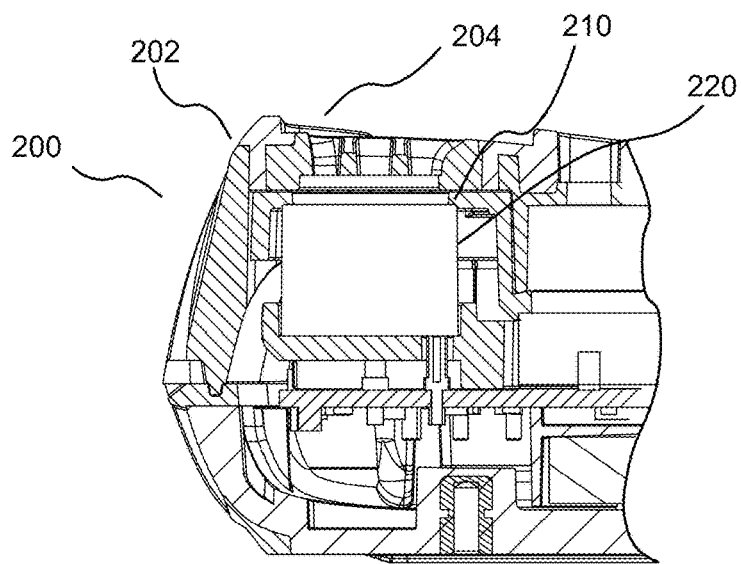
FIG. 3B illustrates a cross-sectional view of the sensor of FIG. 3A within an instrument or system housing.

FIGS. 3A through 3D illustrate an embodiment of a sensor 210 that is similar in design and operation to sensor 110. Like elements of sensor 210 are numbered similarly to corresponding elements of sensor 110 with the addition of 100 to the reference numbers of the elements of sensor 210. As illustrated in FIG. 3A, reference electrode 270, counter electrode 280 and electrolyte absorbent wicks 240a, 240b and 240c are supported within housing 220 via a support member 284. A printed circuit board 292 is connected to housing 220 and may form a part of the electronic circuitry of sensor 210.

Figure 3C:
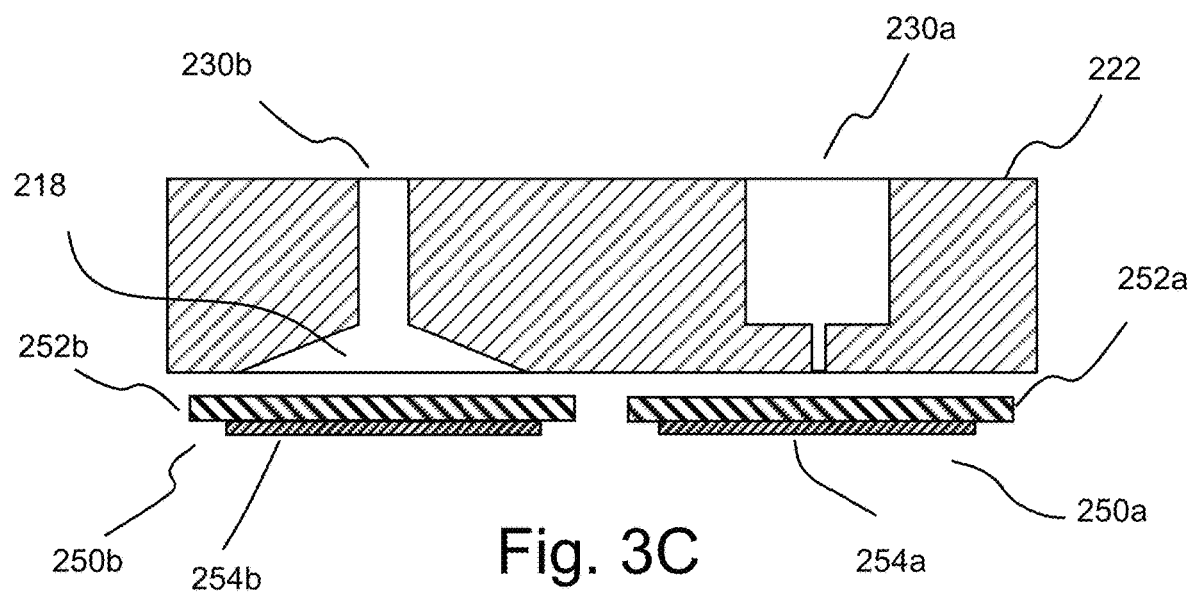
FIG. 3C illustrates an enlarged side, cross-sectional view of a portion of the sensor of FIG. 3A including a housing lid in which two gas inlet holes are formed, wherein each of the first working electrode and the second working electrode are in general alignment with one of the two gas inlet holes.
Figure 3D:
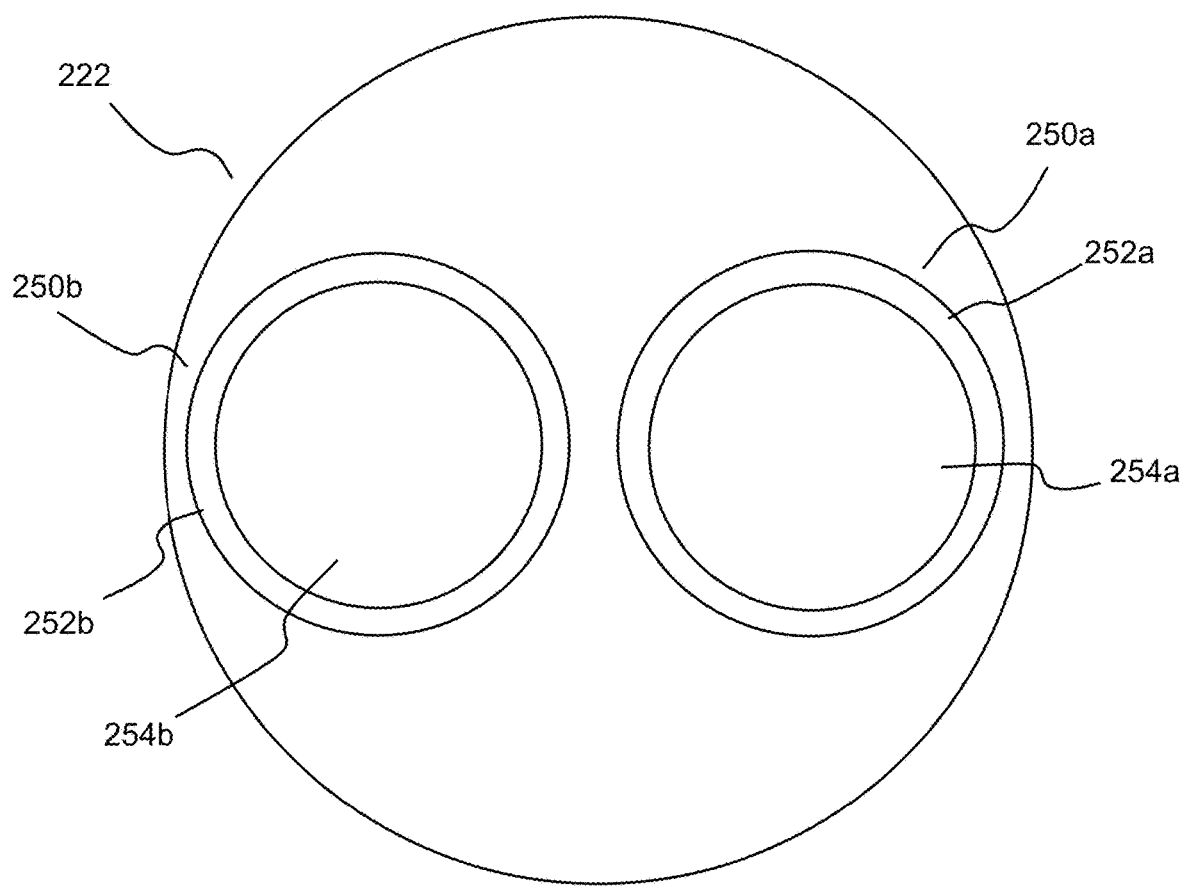
FIG. 3D illustrates a bottom view of the portion of the sensor illustrated in FIG. 3C.

As, for example, illustrated in FIGS. 3A and 3C, a housing lid 222 includes a first gas inlet 230a and a second gas inlet 230b. First gas inlet 230a and a second gas inlet 230b may, for example, be in fluid connection with an inlet system 204 (including, for example, one or more inlets) formed in a housing 202 of an instrument or system 200 (see FIG. 3B). First inlet 230a can, for example, be designed for use in connection with a first working electrode 250a for an analyte gas such as hydrogen sulfide. A first catalyst layer 254a of first working electrode 250a, which is deposited upon a first diffusion membrane 252a, may, for example, include iridium in the case that the analyte gas is hydrogen sulfide ($H_2S$). Second inlet 230b is designed for use in connection with the application of exhaled breath to second working electrode 250b. Second working electrode 250b is formed by deposition of a second catalyst layer 254b upon a second diffusion membrane 252b. Separate gas inlets 230a and 230b may, for example, be designed or optimized for passage of two different gases. In that regard, first gas inlet 230a may be optimized (for example, in dimension and/or shape) for the analyte gas of interest, while second gas inlet 230b may be optimized for a component of exhaled breath.

In the case of an aqueous electrolyte, the material(s) (which can be the same or different) of the gas diffusion membranes can be generally hydrophobic in nature to minimize or eliminate any flow of the aqueous electrolyte therethrough. In the case of a non-aqueous (for example, organic) electrolyte, the material of the gas diffusion membranes can be generally oleophobic in nature to minimize or eliminate any flow of the non-aqueous electrolyte therethrough. The material(s) can also be hydrophobic and oleophobic. Such materials are referred to as "multiphobic". The materials can also be chemically or otherwise treated to minimize or eliminate liquid electrolyte flow or leakage therethrough.

In general, the term "hydrophobic" as used herein refers to materials that are substantially or completely resistant to wetting by water at pressures experienced within electrochemical sensors (and thus limit flow of aqueous electrolyte therethrough). In general, the term "oleophobic" as used herein refers to materials that are substantially or completely resistant to wetting by low-surface tension liquids such as non-aqueous electrolyte systems at pressures experienced within electrochemical sensors (and thus limit flow of non-aqueous electrolyte therethrough). As used herein, the phrase "low-surface tension liquids" refers generally to liquids having a surface tension less than that of water. Hydrophobic, oleophobic, and multiphobic materials for use in electrodes are, for example, discussed in U.S. Pat. No. 5,944,969.

Gas diffusion membranes for use herein can, for example, be formed from polymeric materials such as, but not limited to, polytetrafluoroethylene (for example, GORETEX®), polyethylene or polyvinylidene fluoride (PVDF). Such polymeric materials can, for example, include a pore structure therein that provides for gas diffusion therethrough.

Figure 3E:
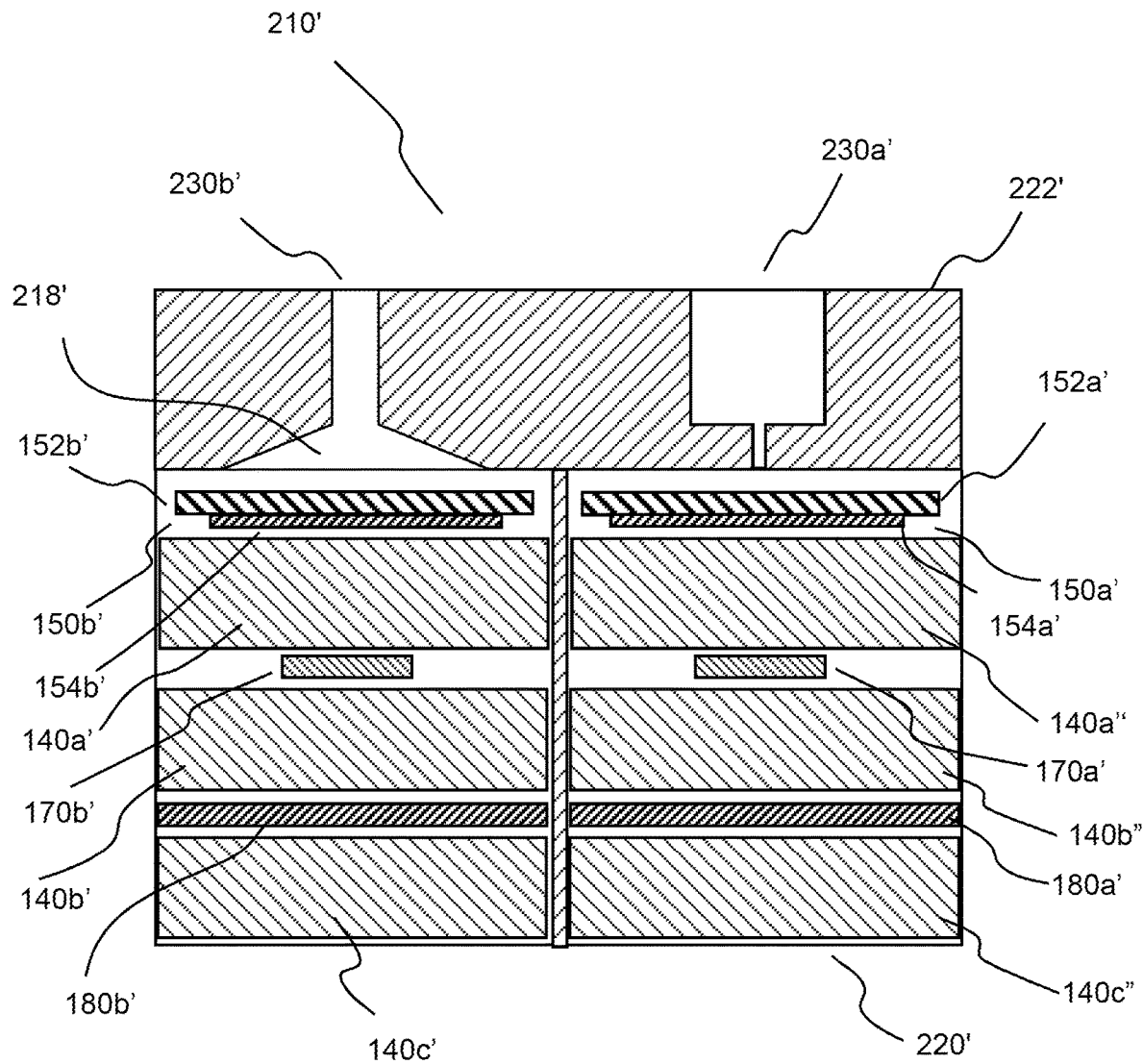
FIG. 3E illustrates a schematic, cross-sectional view of another embodiment of a sensor including a first working electrode sensitive or responsive to an analyte and a second electrode sensitive or responsive to the presence of exhaled breath, wherein the first working electrode is formed on a first diffusion membrane positioned in a first cell and the second working electrode is formed on a second diffusion membrane positioned in a second cell.

In sensors 110 and 210, first working electrodes 150a and 250a share a common electrolyte, a common counter electrode (180 and 280) and a common reference electrode (170 and 270) with second working electrodes 150b and 250b, respectively. In certain situations, depending, for example, upon the analyte gas to be detected and the associated electrochemistry, it may not be desirable or possible to have a common electrolyte, counter electrode and/or reference electrode. FIG. 3E illustrates another embodiment of a sensor 210', which is similar in operation and construction to sensors 110 and 210. Unlike sensors 110 and 210, in the embodiment of 210', first working electrode 150a' and second working electrode 150b' are positioned in separate cells within housing 220' which are not in fluid connection. In this manner, a different electrolyte can be used in connection with electrolyte saturated wick materials 140a', 140b' and 140c' than the electrolyte used in connection with electrolyte saturated wick materials 140a", 140b" and 140c". Likewise, reference electrode 170a' may be formed differently from reference electrode 170b', and/or counter electrode 180a' may be formed differently from counter electrode 180b'. In the illustrated embodiment, separate inlets 230a' and 230b' are formed in a common lid or cap 222' to be in fluid connection with first working electrode 150a' and second working electrode 150b', respectively.

Figure 3F:
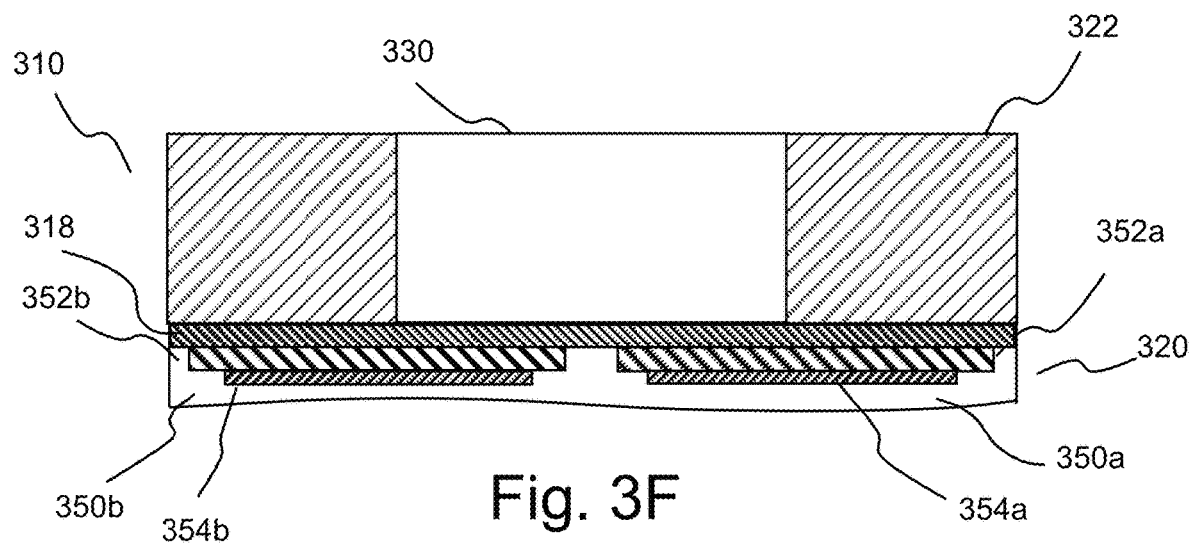
FIG. 3F illustrates a side, cross-sectional view of a portion of another embodiment of a sensor including a housing having an inlet in the form of an extending slot and a diffusion member in fluid connection with the inlet.
Figure 3G:
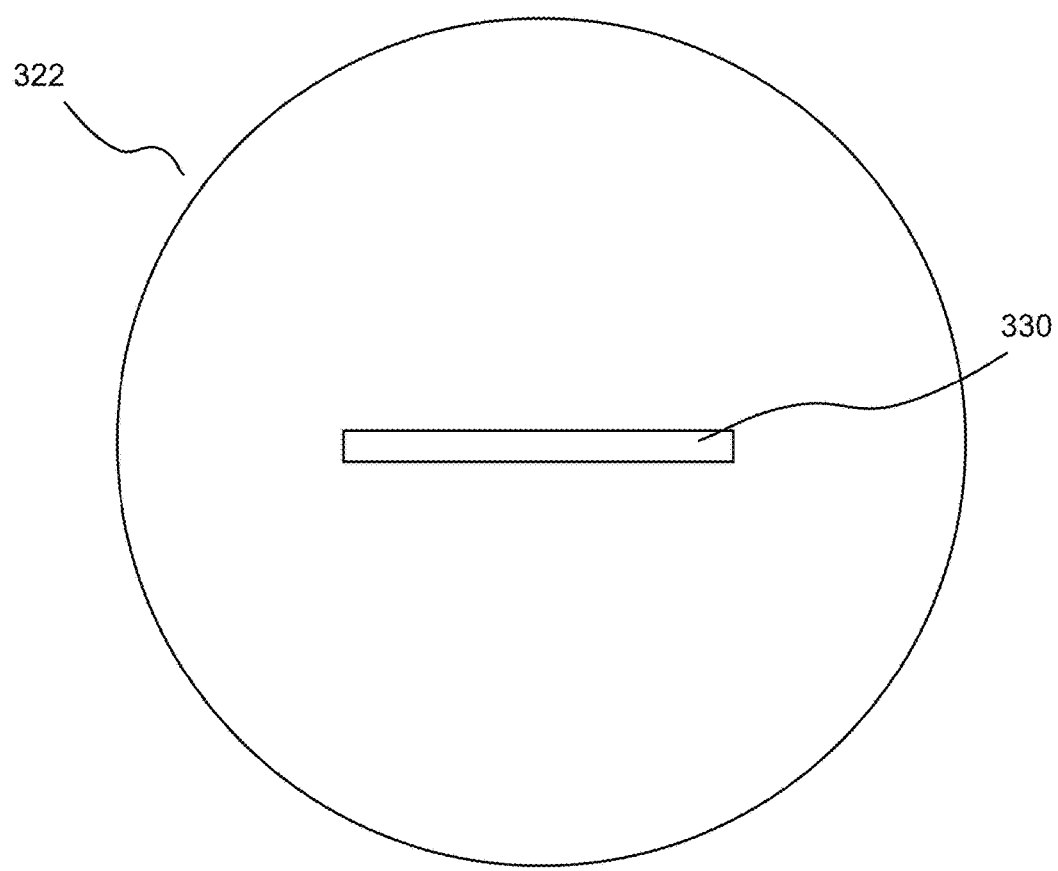
FIG. 3G illustrates a top view of the sensor of FIG. 3F.

FIGS. 3F and 3G illustrate another embodiment of a sensor 310, which is similar in operation and construction to sensors 110 and 210. Sensor 310 includes a housing 320 having a gas inlet 330 (formed in a lid 322 of sensor housing 320) for entry of analyte gas and human breath into sensor 310. In the illustrated embodiment, inlet 330 is formed as an extending slot in lid 322 and is in fluid connection with a gas diffusion member 318. Gas diffusion member 318 is, for example, formed from a porous polymeric material and provides for relatively quick lateral diffusion of gas to a first working electrode 350a (responsive to the presence of analyte gas) and a second working electrode 350b (responsive, for example, to the presence of human breath) to reduce response times of sensor 310. First working electrode 350a, second working electrode 350b, and remainder of the components of sensor 310, may, for example, be formed in the same manner as described above for working electrode 150a, second working electrode 150b and the remainder of the components of sensor 110. Gas diffusion member 318 may, for example, be stiffer in construction than diffusion membrane 352a of first working electrode 350a and diffusion membrane 352b of second working electrode 350b (upon which, catalyst layers 354a and 354b, respectively, are deposited). In addition to providing relatively quick lateral diffusion, gas diffusion member 318 may also protect diffusion membranes 352a and 352b from "pinching" as a result of mechanical compression.

Although the transport paths for first working electrodes 250a, 250a' and 350a and for second working electrodes 250b, 250b' and 350b of sensor 210, 210' and 310 are slightly different, all transport paths in a particular instrument experience generally the same environments and environmental conditions. Therefore, a challenge with a driving force such as, for example, exhaled breath and the measured response of second working electrodes 250b, 250b' and 350b thereto provides an indication of the functionality of all transport paths in the system or instrument.

In a number of embodiments described above, amperometric oxygen (or other) sensors operated in a diffusion mode are responsive to a driving force created in the vicinity of the inlet system (for example, exhaled breath) to test one or more transport paths. Such sensors may also be used in an instrument with a plenum or manifold which supplies a test gas (via pumping) to one or more sensors or sensing elements in fluid connection with the plenum. In this way, a single sensor responsive to a driving force such as exhaled breath provides information on the flow state of all transport paths (including, for example, membranes and membrane-protected or equipped sensors or sensing elements) in fluid contact with the plenum. This is especially true if the sensor responsive to the driving force such as exhaled breath is placed upstream of all the other sensors.

Figure 3H:
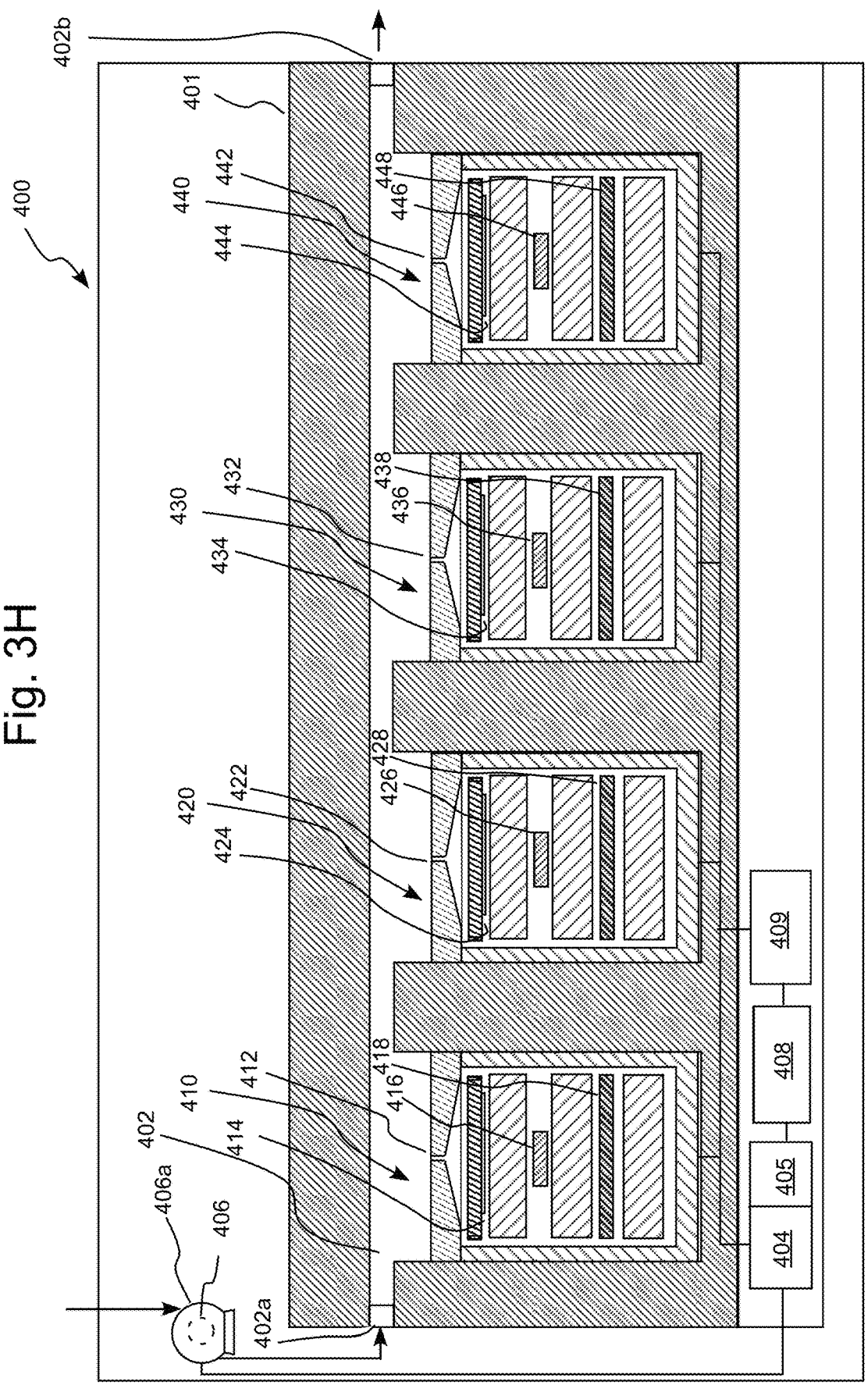
FIG. 3H illustrates a schematic view of a system or instrument including a plurality of individual sensors in fluid connection with a plenum through which gas to be tested is pumped to the sensors.

FIG. 3H illustrates an embodiment of an instrument or system 400 including a plurality of individual sensors 410, 420, 430 and 440 within a common housing. At least one of sensors 410-440 may, for example, be a non-analytical oxygen sensor as described above which is responsive to, for example, oxygen concentration change resulting, for example, from exhaled breath. In a number of embodiments, sensor 410, which is the first sensor in the flow path (that is, forced flow path), in system 400 is, for example, a non-analytical oxygen sensor. In such an embodiment, sensors 420, 430 and 440 may, for example, independently be a sensor for the detection of $H_2S$, $CO_2$, CO, $NO_2$, NO, $SO_2$, HCN, HCl, $NH_3$, $H_2$, $CH_4$, $C_2H_4$, $Cl_2$, EtOH or other analyte gases of interest. In a number of embodiments, at least one of sensors 420, 430 and 440 is an analytical oxygen sensor. Working electrodes 414, 424, 434, and 444, reference electrodes 416, 426, 436, and 446, counter electrodes 418, 428, 438, and 448, as well as the remaining components of sensors 410, 420, 430, and 440, respectively, may, for example, be formed in the manner described above. As is clear to one skilled in the art, system 400 may, for example, include fewer than or greater than four sensors.

As used herein, "analytical", "analytical electrode" and like terms refer to a working or sensing electrode with sufficient characteristics to provide an accurate or analytical indication of the concentration of the gas being sensed. Such characteristics include, for example, sufficient response range to provide accurate indications of test gas content over the desired range of concentration, long-term baseline stability, resistance to changes resulting from changes in environmental conditions, etc. "Non-analytical", "pseudo-analytical" and like terms refer to a working or sensing electrode with sufficient range and accuracy to be useful to accomplish an exhaled breath test or other flow path test as described herein. Stability and accuracy are not as important in this aspect as the exhaled breath test or other flow path test hereof occurs over a short time frame, and the response is entirely contained within that time frame. That is, there is no need to refer to an earlier established calibration event.

Referring again to FIG. 3H, each of sensor 410, 420, 430 and 440 is in fluid connection with a plenum 402. Test gas from the ambient environment is forced through plenum 402 (in the direction of the arrows of FIG. 3H—that is, entering plenum 402 via an inlet 402a and exiting plenum 402 via an exit 402b) via pump 406 including a pump motor 406a. Pump 406 is in fluid connection with the ambient atmosphere and with plenum 402. Sensors 410, 420, 430 and 440 as well as pump 406 may, for example, be in communicative connection with a control system which may, for example, include a processor system 404 (including, for example, one or more microprocessors) and/or circuitry for control thereof and data collection/processing. Processor system 404 is, for example, in communicative connection with a memory system 405. System 400 further includes at least one power source 408 (for example, one or more batteries). System 400 may also include at least one user interface system 409 in communicative connection with processor system 404 and memory system 405 to provide information to a user. User interface system 409 may, for example, include a display for visual signals. Information may also be provided via user interface system 409 via audible, tactile and/or olfactory signals.

As described above, in a number of embodiments, sensor 410 is a non-analytical oxygen sensor and one of sensors 420, 430 and 440 may be an analytical oxygen sensor. The output of the analytical oxygen sensor in ambient air (20.8 vol-% oxygen) provides an independent check of the health or state of function of system 400. Such an analytical oxygen sensor may, for example, be used in any embodiment of systems hereof.

Figure 3I:
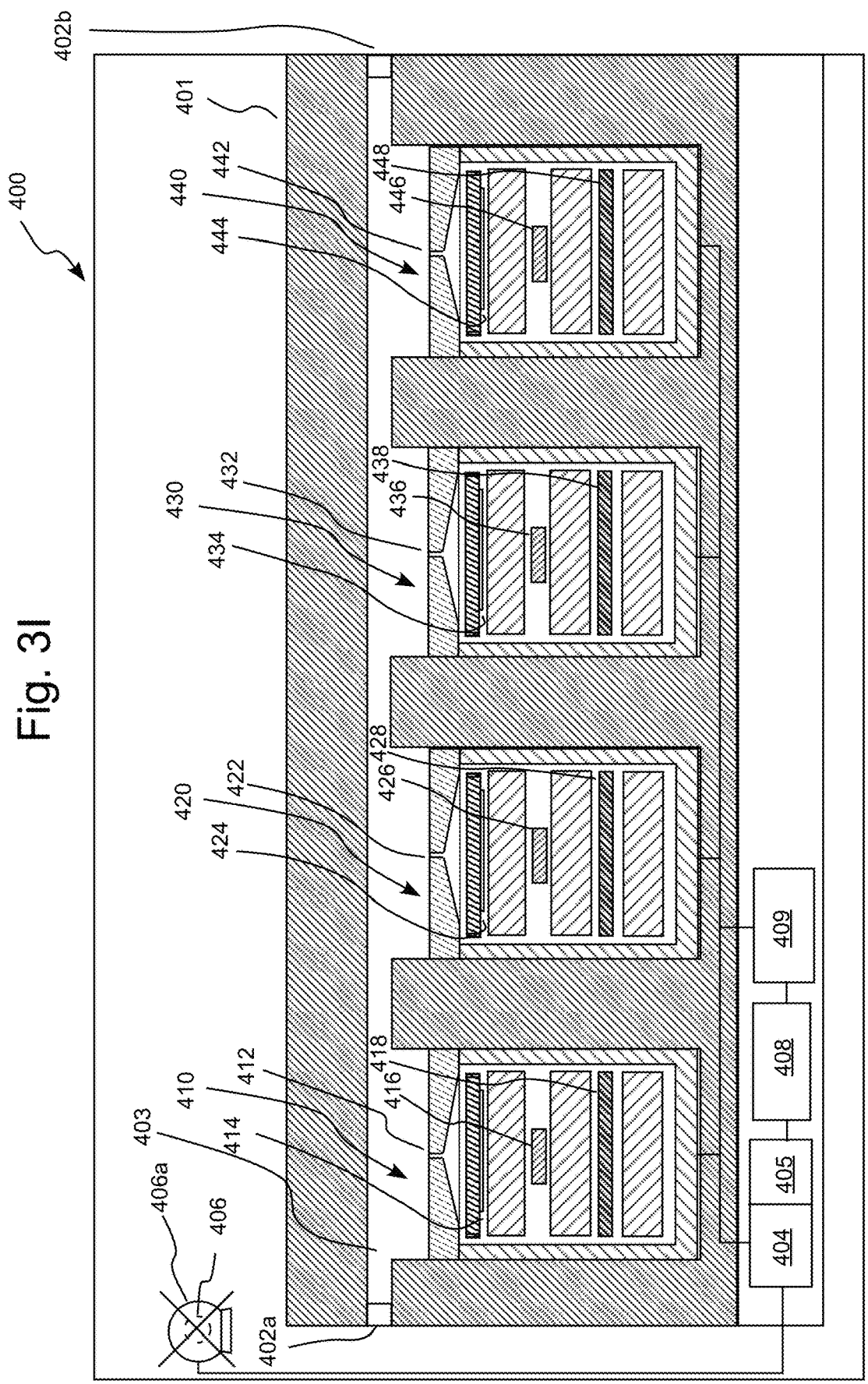
FIG. 3I illustrates a schematic view of a system or instrument including a plurality of individual sensors in fluid connection with a plenum through which gas diffuses to the sensors.

As illustrated in FIG. 3I, system 400 may also be operated in a diffusion mode when pump 406a is not powered. In other embodiments, a sensor housing with multiple separate sensors in fluid connection with a common gas inlet may be provided in which no pump is present. Once again, separate and distinct electrochemical cells within a common housing including, for example, at least one sensor responsive to oxygen provides a flow check or transport path functionality check as described herein, wherein individual sensors may be formed without the design restriction of common components (as, for example, illustrated in connection with FIG. 2A). As described above, sensor 410 may include oxygen sensitive chemistry (and components) described herein and other sensors 420, 430, 440 etc. may include entirely different sensing chemistry (and components) such as those described in U.S. Pat. Nos. 5,944,969, 5,667,653, and elsewhere.

Figure 3J:
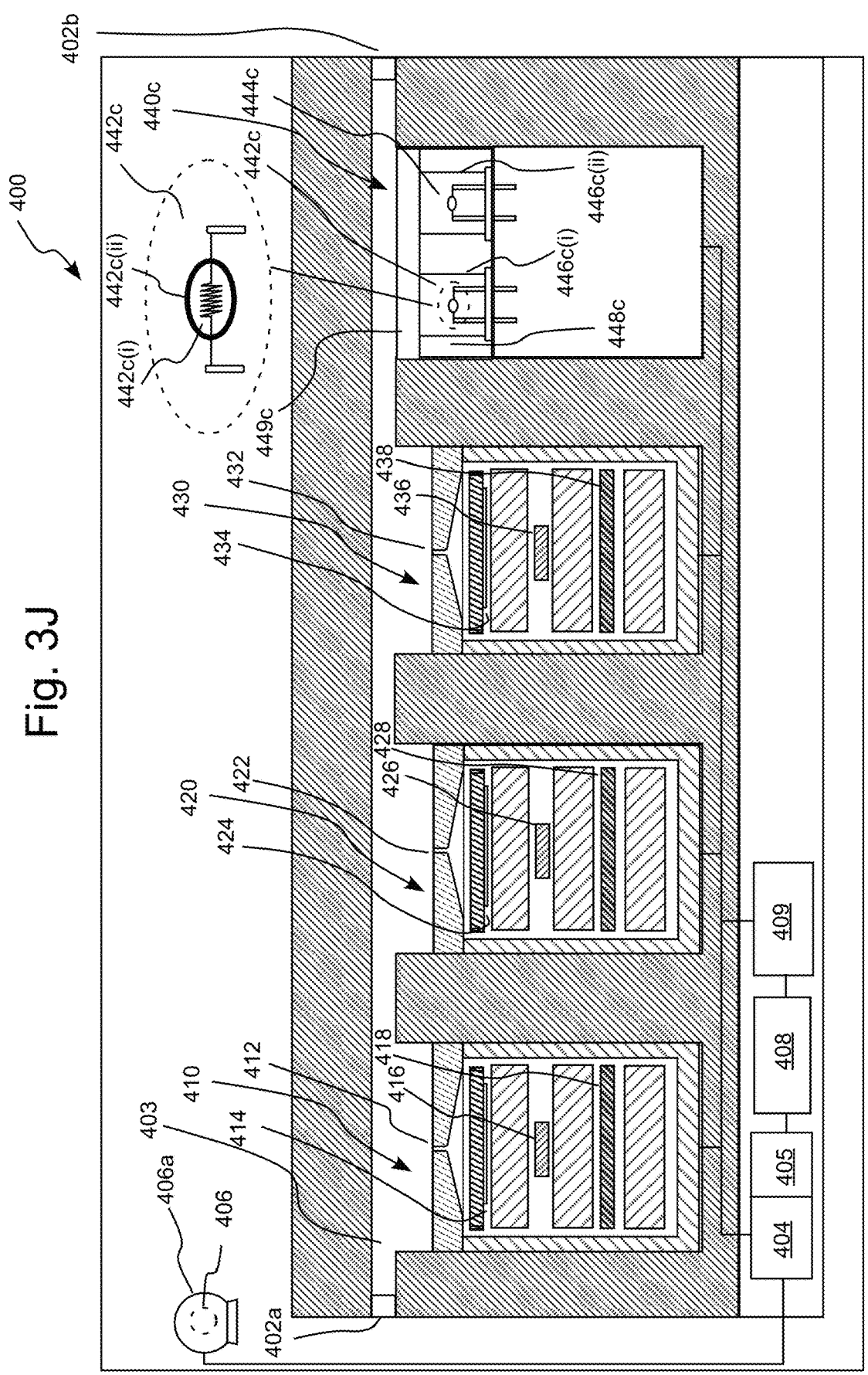
FIG. 3J illustrates a schematic view of a system or instrument including a plurality of individual sensors in fluid connection with a plenum or manifold through which gas to be tested is pumped to or diffused to the sensors, wherein at least one of the sensors is a combustible gas sensor.

FIG. 3J illustrates another embodiment of instrument or system 400 (which may operate in a forced flow or pumped mode and/or in a diffusion mode). In the embodiment of FIG. 3J, system 400 includes one or more electrochemical sensors 410, 420 and 430 and one or more combustible gas sensors represented by combustible gas sensor 440c. Catalytic or combustible (flammable) gas sensors have been in use for many years to, for example, prevent accidents caused by the explosion of combustible or flammable gases. In general, combustible gas sensors operate by catalytic oxidation of combustible gases. As illustrated in FIG. 3J, combustible gas sensor 440c includes a sensing element 442c, which includes a heating element such as a platinum heating element wire or coil 442c(i) encased in a refractory (for example, alumina) bead 442c(ii). Bead 442c(ii) is impregnated with a catalyst (for example, palladium or platinum) to form active or sensing element 442c, which is sometimes referred to as a pelement, pellistor, or detector. A detailed discussion of pelements and catalytic combustible gas sensors which include such pelements is found, for example, in Mosely, P. T. and Tofield, B. C., ed., *Solid State Gas Sensors*, Adams Hilger Press, Bristol, England (1987). Combustible gas sensors are also discussed generally in Firth, J. G. et al., *Combustion and Flame* 21, 303 (1973) and in Cullis, C. F., and Firth, J. G., Eds., *Detection and Measurement of Hazardous Gases*, Heinemann, Exeter, 29 (1981).

Sensing element 442c may react to phenomena other than catalytic oxidation that can change its output (i.e., anything that changes the energy balance on the bead) and thereby create errors in the measurement of combustible gas concentration. Among these phenomena are changes in flow, ambient temperature, humidity, and pressure. To minimize the impact of secondary effects on sensor output, the rate of oxidation of the combustible gas may be measured in terms of the variation in resistance of sensing element or pelement 442c relative to a reference resistance embodied in an inactive, compensating element or pelement 444c. The two resistances are typically part of a measurement circuit such as a Wheatstone bridge. The output or the voltage developed across the bridge circuit when a combustible gas is present provides a measure of the concentration of the combustible gas. The characteristics of compensating pelement 444c are typically matched as closely as possible with active or sensing pelement 442c. Compensating pelement 444c, however, typically either carries no catalyst or carries an inactivated/poisoned catalyst.

Active or sensing pelement 442c and compensating pelement 444c can, for example, be deployed within wells 446c(i) and 446c(ii) of an explosion-proof housing section 448c and can be separated from the surrounding environment by a flashback arrestor, for example, a porous metal frit 449c. Porous metal frit 449c allows ambient gases to pass into housing section 448c but prevents ignition of flammable gas in the surrounding environment by the hot elements. Such catalytic gas sensors may be mounted in instruments such as instrument 400 which, in some cases, must be portable and, therefore, carry their own power supply 408. It may, therefore, be desirable to minimize the power consumption of a catalytic gas sensor.

Combustible gas sensor 440c may provide an additional (or an alternative) sensor which is responsive to a flow path test as described herein. As described above, combustible gas sensors are sensitive to changes in flow, ambient temperature, humidity, and pressure. Moreover, combustible gas sensors are also sensitive to the concentration of oxygen in the environment surrounding the sensing element. Multiple sensors (of the same or different types) which are responsive to one or more driving forces of a flow path test hereof may, for example, be positioned at various positions along one or more flow paths of a system hereof to provide improved data specificity during a flow path test.

In several studies of sensors hereof, sensors fabricated in the manner of sensor 210 hereof were studied wherein first gas diffusion or working electrode 250a was used to detect hydrogen sulfide ($H_2S$), while second gas diffusion or working electrode 250b was used to detect the oxygen component of exhaled breath. Sensors fabricated in the manner of, for example, sensor 110, sensor 210', sensor 310 or sensor 410 would operate in the same or similar manner. In the specifically studied embodiments, first electrocatalyst layer 254a included iridium (Ir) metal. Second electrocatalyst layer 254b included platinum (Pt) metal, Other electrocatalysts suitable for reduction of oxygen may be used in second electrocatalyst layer 254b.

FIG. 4 illustrates the behavior sensor 210 when challenged with exhaled breath, followed by a mixture of 15 vol-% oxygen and 20 ppm hydrogen sulfide, followed by nitrogen. The $H_2S$ channel trace is the response of first working electrode 250a (designed to detect hydrogen sulfide), and the $O_2$ channel trace is the response of second working electrode 250b (designed to detect the oxygen component of exhaled breath). As illustrated, second working electrode 250b responds to the decreased oxygen content of exhaled breath which occurs at approximately the 50 second mark in the graph. A mixture of 15 vol-% oxygen and 20 ppm hydrogen sulfide was applied at approximately 100 seconds. Each of first working electrode 250a and second working electrode 250b responded appropriately to this challenge gas. Finally, nitrogen was applied at 250 seconds. Upon application of nitrogen, second working electrode 250b (designed for the detection of oxygen) responded appropriately to the challenge gas.

The response of second working electrode 250b to exhaled breath as shown in FIG. 4 may, for example, be used to determine that the transport paths (including gas diffusion members and/or membranes) of a portable gas detection instrument are, for example, not compromised by dust, vapors, and/or liquid. That is, based on the response of second working electrode 250b to the decreased oxygen concentration of exhaled breath, it can be determined that there is appropriate flow through all gas diffusion members (for example, gas diffusion membranes 252a and 252b), whether they are part of sensor 210 itself or part of the overall instrument. This gas response, when combined with, for example, an internal sensor electronic interrogation signal (such as that described in U.S. Pat. No. 7,413,645), may be used to provide a check of both the internal conductive condition of an amperometric electrochemical sensor (or other sensor) and any gas transport path(s) (including, for example, associated gas diffusion membranes), whether part of the sensor cell itself or part of the overall instrument. In this manner, a test similar in overall result to a bump test is accomplished without the use of expensive and potentially hazardous calibration gas and equipment associated therewith.

In a number of embodiments hereof for use in connection with an exhaled breath test or bump check, an amperometric oxygen (or other gas) sensing element is disposed within, for example, an amperometric toxic (or other) gas sensor for detecting an analyte of interest. In a number of the embodiments described above, both an analyte gas sensing working electrode and the oxygen sensing electrode are conventionally fabricated as gas diffusion electrodes. In many cases, such gas diffusion electrodes include a high surface area electrocatalyst dispersed on a porous support membrane. In embodiments in which an amperometric gas sensor is used in systems hereof as a secondary sensor to test one or more transport paths, because the secondary sensor (for example, an oxygen sensor) is not used to present an analytical signal (that is, it may be a non-analytical sensor), there may be no need to use either a gas diffusion electrode or a high surface area electrocatalyst.

Figure 5A:
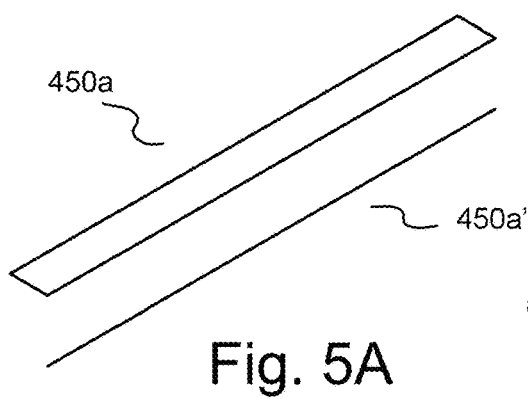
FIG. 5A illustrates a ribbon and a wire which may be used to form sensor elements in the systems hereof, which is adapted to measure a response to, for example, exhaled breath to test one or more transport paths of the system.
Figure 5B:
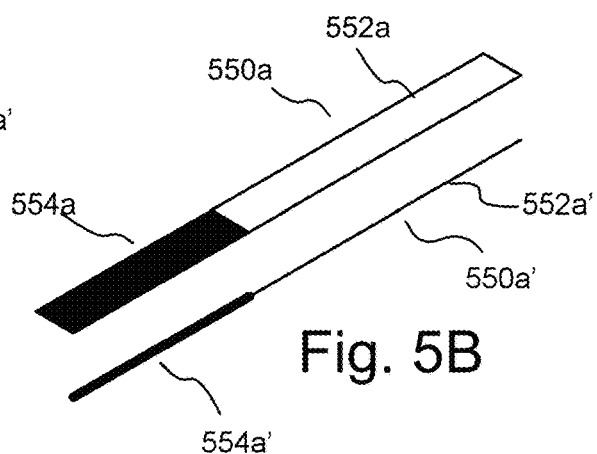
FIG. 5B illustrates sensor elements hereof including a conductive ribbon and a conductive wire upon which an electrocatalytic material is coated or immobilized.

For example, a conductor such as a contact ribbon or another conductive member, which are often used to carry an electrical signal from a gas diffusion electrode, may have sufficient surface area and electrocatalytic activity to be used as an oxygen, $CO_2$ or other gas sensitive electrode. For example, FIG. 5A illustrates a ribbon 450a and a wire 450a' which may be used to form a non-analytical sensor element in the systems hereof. Such ribbons or wires may, for example, be fabricated from an electrocatalytic material such as Platinum (Pt), Iridium (Ir), Gold (Au) or carbon (C). As illustrated in FIG. 5B sensor elements 550a and 550a' hereof may, for example, be a conductive ribbon 552a or a conductive wire 552a', respectively, upon which an electrocatalytic material 554a and 554a' (for example, Pt, Ir, Au, C etc.), respectively, is coated or immobilized. The material of ribbon 552a and wire 552a' may be the same or different from electrocatalytic material 554a and 554a' immobilized thereon.

Figure 5C:
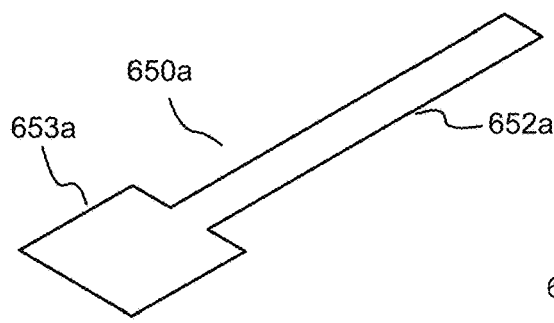
FIG. 5C illustrates a sensor element hereof including an extending ribbon having a rectangular end member which is wider than the extending ribbon.
Figure 5D:
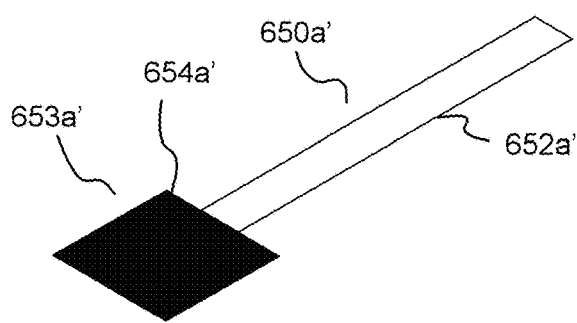
FIG. 5D illustrates the sensor element of FIG. 5C having an electrocatalytic material immobilized on the end member thereof.
Figure 5E:
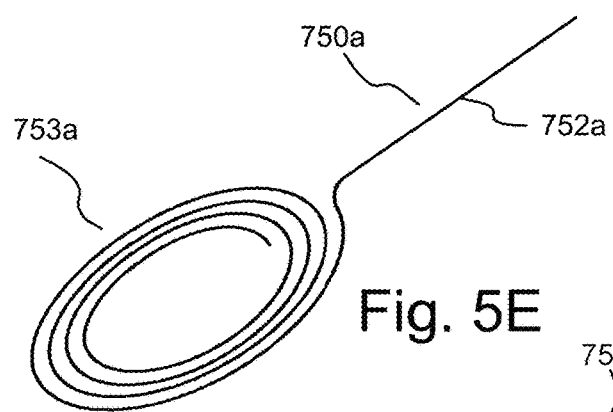
FIG. 5E illustrates a sensor element hereof including an extending wire having a spiraled section on an end thereof.
Figure 5F:
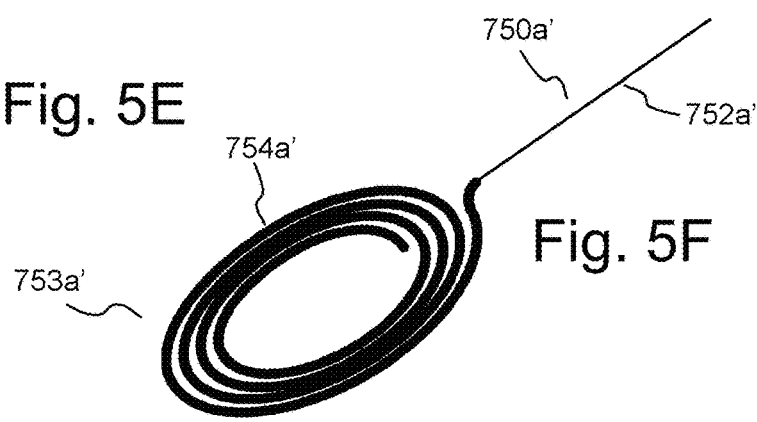
FIG. 5F the sensor element of FIG. 5E including an electrocatalytic material immobilized on the spiraled section thereof.

The sensor elements or electrodes hereof for testing transport paths may take a wide variety of two-dimensional or three-dimensional shapes. For example, FIG. 5C illustrates a sensor element 650a hereof including an extending ribbon 652a having a rectangular end member 653a which is wider than extending ribbon 652a to, for example, provide increased surface area per unit length as compared to a ribbon of the same length. Similarly, FIG. 5D illustrates a sensor element 650a' hereof including an extending ribbon 652a' having a rectangular end member 653a'. In the embodiment of FIG. 5D, an electrocatalytic material 654a' is immobilized on end member 653a'. FIG. 5E illustrates a sensor element 750a hereof including an extending wire 752a having a spiraled section 753a on an end thereof, which may, for example, provide increased surface area per unit length as compared to an extending wire of the same length. Similarly, FIG. 5F illustrates a sensor element 750a' hereof including an extending wire 752a' having a spiraled section 753a' on an end thereof. In the embodiment of FIG. 5F, an electrocatalytic material 754a' is immobilized on spiraled section 753a'. In the embodiments of FIGS. 5D and 5F, electrocatalytic materials 654a' and 754a' may be the same or different as the material upon which the electrocatalytic material is immobilized.

In the embodiments discussed above, a first electrode is used for sensing an analyte and a second electrode, formed separately from the first electrode, is used to, for example, detect oxygen concentration. In the representative example of a toxic gas sensor for detecting the analyte $H_2S$, for example, the toxic gas channel ($H_2S$, in that case) is fabricated to include the electrocatalyst iridium (Ir) and the oxygen-sensing electrode is fabricated to include the electrocatalyst platinum (Pt). Those electrocatalysts may, for example, be independently dispersed onto the same porous substrate, but in two distinct and different areas. The same or similar functionality may, for example, be achieved if mixtures of Pt and Ir are used. For example, such mixtures may be physical mixtures of high surface area catalytic powders or such mixtures may be alloys. In a number of embodiments, one electrocatalytic substance or material may, for example, be fabricated on top of another electrocatalytic substance or material in a two-step process.

Figure 6:
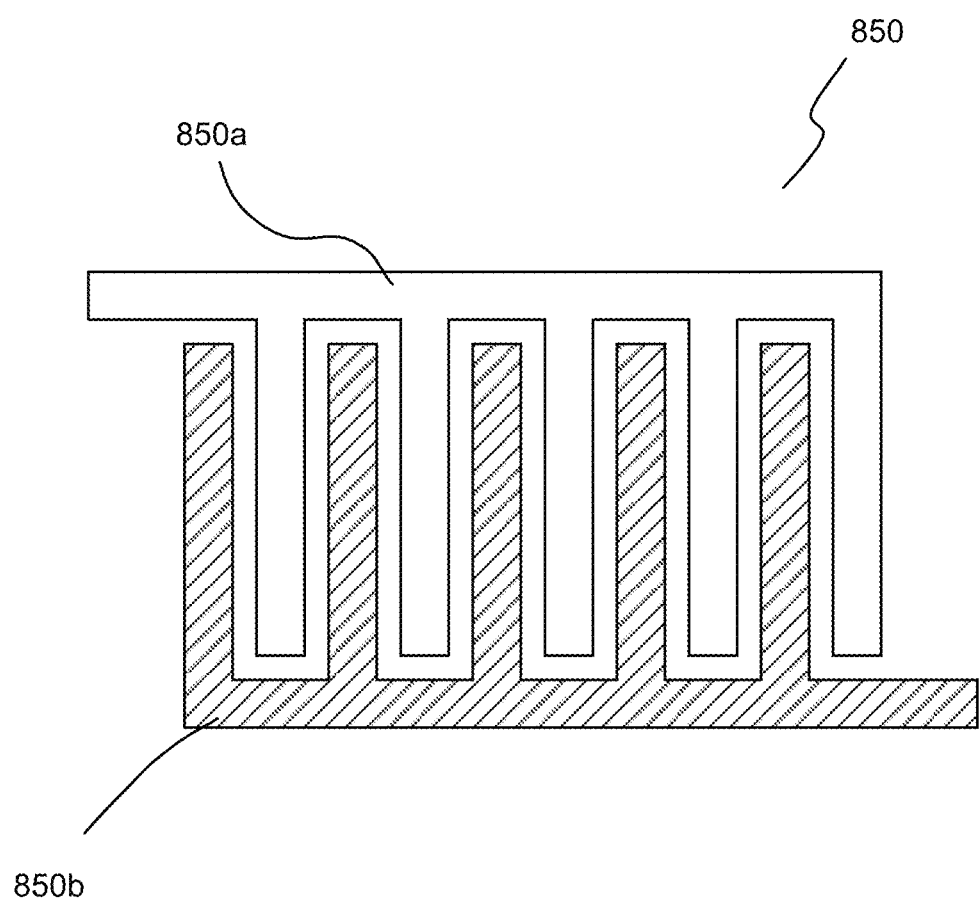
FIG. 6 illustrates an embodiment of an interdigitated electrode system hereof wherein a first branch of the electrode system includes a first electrocatalytic material and a second branch includes a second electrocatalytic material.

Moreover, the two electrocatalytic materials may, for example, be fabricated into an interdigitated electrode system. FIG. 6 illustrates an embodiment of an interdigitated electrode system 850 wherein a first branch 850a of electrode system 850 includes a first electrocatalytic material and a second branch 850b includes a second electrocatalytic material. The first and second electrocatalytic materials of the two branches or "fingers" 850*a* and 850*b* of electrode system 850 may, for example, be fabricated to include the same electrocatalytic substance (or mixture of substances) or to include different electrocatalytic substances.

Figure 7:
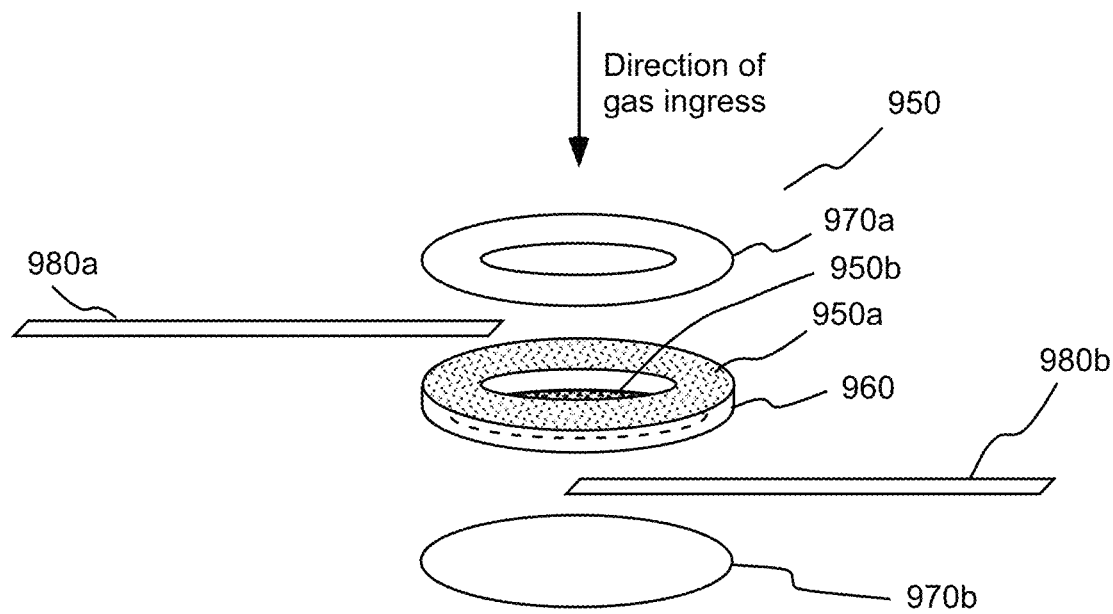
FIG. 7 illustrates an embodiment of an electrode system hereof wherein a first electrode and a second electrode are supported upon a gas porous disk, which is formed as an annulus.

In another embodiment of an electrode system 950 hereof illustrated in FIG. 7, a first electrode 950*a* and a second electrode 950*b* are supported upon a gas porous disk 960, which is formed as an annulus in the illustrated embodiment. Disk 960 may, for example, be fabricated from gas porous or permeable (that is, adapted to transport gas therethrough) polymer or another material that is inert in the electrolyte used in the sensor system. As described above, disk 960 serves as an electrode support onto which first working electrode 950*a* and secondary working electrodes 950*b* are fabricated, but on opposite sides of disk 960 as illustrated in FIG. 7. First or upper electrode 950*a* (in the orientation of FIG. 7) is formed as an annulus. Second or bottom electrode 950*b* is formed as a disk centered on the annulus of disk 960. Electrode system 950 further includes a first or upper electrolyte wick 970*a* and a second or lower electrolyte wick 970*b*. Electrode system also includes a first electrode current collector 980*a* and a second electrode current collector 980*b*.

The configuration of FIG. 7 may, for example, be vertically flipped or rotated 180° from its illustrated orientation and still function as intended. Many other shapes and configuration of electrodes are possible for use herein. Moreover, electrodes hereof may, for example, be stacked in multiple layers or other arrangements to produce sensors with a sensitivity for a multiplicity of target gases.

Figure 8A:
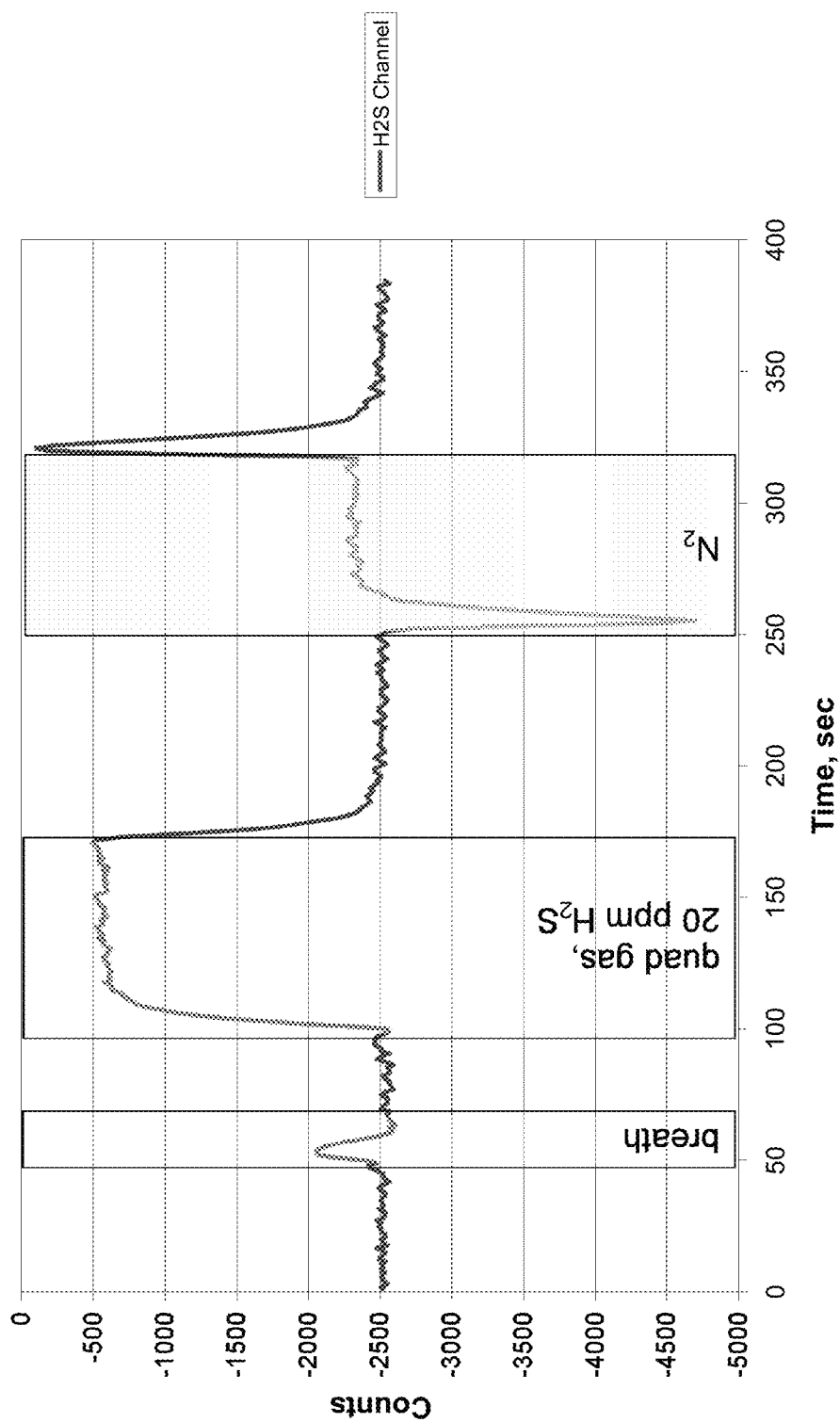
FIG. 8A illustrates the response of a representative embodiment of a single channel amperometric sensor hereof having a single electrode fabricated to include an electrocatalytic material that is responsive to an analyte, to exhaled breath and to nitrogen

In a number of embodiments hereof, a single working or sensing electrode, operated at a single bias potential, can be used that responds to both the analytical gas of interest (analyte) and to a another driving force (for example, a component of exhaled breath) to enable testing of one or more transport paths to the electrode(s) of the system. For example, in the representative sensor system described in FIG. 2, the $H_2S$ working electrode also responds to exhaled breath. The response of the working electrode to exhaled breath can be used to test the function of the transport path. FIG. 8A illustrates the response of a representative embodiment of a single channel amperometric sensor having a single electrode, operated at a single bias potential, fabricated to include an electrocatalytic material that is responsive to an analytical gas of interest or analyte ($H_2S$ in the representative example), to exhaled breath and to nitrogen. The electrode may be fabricated from a single electrocatalytic material, a physical mixture of electrocatalytic materials or an alloy of electrocatalytic materials. The data shown in FIG. 8A was collected by operating a hydrogen sulfide ($H_2S$) sensor at a constant bias potential of zero (0) mV versus an internal reference electrode. At this potential the working electrode (iridium (Ir), in this case) is sufficiently anodic to cause the Faradaic conversion of hydrogen sulfide to sulfur dioxide ($SO_2$), as is widely reported in the electrochemical literature. This can be seen in the graph of FIG. 8A, beginning around the 100 second mark, and represents the analytical signal of the sensor. Prior to the application of hydrogen sulfide, a driving force was applied to the sensor in the form of exhaled breath. The associated sensor response can be seen at about the 50 second mark in the graph. There is a small, positive excursion of the trace, upon application of exhaled breath, which was probably a result of the changes in the local humidity of the atmosphere in fluid contact with the sensor, caused by the high humidity (near 98% RH) in exhaled breath. Finally, a second driving force was applied to the sensor by the application of nitrogen ($N_2$) to the sensor at about 250 seconds. Again there is an excursion in the sensor signal, both for the application and removal of $N_2$. In this case, the signal originates from non-Faradaic rearrangement of ions near the electrode surface as a result of the sudden change in oxygen concentration. In both cases the application of a driving force to the face of the sensor, either by exhaled breath or by nitrogen, causes a sufficient, transitory change in the sensor signal to be used to assess the condition of the flow elements and flow path into the sensor. As described above, these effects are observed on a single sensor, with one working electrode, operated at a single, constant bias potential.

Figure 8B:
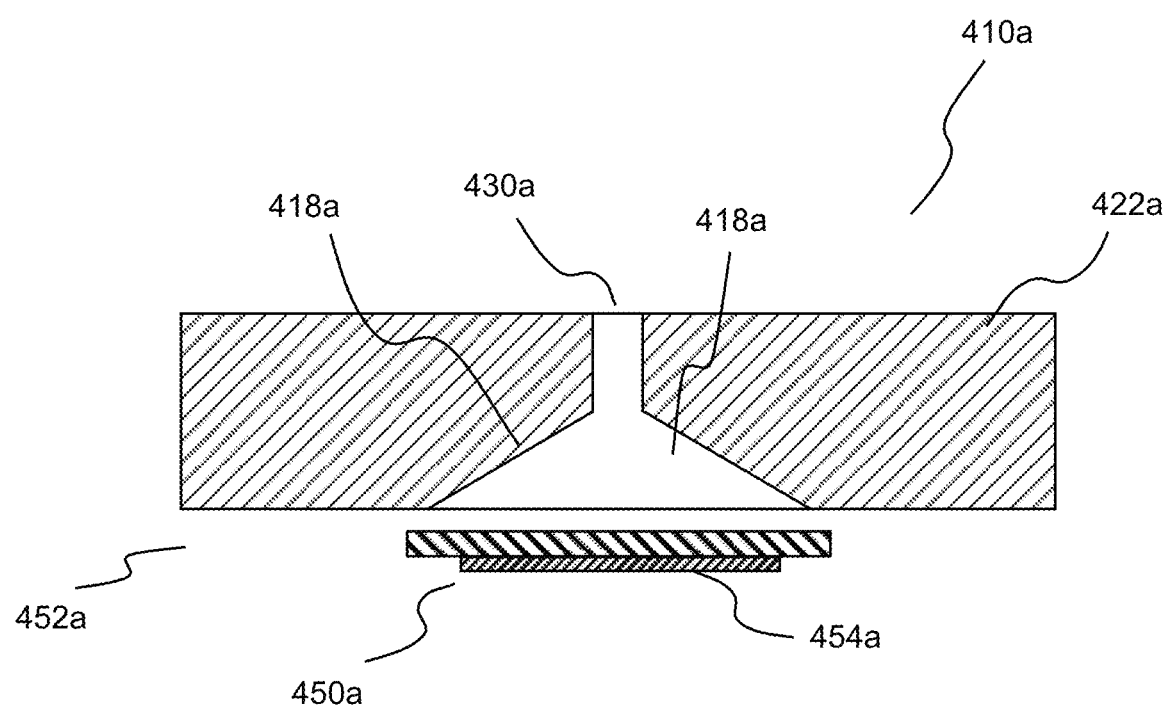
FIG. 8B illustrates an enlarged side, cross-sectional view of a portion of another embodiment of a sensor hereof including a housing lid in which a gas inlet hole is formed, wherein a single, multi-purpose electrode is in general alignment with the gas inlet hole, and wherein the electrode is operated at different biasing potentials.

FIG. 8B illustrates a portion of another embodiment of sensor 410*a* that is similar in design and operation to sensor 110. The remaining portion of sensor 410*a* may, for example, be substantially identical in design to sensor 110. Like elements of sensor 410*a* are numbered similarly to corresponding elements of sensor 110 with the numerical addition of 300 and the addition of the designation "a" to the reference numbers of corresponding elements of sensor 110. As illustrated in FIG. 8B, a housing lid 422*a* includes a gas inlet 430*a* which may, for example, be designed for use in connection with a working electrode 450*a* for an analyte gas such as hydrogen sulfide. A catalyst layer 454*a* of working electrode 450*a*, which is deposited upon a first diffusion membrane 452*a*, may, for example, include iridium in the case that the analyte gas is hydrogen sulfide ($H_2S$).

In a number of the embodiments discussed above, one channel, for example, a toxic gas channel for the measurement of $H_2S$ is fabricated to have a working electrode including an iridium catalyst, while a second channel includes an oxygen sensing electrode including a platinum catalyst. As described above, those catalysts may, for example, be independently dispersed on the same porous substrate in two distinct areas. In the embodiment of FIG. 8B working electrode 450*a* is operated at two bias potentials. At a first bias potential, working electrode 450*a* is active for oxidizing or reducing a target gas or analyte that sensor 410*a* is intended to detect (for example, $H_2S$). At a second bias potential, which is different from the first bias potential, working electrode 450*a* is active for oxidizing or reducing a component of exhaled breath utilized in an exhaled breath check as described above. The bias switching described above is controlled by the driving circuitry (for example, included upon a printed circuit board such as printed circuit board 292) and logic of sensor 410*a* and/or an instrument in which sensor 410*a* is included. Gas inlet 430*a* may, for example, be optimized (for example, in dimension and/or shape) for the analyte gas of interest and for a component of exhaled breath.

One of the more important operational aspects of using bias switching in a sensor with interrogation features as described above is that of the phenomenon colloquially known as "cookdown" to those skilled in the art of amperometric electrochemical gas sensors. Cookdown refers to the decay of large extraneous (that is, extraneous to the application of gas sensing) currents that flow between the working and counter electrodes of an amperometric gas sensor when the bias applied to the working electrode is suddenly changed (with respect to the either an internal reference electrode, in a three electrode cell, or with respect to a combination counter/reference electrode in a two electrode cell).

In the electrochemical arts, "Faradic current" usually refers to currents that flow in an electrochemical device when one substance is electrochemically converted to another, such as, for example, in an oxidation-reduction reaction, such as the reduction of oxygen ($O_2$) to water in an acidic electrolyte:

$$O_2 + 4H^+ + 4e^- \rightleftharpoons 2H_2O \quad\quad 1.1$$

Conversely, non-Faradaic currents are those currents that flow in an electrochemical cell when no substance is converted and are a result of only the rearrangement of ions very close to the electrode surface.

These phenomena may become important in considering the behavior of a sensor such as sensor 410a that uses single working electrode 450a, operated at two different bias potentials, to access the electrochemical reaction important for sensing the gas of interest and to access the potential region where, for example, oxygen (a component of exhaled breath) is reduced according to equation 1.1, above, to enable an exhaled breath test or flow check. In the example of a sensor with interrogation functionality described herein in which the intended target gas to be sensed is hydrogen sulfide ($H_2S$), one would typically use a high surface area iridium (Ir) electrocatalyst (Ir black) as the working electrode surface. At an applied potential of zero (0) mV versus an iridium/air (Ir|air) or platinum/air (Pt|air) pseudo-reference electrode (as is commonly employed in sensors to sense $H_2S$ including an Ir working electrode), $H_2S$ is oxidized to sulfur dioxide ($SO_2$) according to:

$$H_2S + 2H_2O \rightleftharpoons SO_2 + 6H^+ + 6e^- \quad\quad 1.2$$

The above reaction is a Faradaic reaction, and occurs only where there is $H_2S$ in the atmosphere supplied to the sensor (for example, sensor 410a). In the absence of $H_2S$, very small (near zero) non-Faradaic currents flow as a result of the continual rearrangement of ions very near the electrode surfaces. Such ionic rearrangements are a result of thermally induced Brownian motion. The phenomenon of cookdown becomes important when the potential or bias of the working electrode is suddenly changed.

As described above, the same high surface area Ir electrode (for example, working electrode 450a in the embodiment of FIG. 8B) may also be used to sense oxygen in the atmosphere supplied to the sensor (according to equation 1.1) if the potential of the working electrode is changed to approximately −600 mV (versus the internal reference electrode described above). This sudden change results in large negative currents (following the convention that reduction currents are presented as negative) that decay slowly over time to a steady state current that is indicative of the amount of oxygen present in the atmosphere sensed by the device. The decay over time is referred to as "cookdown." In the case described above, there are two sources of the cookdown current. The first source of current is the electrochemically induced rearrangement of ions very near the electrode surface as a result of the newly applied potential, which is a non-Faradaic current. The second source of current is the electrochemical reduction of oxygen. The oxygen that is electrochemically reduced includes oxygen that is dissolved in the electrolyte of the sensor. In that regard, until the step change in potential to −600 mV, the electrode was operated in a region where the conversion depicted in equation 1.1 did not occur. Therefore, over time, the electrolyte becomes saturated with dissolved oxygen. The electrochemically reduced oxygen also includes the oxygen being supplied to the working electrode from the atmosphere applied to the sensor. The resultant current is Faradaic current, resulting from the conversion of oxygen to water, regardless of the source of oxygen. The current resulting from reduction of oxygen dissolved in the electrolyte may be accounted for during an exhaled breath test.

Operated at a potential of −600 mV, a sensor with an interrogation functionality as described herein is able to undergo or perform some type of breath or flow check that involves the perturbation of delivery of oxygen to the sensor. This may, for example, be associated with the application of exhaled breath.

During operation, a sensor such as sensor 410a would be operated at −600 mV only during an exhaled breath or flow test/check. Its nominal operation would be at an applied potential of zero mV for the sensing of $H_2S$. However, upon the completion of the exhaled breath or flow test/check, the external operational circuitry of sensor 410a would suddenly return the applied bias of working electrode 450a to 0 mV. This bias potential change would induce large, transitory positive currents, until sensor 410a returned to its normal, near zero current in the absence of $H_2S$. The large, positive, transitory current would be the non-Faradaic cookdown of sensor 410a to its normal operating state. Such cookdown currents will occur every time the bias is switched to and from the region where sensor 410a would reduce oxygen, as is necessary for the exhaled breath or flow test/check.

Figure 8C:
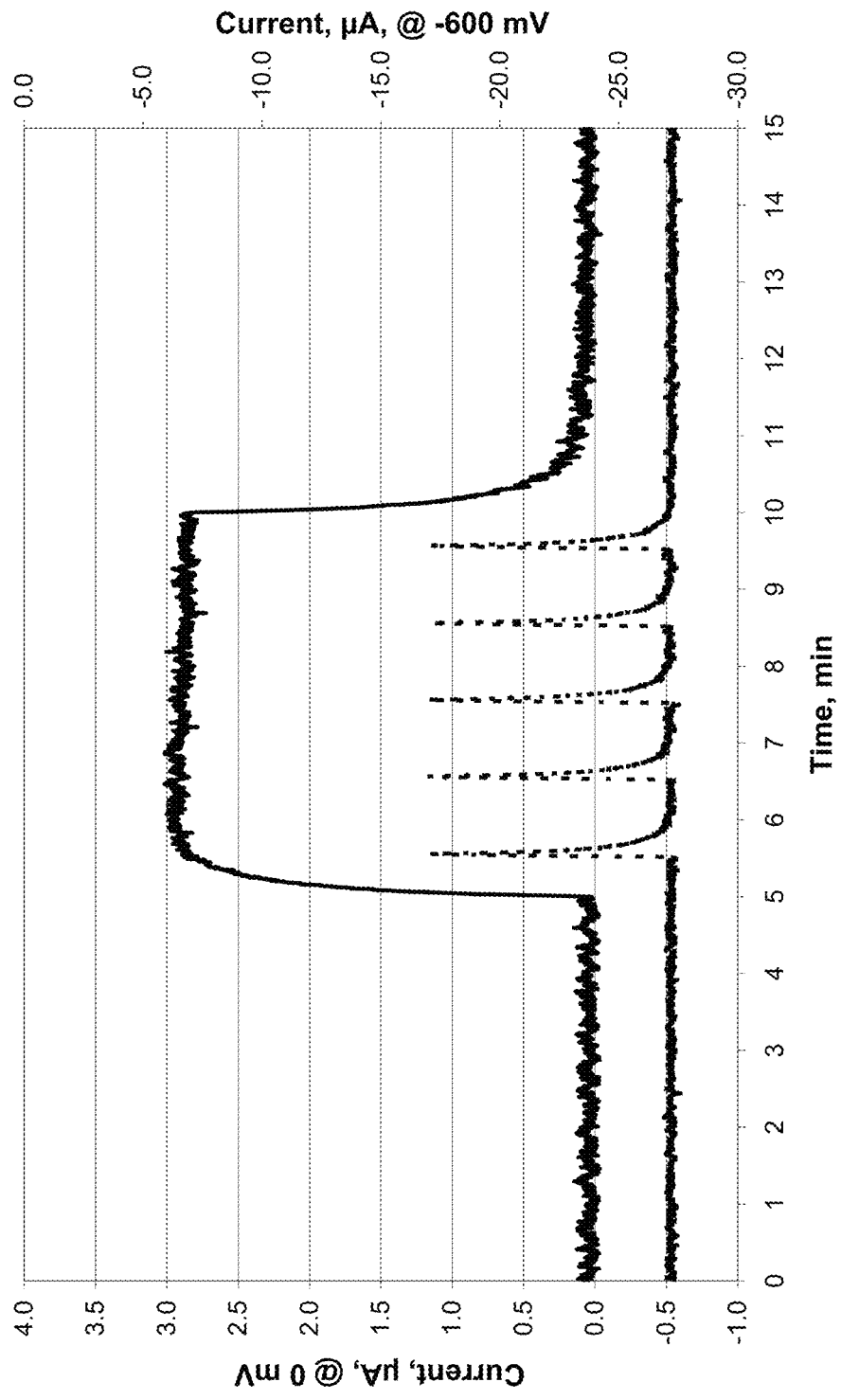
FIG. 8C illustrates data from the operation of a sensor including a working electrode operable to detect the analyte hydrogen sulfide at a first biasing potential and to act as a non-analytical, pseudo-electrode for detecting a change in oxygen concentration at a second potential.
Figure 8D:
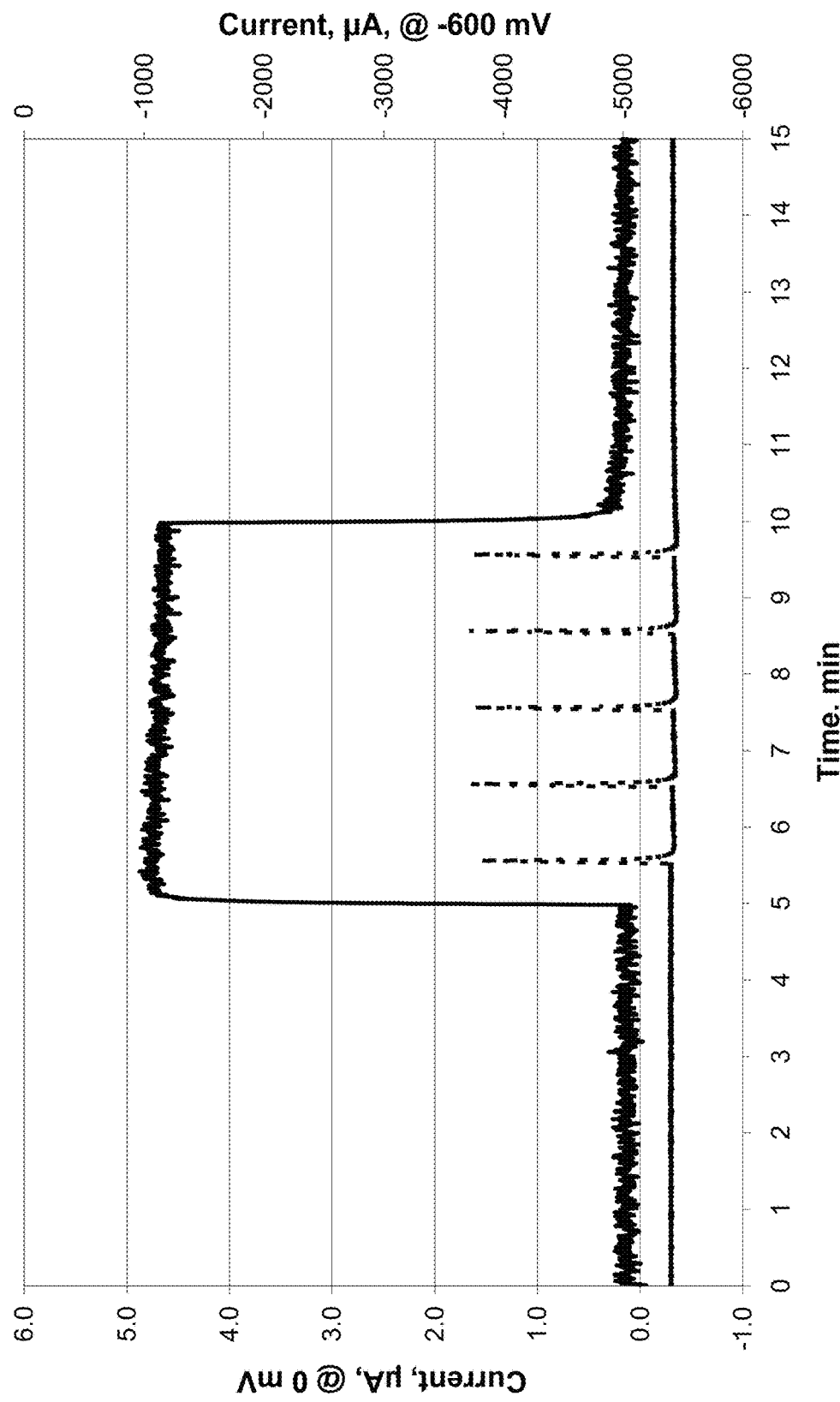
FIG. 8D illustrates data from the operation of a sensor including a working electrode operable to detect the analyte carbon monoxide at a first biasing potential and to act as a non-analytical, pseudo-electrode for detecting a change in oxygen concentration at a second potential.

FIGS. 8C and 8D provide data from examples of electrochemical sensors such as electrochemical sensor 410a in which a single working electrode is operated at two different bias potentials. As described above, the sensor is operated at a first bias potential for the analytical sensing of the analyte gas of interest, and at a second, different bias potential, for operation as a pseudo-electrode for oxygen. In this context, the term "pseudo-electrode" refers to a working electrode-bias potential combination that gives a sufficient response to indicate a change in the oxygen content of the atmosphere being sensed, but may not have the analytical sensitivity or range to be relied upon to provide an analytical or accurate indication of the oxygen content of the atmosphere. Thus, when operated as a pseudo-electrode, the working electrode may be operating as a non-analytical electrode as described above.

FIG. 8C provides an example of operation of a sensor for the detection of the analyte hydrogen sulfide at two different biasing potentials. As described above, the tested sensor utilized an iridium (Ir) working electrode, operated a two different potentials to accomplish both the analytical detection of hydrogen sulfide and to act as a pseudo-electrode for detecting a change in the oxygen content of the atmosphere being detected (such as, for example, during an exhaled breath check). In FIG. 8C, the upper, solid line represents the results of the application of 20 ppm $H_2S$ to the sensor with the Ir working electrode biased at 0 mV verses the internal Pt|air reference electrode, plotted against the left-hand, y-axis. The lower, broken-line trace represents the response of the same electrode, operated at −600 mV (versus the same internal reference electrode), plotted against the right-hand, y-axis to five consecutive 2.5 second applications of nitrogen. Referring to the broken line in FIG. 4B, operation of the Ir working electrode at −600 mV, in air (20.8 vol-% oxygen) resulted in a current, from the electrochemical reduction of oxygen in air, of approximately −27 µA. The 2.5 sec pulses of nitrogen (simulating oxygen reduction associates with, for example, an exhaled breath test as described herein) resulted in positive deflections of the oxygen baseline, sufficient in magnitude to act as an indication of the condition of the flow system flow path elements of the sensor.

FIG. 8D provides data from an experiment similar to that of FIG. 8C, but for a carbon monoxide sensor. In the sensor of the experiments of FIG. 8D, the working electrode was platinum (Pt). The upper, solid line sets forth the results of the application of 60 ppm CO to the Pt working electrode, biased at 0 mV against the internal Pt|air reference electrode, plotted against the left-hand, y-axis. The lower, broken line sets forth the results of the same working electrode, operated at −600 mV against the internal reference electrode, plotted against the right-hand, y-axis. In FIG. 8D, the current observed as a result of the reduction of oxygen from the atmosphere results in a steady state or baseline oxygen reduction current of approximately −5300 µA. The positive pulses in FIG. 8D were the result of five consecutive 2.5 second long pulses of nitrogen. The positive deflections observed in FIG. 4D were sufficient to assess the condition of the flow paths of the sensor.

Many other types of sensor may include a working electrode operated at two potentials as described above. For example, similar behavior is observed for a chlorine ($Cl_2$) or a chlorine dioxide ($ClO_2$) sensor utilizing a gold (Au) working electrode. Further, a sulfur dioxide ($SO_2$) sensor with either platinum or gold working electrodes could be operated in the same manner.

In a number of other embodiments of sensor systems hereof, two sensing or working electrodes are provided which include the same electrocatalytic material immobilized thereon. The electrodes can, for example, be fabricated in an identical manner. In such embodiments, the analyte gas and, for example, a gas of interest in exhaled breath are each electroactive on the electrocatalytic material. In a number of embodiments, the function of the two electrodes is alternated (for example, each time the user activates a breath check as described above). Referring to, for example, FIG. 6, the first and second electrocatalytic materials of the two branches or electrodes 850a and 850b of electrode system 850 would include the same electrocatalytic material. In a first instance of activation of the instrument including electrodes 850a and 850b, electrode 850a would be used as the working electrode for the target analyte gas and electrode 850b would be used to, for example, detect a component of exhaled breath (for example, oxygen). The next time the user activates the internal breath check (a second instance), the functions of electrodes 850a and 850b would be switched by the external circuitry and logic of the system or instrument including sensors 850a and 850b. That is, in the second instance, electrode 850b would be used as the working electrode for the target analyte gas and electrode 850a would be used to detect the component of exhaled breath. In this manner, alternatively, each electrode area would be calibrated against the target gas of interest and the electronic life and health checks described below would be periodically applied to each electrode. Such a system and methodology provides a greater amount of surveillance and surety to the test methodology. A detection or sensing element switching scheme which may be adapted for user herein is described in U.S. Patent Application Publication No. 2011/0100090, the disclosure of which is incorporated herein by reference.

The application of human breath to cause a perturbation in, for example, oxygen concentration as described herein is applicable, in most instances, to portable instrument applications, wherein a human user is available to provide a sample of exhaled breath to exercise the interrogation or test system of the sensor (as described above), thereby testing flow through the instrument and/or sensor inlet holes and membranes (that is, testing flow paths of the system). Analysis of oxygen concentration perturbation may also be extended to, for example, permanent sensing applications (in which a sensor is fixedly positioned for extended periods of time—typically until replacement), wherein there is no human user available to exhale breath into the instrument/sensor membranes. The instrument may, for example, be placed in a position which is not easily accessible by a human attendant.

Figure 9A:
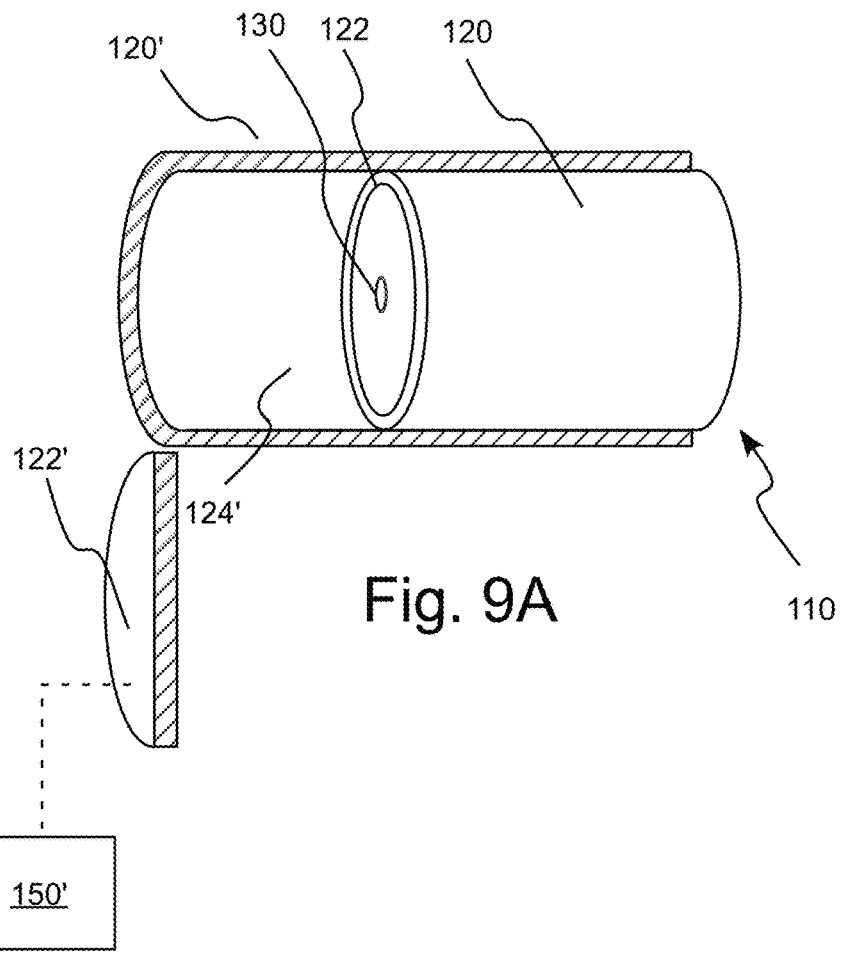
FIG. 9A illustrates a schematic, cross-sectional view of a portion of another embodiment of a system hereof in which oxygen in the atmosphere is used to test or interrogate a system via dynamic coulometric measurement, in which a volume in fluid connection with an oxygen sensor is in an open state wherein the sensor is in fluid connection with the ambient atmosphere.
Figure 9B:
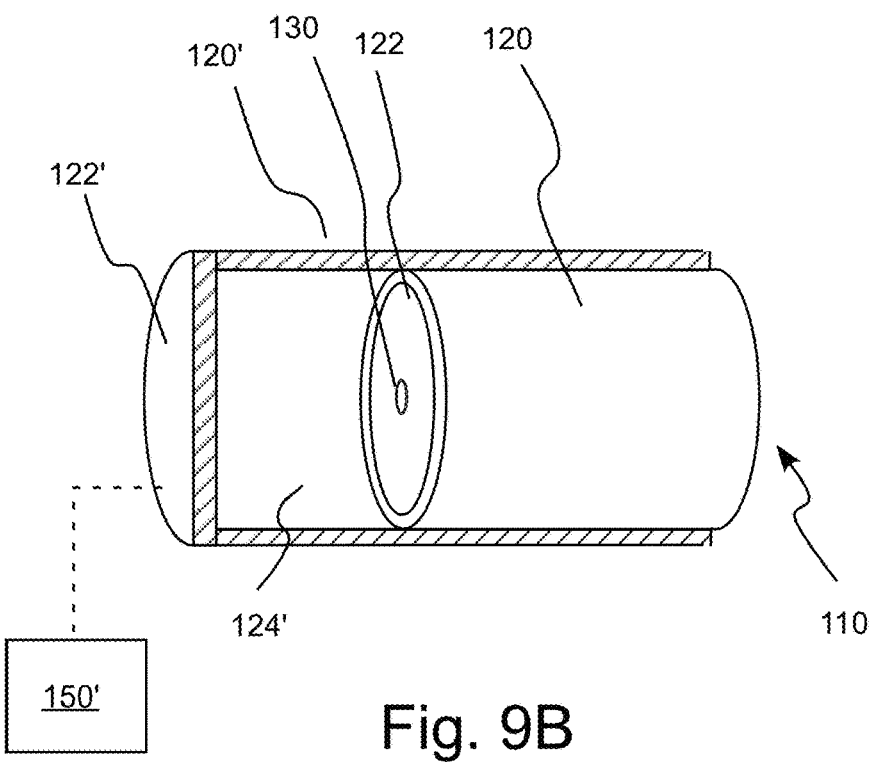
FIG. 9B illustrates a schematic, cross-sectional view of the system portion of FIG. 9A in which the volume in fluid connection with the oxygen sensor is in a restricted or closed state wherein the sensor is not in fluid connection with the ambient atmosphere.

FIGS. 9A and 9B illustrate schematically an embodiment hereof in which a gas such as oxygen in the ambient atmosphere is used to test or interrogate a system via dynamic coulometric measurement. In the illustrated embodiment, a sensor such as sensor 110 described above is provided. Along with sensor 110 and other components of a permanent sensing application (as known to those skilled in the art, and which are similar to those describe above for portable sensor systems), a small volume or space (sometimes referred to herein as a diffusion volume) and an associated restrictor system or mechanism (that is, a system or mechanism which restricts of or limits (including eliminating) flow of molecules into the volume) are situated immediately adjacent to sensor 110. The diffusion volume may, for example, incorporate all flow/diffusion paths into the sensor, including dust covers, filters, etc. The diffusion volume is relatively small and in no way interferes with the normal operation of sensor 110, including normal sensing and calibration. However, the diffusion volume is provided with a restrictor mechanism that, when applied, may, for example, create a small sealed volume immediately adjacent to the inlet diffusion means of sensor 110, thereby disrupting flow/diffusion of oxygen from the ambient atmosphere into the volume. In the embodiment of FIG. 9A, sensor housing 120 is at least partially encompassed within a secondary housing or cap 120' to create a volume 124' adjacent inlet 130 formed in lid 122' of sensor housing 120.

Figure 9C:
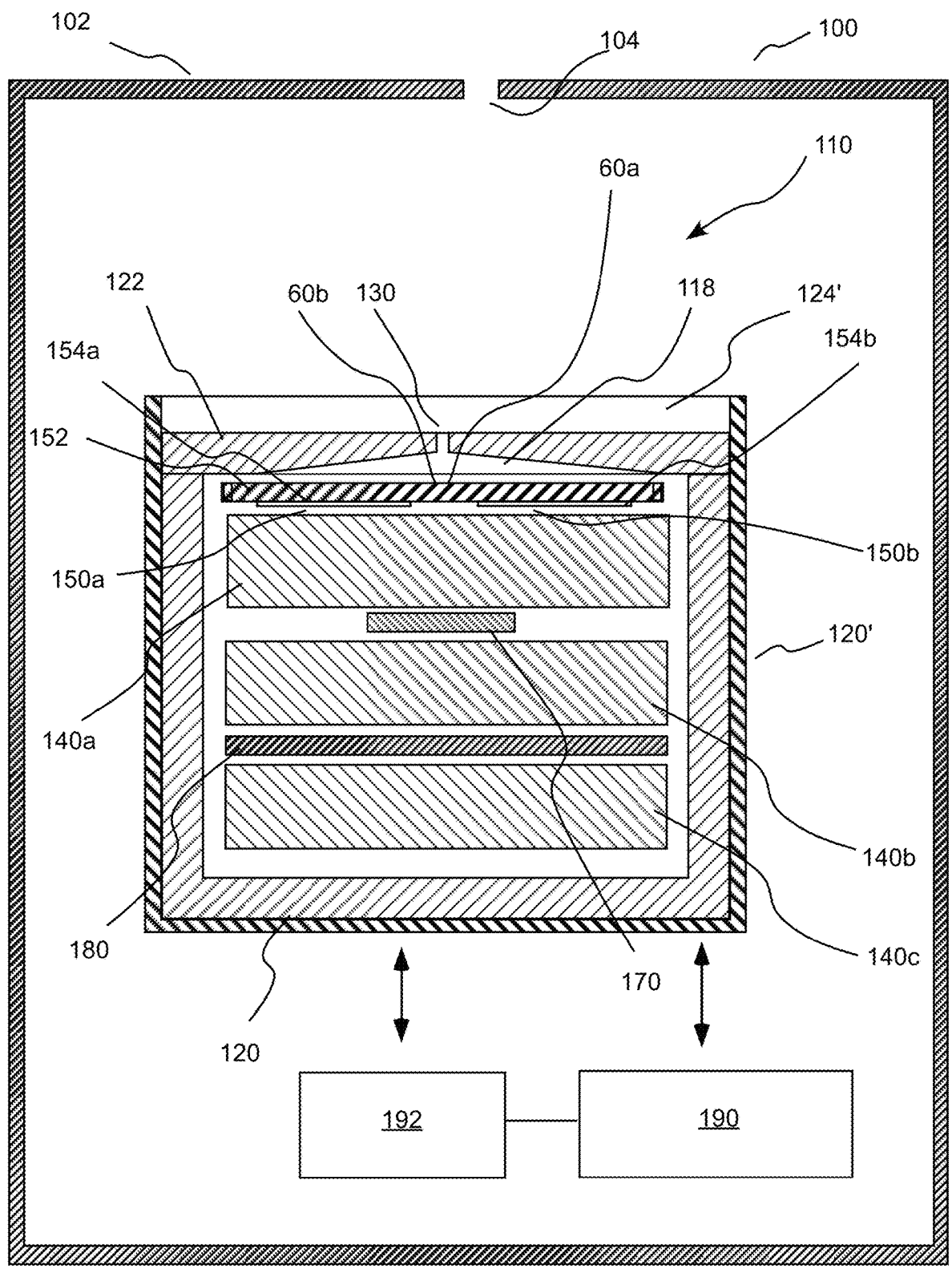
FIG. 9C illustrates a system including the sensor of FIG. 2A in which oxygen in the atmosphere is used to test or interrogate the system via dynamic coulometric measurement, and in which a volume in fluid connection with the oxygen sensor of the system is in an open state.
Figure 9D:
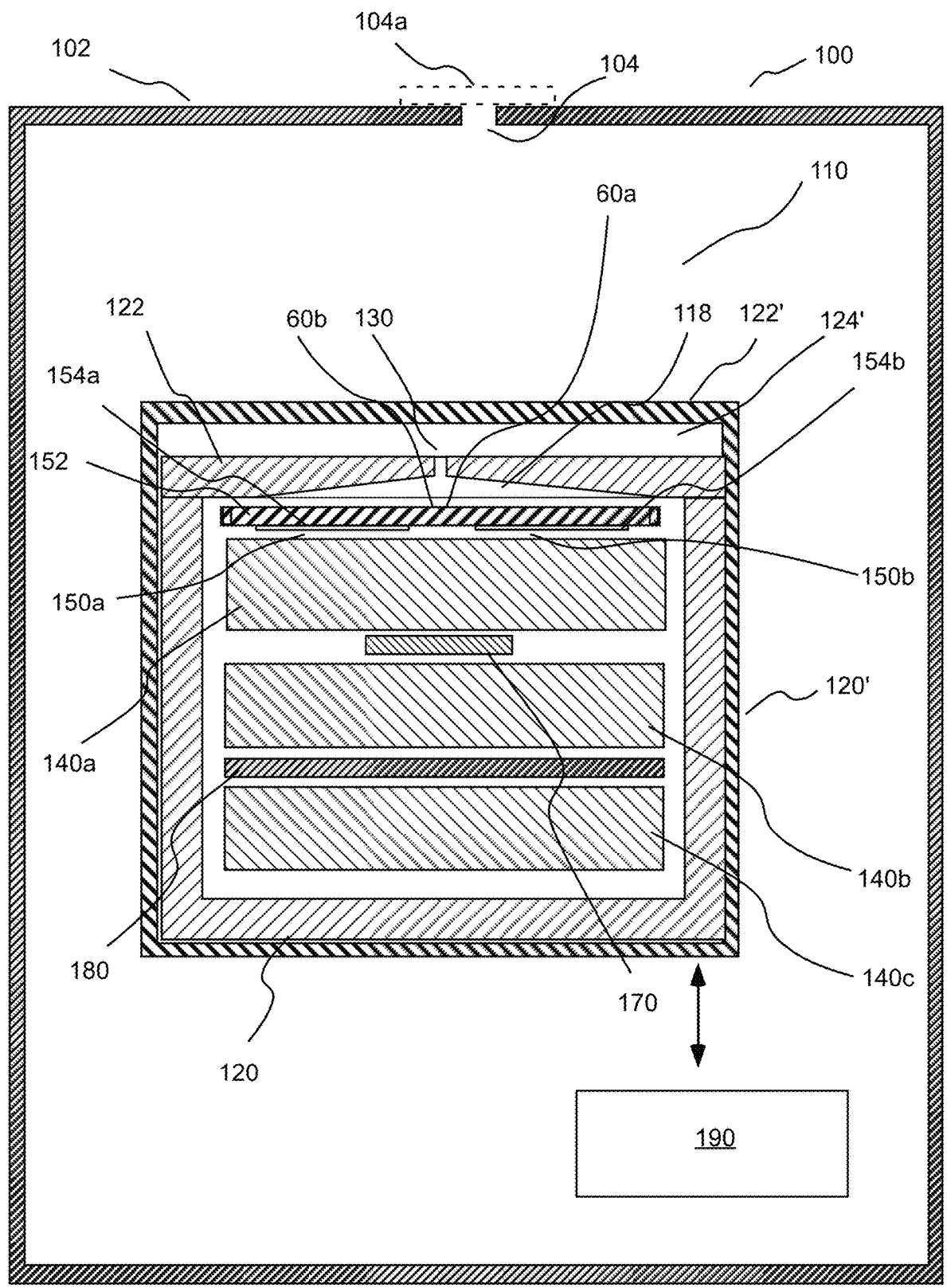
FIG. 9D illustrates a schematic, cross-sectional view of the system in FIG. 9C in which the volume in fluid connection with the oxygen sensor is in a restricted or closed state.

FIG. 9A illustrates sensor 110 and diffusion volume 124' in normal (fully open) operation wherein volume 124' and sensor inlet 130 are in fluid connection with the ambient atmosphere in which the concentration of an analyte is to be tested. FIG. 9B illustrates sensor 110 and volume 124' in a restricted, closed or interrogation/testing position via a controllable restrictor mechanism, closure or lid 122', which may be controllably altered between a fully open state as illustrated in FIG. 9A and a flow/diffusion restricted or closed state as illustrated in FIG. 9B. In permanent sensing applications, restrictor mechanism 122' may, for example, be actuated remotely, either by user input, or automatically, by the sensing device itself via a local and/or remote control system 150' illustrated schematically in FIG. 9B. Like other Figures hereof, FIGS. 9A and 9B are not necessarily drawn to scale. FIGS. 9C and 9D illustrate a cross-sectional view of sensor 110 incorporated within instrument or system 100 wherein closure 122' (see FIG. 9D) is an open state and a flow/diffusion restricted or closed state, respectively (FIGS. 9C and 9D are not necessarily drawn to scale). As illustrated in FIG. 9D, alternatively, a restrictor mechanism 104a (illustrated in dashed lines) may be provided to restrict or close inlet 104 of system 100 so that the created diffusion volume incorporates all diffusion paths into sensor 110, including dust covers, filters, etc.

With closure 112' (or restrictor mechanism 104a) in an open state, and the absence of an alarm condition, with a nominal signal present on the oxygen sensitive channel of sensor 110, and with a nominal response to the electronic sensor interrogation system described below, it is highly likely that there is present in (diffusion) volume 124' (adjacent to sensor 130), ambient air with an oxygen concentration of approximately 20.8 vol-%. Upon actuation of restrictor mechanism 122' (or restrictor mechanism 104a) to place it in, for example, a closed state as illustrated in FIG. 9D, there is created, immediately adjacent to sensor inlet 130, a small, closed and fixed volume 124' with a trapped volume of gas containing a fixed amount of oxygen. That amount of oxygen will be consumed by the oxygen sensitive channel of sensor 110 (described above), resulting in an asymptotically decreasing signal on the oxygen sensitive channel. In a number of embodiments hereof volume 124' is maintained relatively small to ensure a relatively quick depletion of the oxygen therein. For example, in a number of embodiment, volume 124' is in the range of 0.25 to 1.5 ml. In a number of embodiments, volume 124' is approximately 0.5 ml.

It is not necessary to completely close the diffusion volume 124' adjacent to sensor 110, but it is only necessary to sufficiently disrupt or restrict the diffusion of oxygen to the oxygen sensitive channel of sensor 110 to cause a change in signal that can be analyzed according to the principals of analytical coulometry, as described below. Altering or cycling restrictor mechanism 112' (or restrictor mechanism 104$a$) between an open, a closed, or a restricted state provides differential data, all of which can be deconvoluted to assess the condition of the flow path and flow elements into sensor 110.

Coulometry, as described above, is an analytical electrochemical technique fundamentally involving the measurement of the passage of charge, in coulombs, involving a Faradaic conversion of substance, that is, electrolysis. The measurement of charge is a fundamental (as opposed to derived) measurement, and therefore, can be used to make absolute quantitative analytical measurements.

Coulometry, or coulometric measurement, is typically performed using a coulometer, either electronic or electrochemical. Typically, coulometry is performed at constant potential and is often referred to as "bulk electrolysis." Given a well behaved electrochemical reaction, presented in the general form:

$$Ox + ne^- \rightarrow Red \qquad 1.3$$

a system can be easily set to reduce the oxidized species (Ox) at a constant potential until it is completely converted to the reduced species (Red). This is signaled by a drop in observed current to zero. The amount of electricity (the number of coulombs) necessary to cause this conversion is a direct measurement of the amount of oxidized species originally present in the system.

There are a number of ways in which a system can be modulated or dynamically changed to perform a coulometric measurement in a shorter time than by completing bulk electrolysis. For the particular systems described herein, a volume of gas in communication with an oxygen sensor is suddenly closed off from the ambient atmosphere (wherein diffusion of the analytically important species or analyte is modulated). The oxygen in the trapped sample is electrochemically consumed by the sensor (via working electrode 150$b$ in the representative example) according to:

$$O_2 + 4H^+ + 4e^- \rightleftharpoons 2H_2O \qquad 1.4$$

If the volume of the sample is known, the absolute concentration of oxygen in the trapped sample can be calculated based on the charge necessary to completely consume it. Other techniques might be used to estimate the oxygen concentration including, for example, the rate of decay of the reduction current, or time to reach a predetermined fraction of the original, un-modulated current. Many other schemes might be imagined. The theory behind dynamic measurements is discussed, for example, in Stetter, J. R. and Zaromb, S., *J. Electroanal. Chem.,* 148, (1983), 271, the disclosure of which is incorporated herein by reference.

Figure 9E:
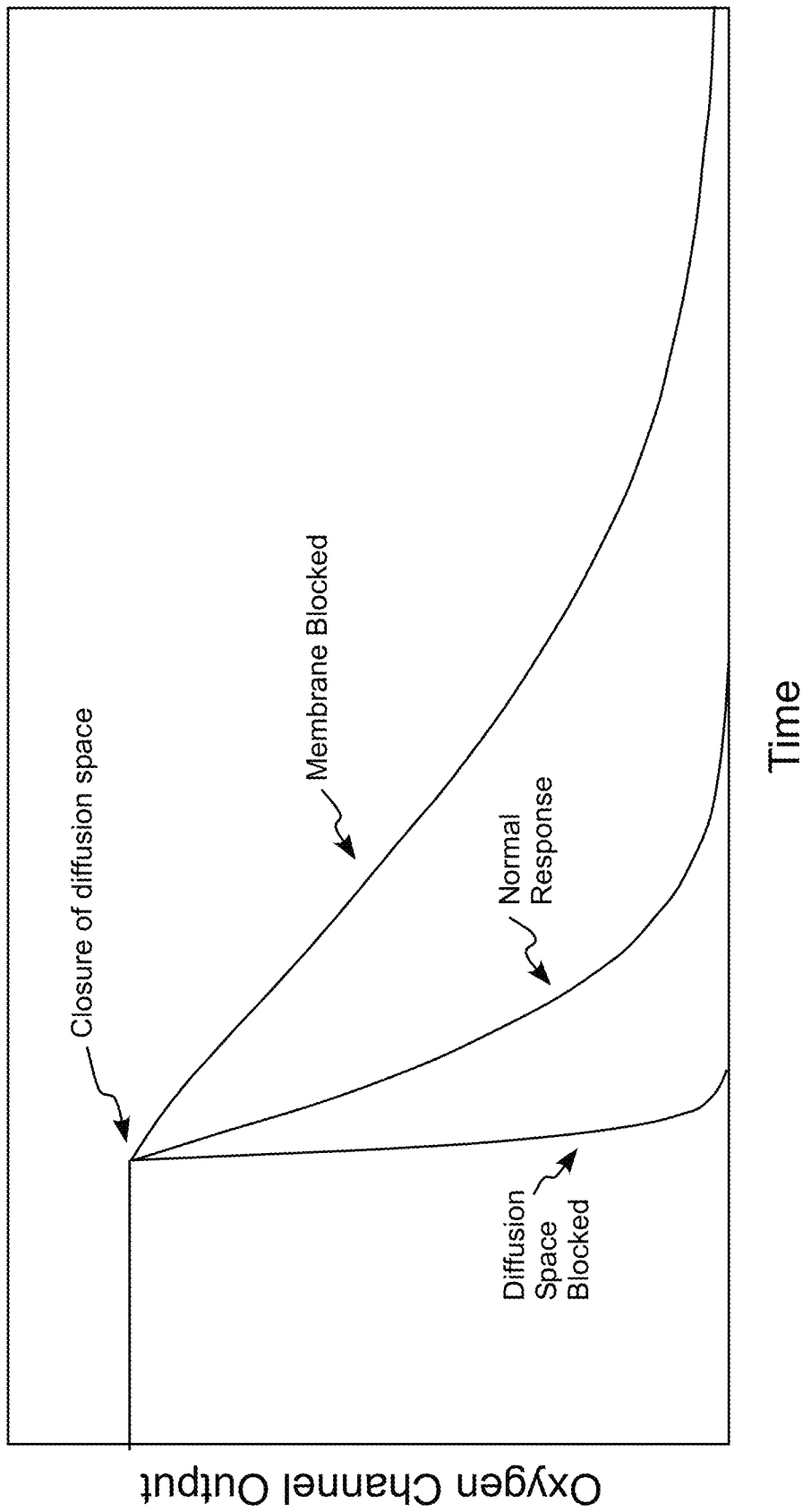
FIG. 9E illustrates a number of potential output response curves of the oxygen channel of a system such as the system of FIGS. 9C and 9D when the volume in fluid connection with the oxygen sensor is in a restricted or closed state.

At least three system conditions for the systems described herein can be related to the response of the oxygen sensitive channel of the sensor (for example, via a processing system 192 including appropriate circuitry and/or one or more processors such as a microprocessor). Each of those conditions and the corresponding oxygen channel response/output is illustrated in FIG. 9E. For normal operation, including an initial 20.8 vol-% oxygen (see discussion above) and nominally open membranes, a signal decay curve similar to that labeled "Normal Response" is obtained. In this situation, the velocity of the signal decay is dependent only on the speed with which the trapped amount of oxygen diffuses to the oxygen sensitive element of the sensor (for example, working electrode 150$b$ of sensor 110) and is consumed by the electrochemical reaction there present.

In the situation wherein the diffusion membrane(s) of the sensor inlet are blocked by dust, or other foreign matter, the rate of diffusion of oxygen to the sensor is decreased and a signal response similar to that labeled "Membrane Blocked" is obtained.

Alternatively, in the case of permanent sensing applications, it is possible that bulk matter may become deposited in the diffusion volume (for example, volume 124'), however small it may be. This may, for example, occur when an insect nest or the like occludes the face of the sensor. This situation is depicted in the signal response labeled "Diffusion Space Blocked." In this case, the gas volume trapped in the diffusion volume is reduced from the normal case by the bulk matter present in the closed diffusion space and the response is observed to drop more quickly than the normal response.

In the case that oxygen variation (for example, as a result of a breath test or a flow/diffusion restriction test) is measured, sensing elements other than amperometric oxygen sensing element may, for example, be used. In that regard, any alternative oxygen sensing system may be used in place of an amperometric oxygen sensing. Representative examples of suitable oxygen sensing systems include, but are not limited to, a metal oxide semiconductor or MOS (also colloquially referred to as a "Figaro" sensor) oxygen sensing element, a high temperature potentiometric oxygen sensor (zirconia sensor), a combustible gas sensor, or a paramagnetic oxygen sensor. A particular oxygen sensing technology may, for example, be more suitable as a complement to a given toxic gas or other sensing technology for a particular use. For example, an MOS or zirconia-based oxygen sensing element may be well suited for use with an MOS toxic sensor or with a heated catalytic bead combustible gas sensor.

Figure 10:
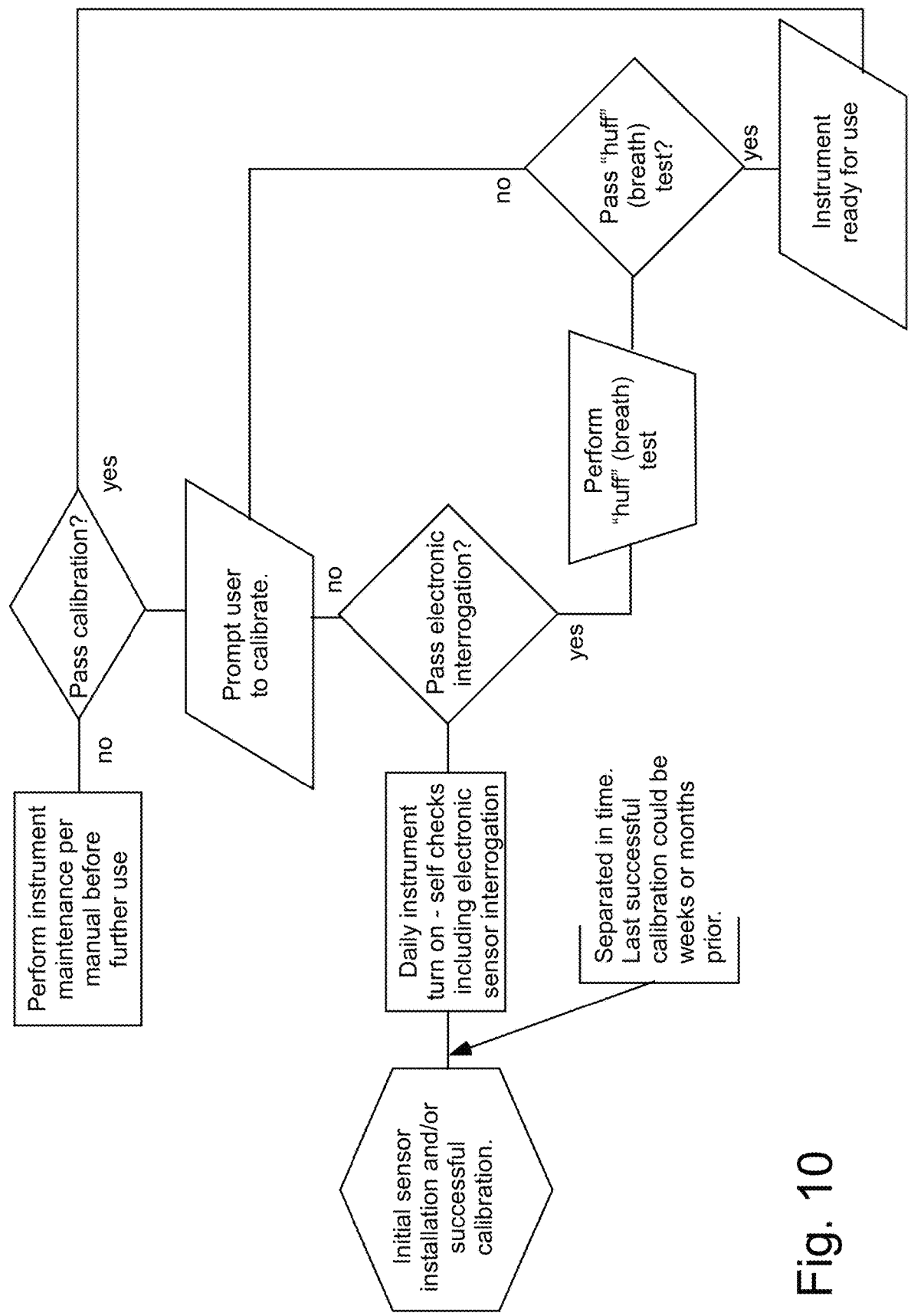
FIG. 10 illustrates a decision tree diagram setting forth a representative embodiment of an operating mode or method of a system hereof.

FIG. 10 illustrates a decision tree diagram that depicts a representative embodiment of an operating mode or method for use in connection with sensors for an analyte in any of the systems hereof. The method illustrated in FIG. 10 assumes a successful complete calibration of the instrument (with a calibration gas) at some point in time, either at final assembly and testing or in the field. In daily use, when the instrument is turned on, as is typical, the instrument will perform its necessary self-diagnosis checks. Part of this self-diagnosis may, for example, include the application of an electronic interrogation of a sensor such as, for example, a life and health check similar to that described in U.S. Pat. No. 7,413,645.

Figure 11:
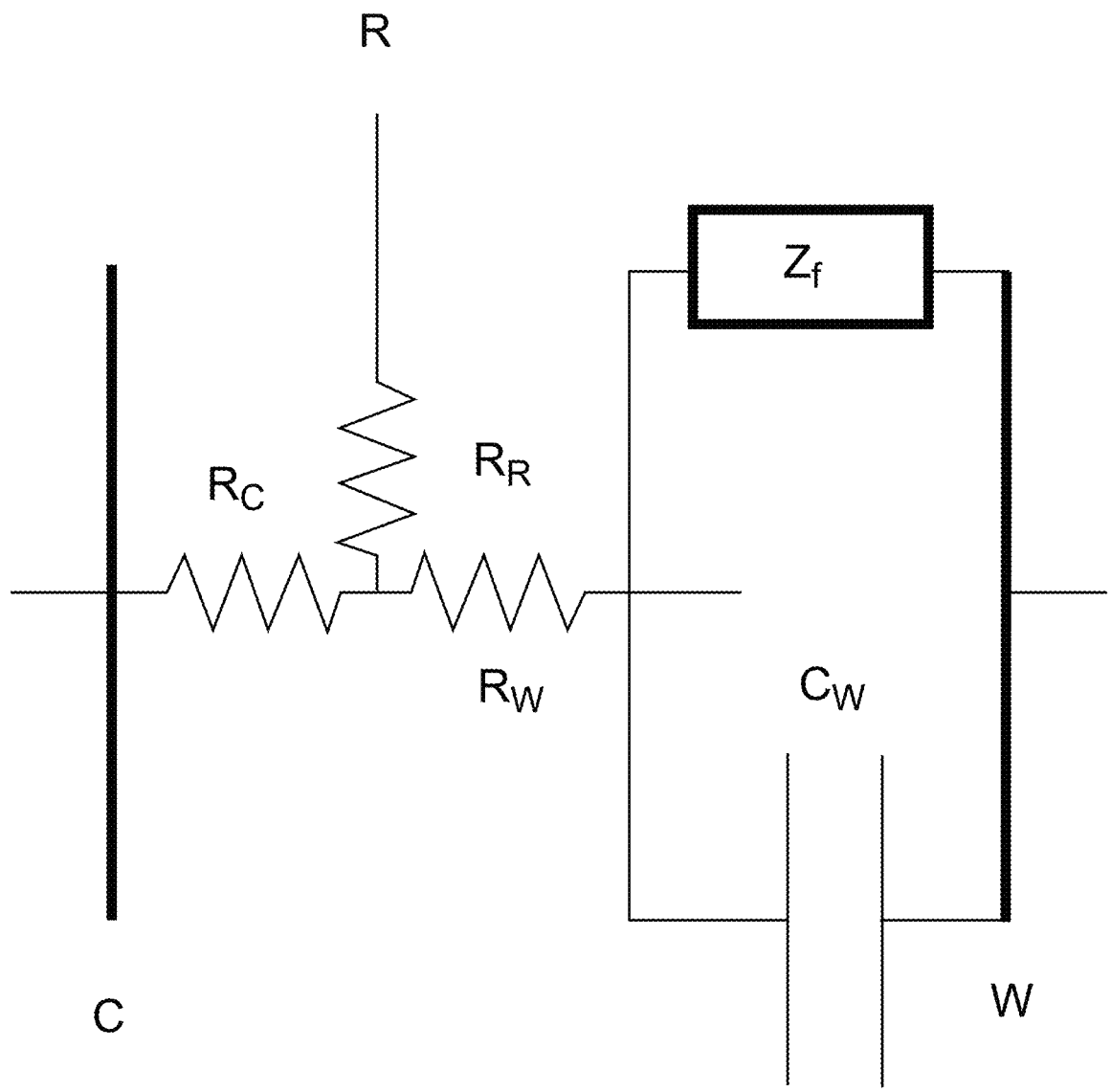
FIG. 11 illustrates an equivalent circuit used to describe electrochemical cells.

As described in U.S. Pat. No. 7,413,645, and as illustrated in FIG. 11, a sensor generally can be described as a combination of resistances and capacitance in series. The resistance $R_R$ resulting from the reference electrode of FIG. 11 is not part of the current path of the analytical signal of the sensor. The resistive portion of this circuit is primarily a result of the solution (ionic) resistance of the electrolyte interspersed between the working electrode ($R_W$) and the counter electrode ($R_C$). The capacitive portion ($C_W$) of the equivalent circuit is primarily a result of the micro solution environment found very close to the surfaces of the metallic particles that comprise the working electrode. As a result of electrostatic forces, the volume of solution very close to the electrode surface is a very highly ordered structure. This structure is important to understanding electrode processes. The volume of solution very close to the electrode surface is variously referred to as the diffusion layer, diffuse layer, and or the Helmholtz layer or plane.

The magnitudes of the resistance and capacitance present in an electrochemical cell are a result of the nature and identities of the materials used in its fabrication. The resistance of the electrolyte is a result of the number and types of ions dissolved in the solvent. The capacitance of the electrode is primarily a function of the effective surface area of the electrocatalyst. In an ideal world, these quantities are invariant. However, the solution resistance present in an amperometric gas sensor that utilizes an aqueous (water-based) electrolyte may change, for example, as a result of exposure to different ambient relative humidity levels. As water transpires from the sensor, the chemical concentration of the ionic electrolyte increases. This concentration change can lead to increases or decreases in the resistivity of the electrolyte, depending on the actual electrolyte used.

The response curves of sensors have the shape expected for the charging curve of a capacitor, that is a typical "RC" curve. In a number of embodiments, the analytical signal used to determine the "health" of a sensor is the algebraic difference in the observed potential just prior to the application of a current pulse and at the end of the current pulse. The magnitude of the potential difference observed as a function of the application of the current pulse is an indicator of the presence and the health of any sensor of the system hereof and provides an independent check of sensor system operability.

Although limitations on the magnitude and duration of the current pulse have mostly to do with experimental convenience, the magnitude of the current pulse may, for example, be chosen to correspond to application of a reasonably expected amount of target gas.

Sensor presence and health may be determined by the shape of the sensor's RC charging curve, being measured by observing the difference in sensor output at the beginning and the end of the current pulse. If the sensor is absent, the observed potential is equal to that which would be expected based on the magnitudes of the current pulse and the sensor load resistor.

Figure 12:
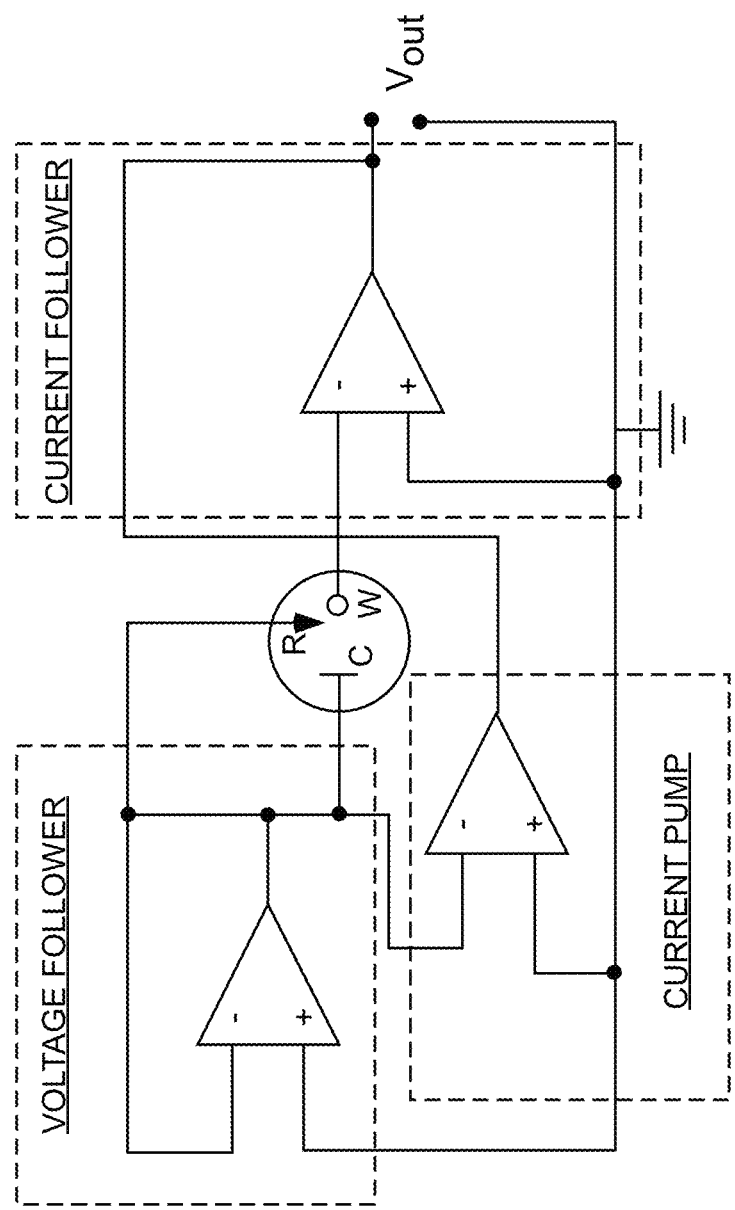
FIG. 12 illustrates a block diagram of an embodiment of measurement circuitry for electronic interrogation.

FIG. 12 illustrates a block diagram of one embodiment of an electronic interrogation circuit as described in U.S. Pat. No. 7,413,645 and as used in several embodiments of the systems described herein. In FIG. 12, the voltage follower and the current follower sections function as known to one skilled in the art. See, for example, A. J. Bard and L. R. Faulkner, *Electrochemical Methods: Fundamentals and Applications*, John Wiley & Sons: New York (1980), the disclosure of which is incorporated herein by reference. The voltage follower maintains a constant potential between the reference electrode (R) and the working electrode (W). The current follower buffers and amplifies currents which flow in the electrochemical sensor between the counter electrode (C) and the working electrode (W). In an number of embodiments, the current pump applies electronic interrogation to the sensor by forcing a known current to flow between the counter electrode (C) and the working electrode (W).

On or more additional electronic interrogation tests may, for example, be performed on one or more combustible gas sensors in an instrument. For example, U.S. patent application Ser. No. 13/795,452, filed Mar. 12, 2013, and entitled DIAGNOSTICS FOR CATALYTIC STRUCTURES AND COMBUSTIBLE GAS SENSORS INCLUDING CATALYTIC STRUCTURES, the disclosure of which is incorporated herein by reference, discloses an electronic interrogation test for a sensing element of a combustible gas sensor in which a variable related to reactance of the sensing element is measured, and the measured variable is related to an operational state or functionality of the sensing element.

In a number of embodiments hereof wherein an electronic interrogation as described above or another electronic interrogation is used, redundant analytical sensors (that is, redundant analytical sensors for the same analyte) may facilitate continuous sensing of the analyte. For example, a two channel amperometric electrochemical sensor with redundant, identical analytical channels may be used. The electronic interrogation may, for example, be applied independently to each channel, in turn. In this embodiment, the benefits of electronic interrogation are obtained. However, because of the redundant, identical analytical channels, at no time would the sensing capability of the sensor for the analyte sensed by the redundant sensor be affected. Such embodiments might be particularly useful for permanent sensor system installations, or for any sensor installation wherein the analytical signal of the sensor system for a particular analyte cannot be interrupted, even for the short times necessary for the electronic interrogation described herein or another electronic interrogation.

In a representative embodiment, a redundant carbon monoxide sensor system may, for example, include two independent platinum (Pt) working electrodes, a first working electrode and second working electrode, which may, for example, be dispersed on the same porous electrode support. Each working electrode is operated independently of the other, providing redundant indication of the absence or the presence and concentration of carbon monoxide applied to the sensor. At some predetermined time, either manually, remotely, or automatically, the first working electrode would undergo the electronic interrogation check, and the information necessary for the real-time correction of the analytical signal and/or maintenance of channel 1 would be collected. The second working electrode/channel 2 would be completely unaffected by this operation on channel 1. Sometime after the completion of the electronic interrogation of the first working electrode/channel 1, after the effects of the interrogation have passed and a correct baseline is re-established, the second working electrode/channel 2 would undergo the same electronic interrogation and signal collection, and the same data would be obtained for channel 2. In this way, at no time is the analytical signal for carbon monoxide from the sensor interrupted. This redundant working electrode/channel configuration may, for example, be utilized in connection with electronic or other interrogations procedures other than the electronic interrogation described in connection with FIGS. 10 through 12. Moreover, the configuration is applicable to sensors other than electrochemical sensors (for example, combustible gas sensors).

A further embodiment is illustrated in FIGS. 13A and 13B. In this embodiment, a sensor 410e includes a first working electrode 450e(i) and second working electrode 450e(ii), which are identical analytical electrodes as described above. Sensor 410e further includes a third working electrode 450e(iii), which is a pseudo-analytical or non-analytical electrode that is responsive to a driving force applied in the vicinity of an inlet 430e formed in an upper portion 422e of the sensor housing to effect a flow path test hereof. As described above, third working electrode 450e(iii) may, for example, be responsive to some component of exhaled breath (oxygen, for example). In a number of embodiments, all three working electrodes 450e(i), 450e(ii) and 450e(iii) are dispersed on the same porous support or diffusion membrane 452e. Working electrodes 450e(i), 450e(ii) and 450e(iii) are operated independently of each other, however. Working electrodes 450e(i), 450e(ii) and 450e(iii) are in simultaneous fluid connection with the atmosphere being sensed via V-shaped gas inlet 430e. Alternatively, each channel may have a separate gas inlet, or the various channels may be in fluid contact with the atmosphere being sensed in a multitude of combinations. Working electrode 450e(iii) may, for example, be used the perform a flow path test as described herein by, for example, applying a driving force to inlet 430e of sensor 410e (for example, by applying exhaled breath). Working electrode 450e(iii) would respond as previously described and would provide an indication of the operative state or functionality of the flow path into sensor 410e.

Following an electronic interrogation test as described above as an independent check of sensor health, the user may, for example, be prompted to perform a flow path test such as an exhaled breath test or a "bump check" hereof (without calibration gas) by exhaling closely into the instrument face. Embedded instrument software observes the resulting signal on, for example, second working electrode 250b (designed to respond to some driving force/variable change associated with exhaled breath such as a change in oxygen concentration). In the embodiment of sensor 210, the observed response is a result of the decreased oxygen content in exhaled human breath. The embedded instrument control software compares the result of the electronic interrogation test and the result of the exhaled breath test to established parameters. If the responses of either the electronic interrogation test or the flow path/exhaled breath test fail to meet these pre-established criteria, the instrument may prompt the user to perform a full calibration or some other maintenance. If the results of both the electronic interrogation test and the flow path/exhaled breath test meet or exceed the pre-established criteria, the instrument may indicate to the user that it is functioning properly and is ready for daily use.

Figure 14B:
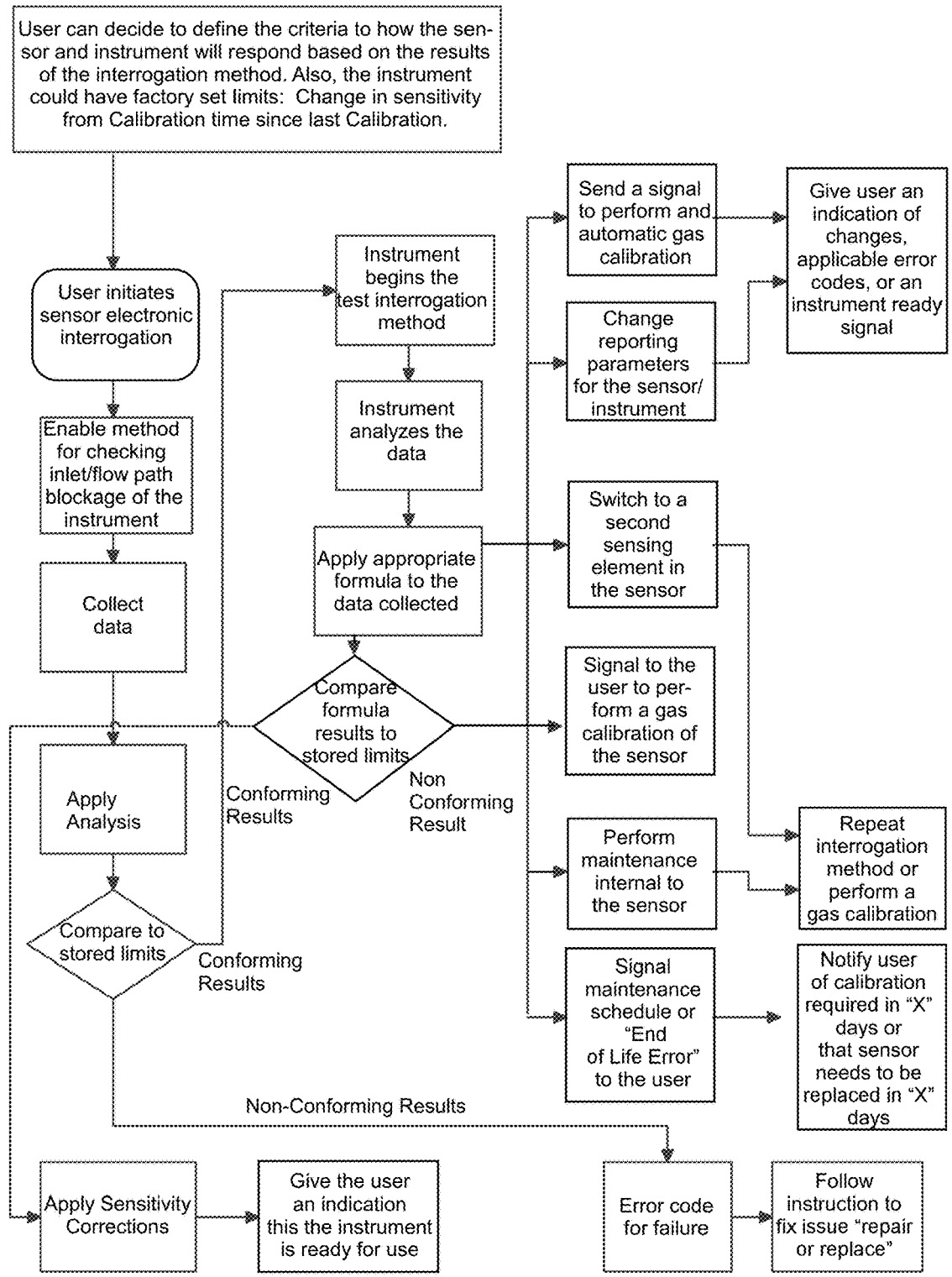
FIG. 14B illustrates a flow chart of another embodiment of a sensor/system interrogation process hereof.
Figure 14C:
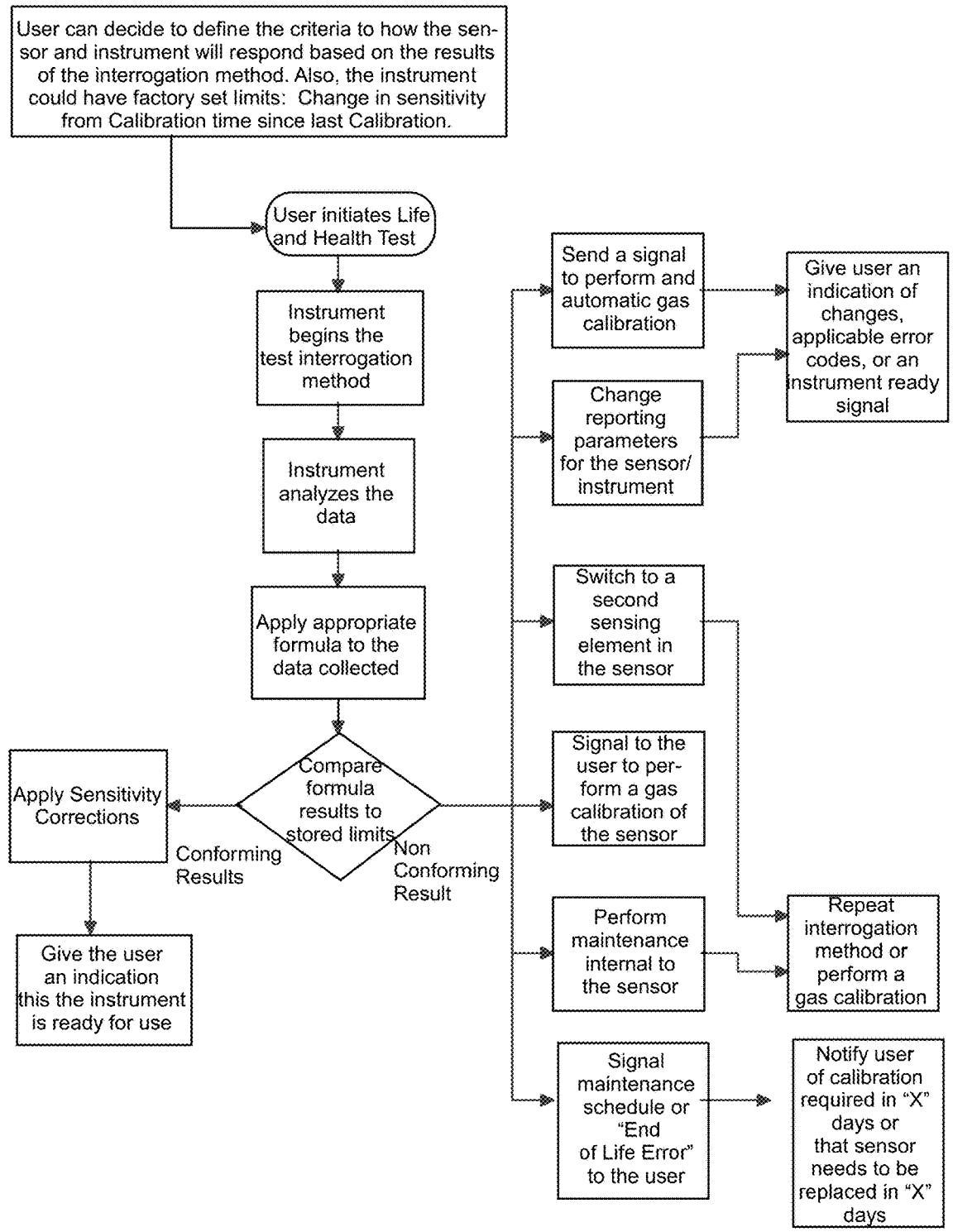
FIG. 14C illustrates a flow chart of another embodiment of a sensor/system interrogation process hereof.

FIGS. 14A through 14C illustrate further embodiments of operating methodologies or schemes for systems hereof. FIGS. 14A and 14B illustrate operating methodologies in which both a life and health test (that is, a test including an electronic interrogation or stimulation of a sensor) and a flow path test or interrogation hereof are performed. In the operating methodology of FIG. 14A, the electronic interrogation or sensor life and health test is performed first and the flow path test is performed thereafter. In the operating methodology of FIG. 14B, the flow path test or interrogation is preformed first and the electronic interrogation or sensor life and health test is performed thereafter. In the operating methodology of FIG. 14C, only a life and health or electronic interrogation test is performed.

In an initial, set-up phase, a user may be provided with the ability to adjust certain limits and set points prior to using either the sensor electronic interrogation feature or the flow path test feature. Examples of such adjustments include, but are not limited to, changes between calculated and calibrated sensitivity and time since last calibration. Once the initial set-up is complete, the user may, for example, begin using the sensor interrogation features. A user may, for example, begin by initiating one of the interrogation methods. Alternatively, initiation of one of the interrogation methods may be set up to automatically occur after a certain length of time, at a certain date, at a certain time of day, etc. User initiation may, for example, be carried out in many different manners including, for example, actuating a button, transmitting a wireless command etc. Upon initiation, the system or instrument begins the test or interrogation process. The instrument then analyzes the data collected during the test process. The system or instrument (via, for example, a control system which may include a processor and/or other control circuitry) applies a predetermined algorithm or formula to the data and then compares the results from the algorithm or formula to the set points or thresholds earlier established (for example, during set up).

If the data from, for example, an electronic interrogation or life and health test of a sensor is "non-conforming" or outside of one or more determined set points or thresholds, one or more of the following representative tasks may be performed either individually or in any combination: a) perform an automatic or automated (that is, without user intervention) gas calibration of the sensor, b) change the reporting parameters of the sensor/instrument, c) switch to a second sensing element in the sensor or a new sensor for a particular analyte, d) signal the user to perform a "gas calibration" or perform other maintenance, e) perform automated maintenance internal or external to the sensor system, and/or f) signal to the user an "end of life" error message. For options "a", "b", "f" the user may, for example, be provided a code providing information of what changes have occurred or another indication of any changes. Such information may be simply communicated to the user or the system may require a user's acknowledgement or approval of the changes. For options "c" and "d", the system may, for example, require the user or instrument to repeat the "interrogation method" or signal the user or system to perform a "gas calibration".

In the case of an automatic or automated gas calibration, the user need not supply the gas or otherwise intervene. In that regard, a compressed gas container may be present in the vicinity of a permanent instrument. Alternatively, the test or calibration gas may be a generated in situ or otherwise released in a manner to enter the inlet of the instrument. In situ gas generation is well know to those skilled in the art. For example, hydrogen gas ($H_2$) can easily be generated from an electrochemical gas generator, which then can be used to calibrate both hydrogen and carbon monoxide electrochemical sensors. Other gases of interest such as chlorine ($Cl_2$) and chlorine dioxide ($ClO_2$) can be electro-generated as well. Also, there are methods of storing a gas of interest in a solid matrix from which it can then be thermally released. After such an automated calibration, the user may be provided with an indication of any system parameter changes, error codes and/or the readiness of the instrument for further use.

In the case of changing the parameters of the sensor/instrument, parameters such as gain, range or resolution, cross-sensitivity parameters, set points (for example, alarm set point), alarm signals (for example, the type of signal) and/or other parameters may be adjusted for one or more sensors of an instrument on the basis of the results of an interrogation method hereof. For example, based on those results, the resolution of, for example, an $H_2S$ sensor or other sensor of the instrument may be changed from 0.01 ppm to 0.1 ppm. Other parameters that can be changed based on the results of interrogation methods would include, but would not be limited to, changing the linear range of the sensor so that gas values above or below certain level would not be displayed or reported or be displayed or reported on a different format. Additionally, any corrections to the linearity of the sensor signal that are normally applied may be altered or adjusted based on the results of interrogation events. The electronic gain or amplification applied to the signal of a sensor may also be adjusted in the same manner. A set point for an alarm threshold may be changed. Likewise, the alarm type to be provided to a user may also or alternatively be changed. The user may be informed of such a change as described above. Such a parameter change or other parameter change may, for example, be made until the next interrogation or until the next gas calibration. Once again, the user may be informed of the change and may be requested to acknowledge the change.

In the case of a multi-sensor system such as system 400 of FIGS. 3H and 3I, redundancy of sensors may be provided. In that regard, if non-conforming results are obtained in an electronic interrogation of a sensor, the system may switch to a second sensing element in the sensor. Alternatively, a user may be alerted to remove the non-conforming analytical sensor and replace that sensor with a new sensor for a particular analyte. After switching to the second sensing element, the system may repeat the interrogation and/or a gas calibration may be performed (either an automated calibration or a user assisted calibration).

Moreover, if a sensor is determined to no longer be suitable for detection of a particular analyte, it may be suitable for detection of another, different analyte at the same or at a different biasing potential. The system may, for example, switch the sensor to detection of a different analyte in an automated procedure. The biasing potential of the sensor may, for example, be changed to facilitate the sensing of the different analyte. As with other changes, the user may, for example, be notified and may be required to acknowledge or approve the change.

In the case that the instrument signals the user to perform a gas calibration, the user will supply a test gas (for example, a gas including a known concentration of the analyte or a simulant therefor) to the instrument inlet. User initiated maintenance might include, for example, changing filters or dust covers. Many electrochemical sensors are equipped with external chemical filters to remove interfering gases (see, for example, FIG. 1). The data from an electronic interrogation of a sensor and/or a flow path test may, for example, be used to signal the user that such a filter needs to be replaced. In the same way, many instruments, especially portable instruments, come equipped with filters or dust covers that protect the sensor and the internals of the instrument from intrusion of water, dust and other foreign materials. These dust covers and filters normally include at least part of the flow path into the sensor. The data from an electronic interrogation of a sensor and/or a flow path test may, for example, be used to signal the user that such filters or dust covers need to be replaced.

Upon a certain result or combination of results from electronic interrogation, the instrument or system may initiate an automated maintenance procedure. For example, the bias potential of an electrochemical sensor may be altered via the instrument/system control system or controller. The bias potential of the working or sensing electrode of the electrochemical sensor may, for example, be altered 1) to increase its sensitivity to the target analyte, 2) to enhance the working electrode's ability to discriminate against an interfering gas (that is, a gas to which the working electrode is responsive other than the analyte of interest). Moreover, a regeneration procedure may be initiated. The biasing potential of the working or sensing electrode may, for example, be changed to remove (for example, via oxidation, reduction, or desorption), an interfering or inhibiting substance that may have formed on or near (or otherwise contaminated) the sensing electrode surface as a function of normal usage or as a result to exposure to an inhibiting agent or poison For example, the biasing potential of a sensing electrode may be changed for a period of time and then brought back to a potential at which the sensing electrode is sensitive to the target analyte. For example, a CO sensor which is typically operated at a bias potential of zero (0) mV may have its biasing potential increase to +500 mV for a period of time (for example, one hour). Subsequently, the sensing electrode is returned to its operating biasing potential of zero (0) mV. This procedure may, for example, improve cross-sensitivity to hydrogen ($H_2$). In the case of a combustible gas sensor, the temperature of the sensing element may be increased for a period of time to "burn off" an inhibitor (for example, a sulfur-containing compound). Increasing the temperature of a sensing element in a combustible gas sensor to, for example, burn off an inhibitor in response to an electronic interrogation of the sensing element of the sensor is disclosed in U.S. patent application Ser. No. 13/795,452, filed Mar. 12, 2013. Instead of automating the above-identified maintenance procedures, a user may alternatively be provided an indication of the need to perform any of the procedures.

The user may also be notified of an impending "end of life" of a sensor. For example, a user may be notified that the sensor should be replaced in "X" days or another time period. Likewise, the user may be notified of scheduled maintenance tasks required. For example, the user may be notified that a gas calibration is required in "X" days or another time period. Pre-planned or scheduled maintenance may, for example, be altered on the basis of the results of one or more interrogations.

The life and health test or electronic interrogation test may be run on multiple sensors within the instrument. Such an electronic interrogation may also be run upon a sensor (whether analytical or non-analytical) which is responsive to the driving force associated with the flow path test (for example, a non-analytical oxygen sensor) to test the operational status or functionality of that sensor. The results of electronic interrogations of multiple sensors can be combined in an analytical algorithm to determine actions (as, for example, described above) based upon that data. As described above, it is common for portable gas detection instruments to contain several sensors with a plenum through which gas is pumped by and external or internal gas pump. The sensors typically included in such an instrument would be a combustible gas sensor, an analytical oxygen sensor (which may or may not include a non-analytical oxygen sensing element or electrode) and several toxic gas sensors such as carbon monoxide and hydrogen sulfide sensors. At least one of the toxic gas sensors may, for example, include a non-analytical oxygen sensor channel for performing a flow path test hereof. As described below, it is possible to monitor the current of the pump to determine the condition of flow through the plenum. In addition, under normal operating conditions, the output of the analytical oxygen sensor should correspond to that expected for value of 20.8 vol-% (atmospheric) oxygen. Finally, the results of electronic interrogation of any or all of the electrochemical sensors, along with the results of applying a driving force to those sensors with non-analytical channels intended to respond to such a driving force (that is a flow path test) may be combined together with, for example, pump current (and/or other pump interrogation) measurements and the output signal of the analytical oxygen sensor to give a high degree of reliability that all sensors in the plenum are experiencing correct flow and are operating as intended. If, however, the results of these tests, either singly or taken together indicate a non-conforming condition, the combination of signals provide a means of differentially informing the user of the nature of the non conforming condition. For example, if the pump current is correct, but the result of the flow path test (for example, applying a driving force to which the non-analytical channel is sensitive) for a particular sensor is non-conforming, then that particular sensor requires maintenance. If however, the pump current is non-conforming, but the output of the analytical oxygen sensor is as expected, this would indicate a potential problem with the pump itself, or with is associated driving circuitry.

Once "conforming" results are obtained in the embodiment of FIG. 14A, the users (or the system) may move onto an inlet/flow path blockage testing as described herein. The system will enable the flow path test process and collect the associated data. The system then applies any associated algorithm/analysis and may, for example, compare the results to stored limits or thresholds. If the results are "non-Conforming, an error code or other indication may be provided to inform the user of any repair or replacement options (for example, replacement of filters etc.). If the results are "conforming", any and all associated sensor output corrections are applied. The user may also be informed that the instrument is ready for use.

In addition to sensor output corrections associated with the electronic interrogation of the sensor, the system may also apply one or more corrections to sensor output determined as a result of the flow path test. In that regard, sensors may, for example, be thought of as "molecule counters". Analytical sensors are thus calibrated in a manner that a certain amount of analyte molecules react at the analytical working or sensing electrode(s) as they diffuse through the instrument and measured values are converted to, for example, a part per million (ppm) or percentage based equivalent readings based upon previous calibration. When the inlet is open and unobstructed, rates of diffusion are very repeatable under the same conditions. As any instrument inlet becomes blocked or flow paths are otherwise obstructed, the rate at which the molecules can diffuse from outside the instrument housing to the sensor can slow, thus lowering the rate at which molecules will encounter the active portion of the sensor (for example, the working electrode of an electrochemical sensor), and thereby lowering the output. By measuring partial blockages as a result of one or more flow path tests hereof, one can adjust the sensitivity of the sensor to maintain accurate readings regardless of such partial blockages.

In a number of embodiments hereof, once a flow path test such as an exhaled breath test is complete, the system calculates a derivative of the sensor response, based on the function:

$$\text{Rate of change} = \frac{dx}{dt} = \frac{x_{(i+1)} - x_i}{(t+1) - t}$$

The equation shown above indicates a generalized derivative function. As is known to one skilled in the art, there are many arithmetic formulas which can be used to calculate a derivate from periodic data.

Figure 15A:
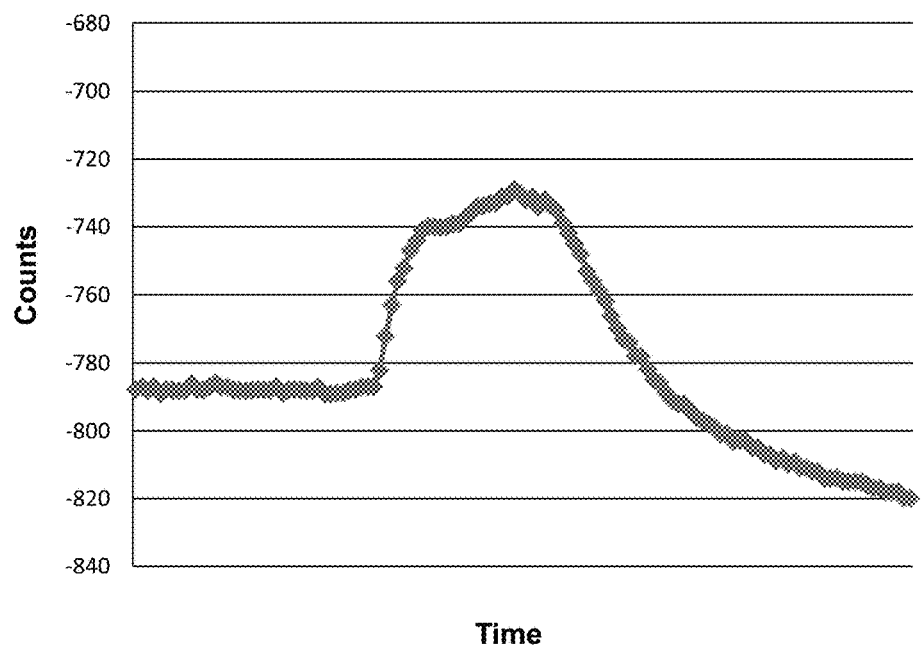
FIG. 15A illustrates sensor response or output for a typical flow path test hereof in the form of an exhaled breath test as a function of time.
Figure 15B:
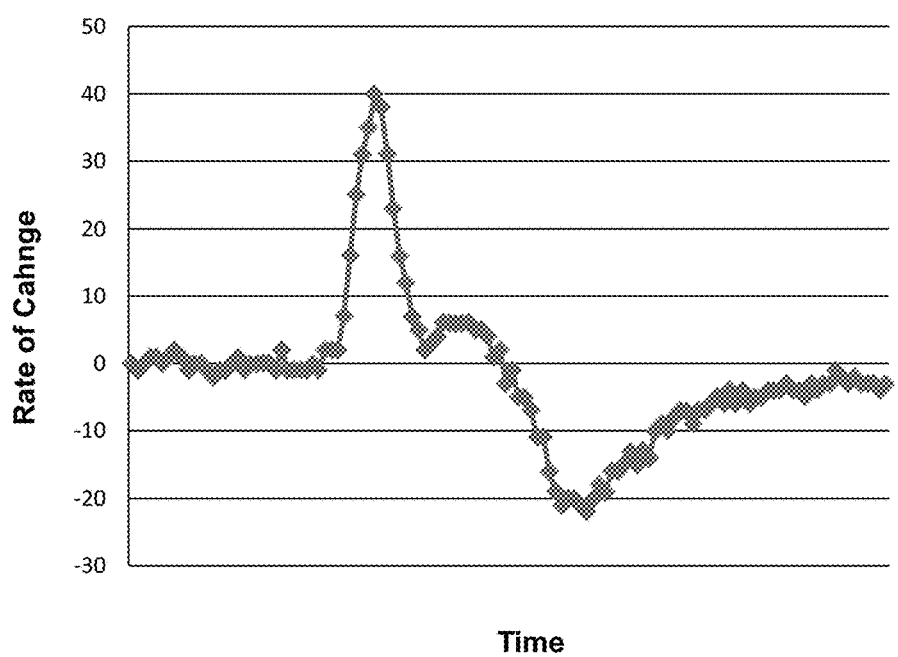
FIG. 15B illustrates a plot of the rate of change of the sensor response of FIG. 15A.

FIG. 15A illustrates sensor response or output for a typical flow path test hereof in the form of an exhaled breath test as a function of time. FIG. 15B illustrates a plot of the rate of change of the sensor response of FIG. 15A. A peak rate of change as percentage of the baseline is then calculated as follows:

$$\text{Peak rate of change} = \frac{\text{peak}_{max}}{\text{baseline}}$$

Referring to FIG. 15B, the peak$_{max}$ corresponds to the maximum value of the derivative function immediately subsequent to the application of the driving force, resulting in the positive deflection shown in FIG. 15A, and the baseline refers to a mean value of the derivative function prior to the application of the driving force.

Figure 15C:
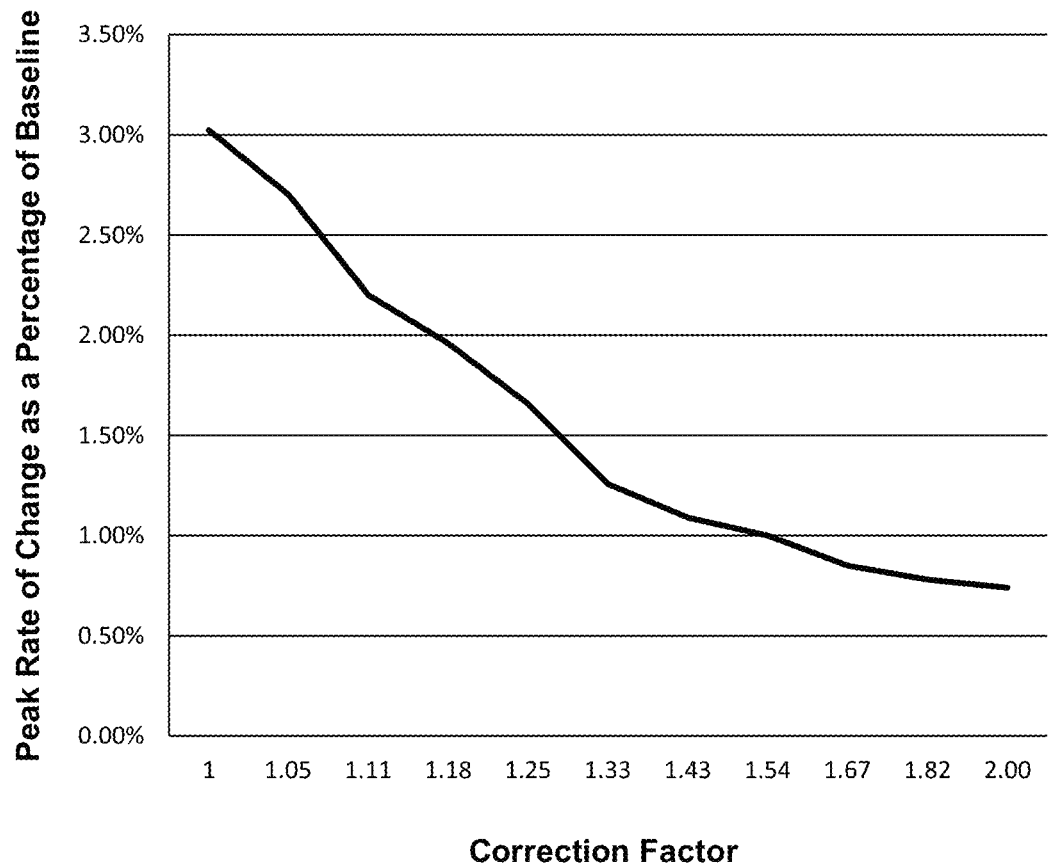
FIG. 15C illustrates a plot of the peak rate or change of sensor response as a percentage of baseline versus an associated correction factor for sensor sensitivity for the data of FIGS. 15A and 14B.

The peak rate of change values may be correlated with a correction factor as illustrated in the plot of FIG. 15C. From the plot of FIG. 15C, an associated lookup table or an associated algorithm/formula, the system may determine a correction factor for sensor sensitivity based upon the calculated peak rate of change.

Figure 16A:
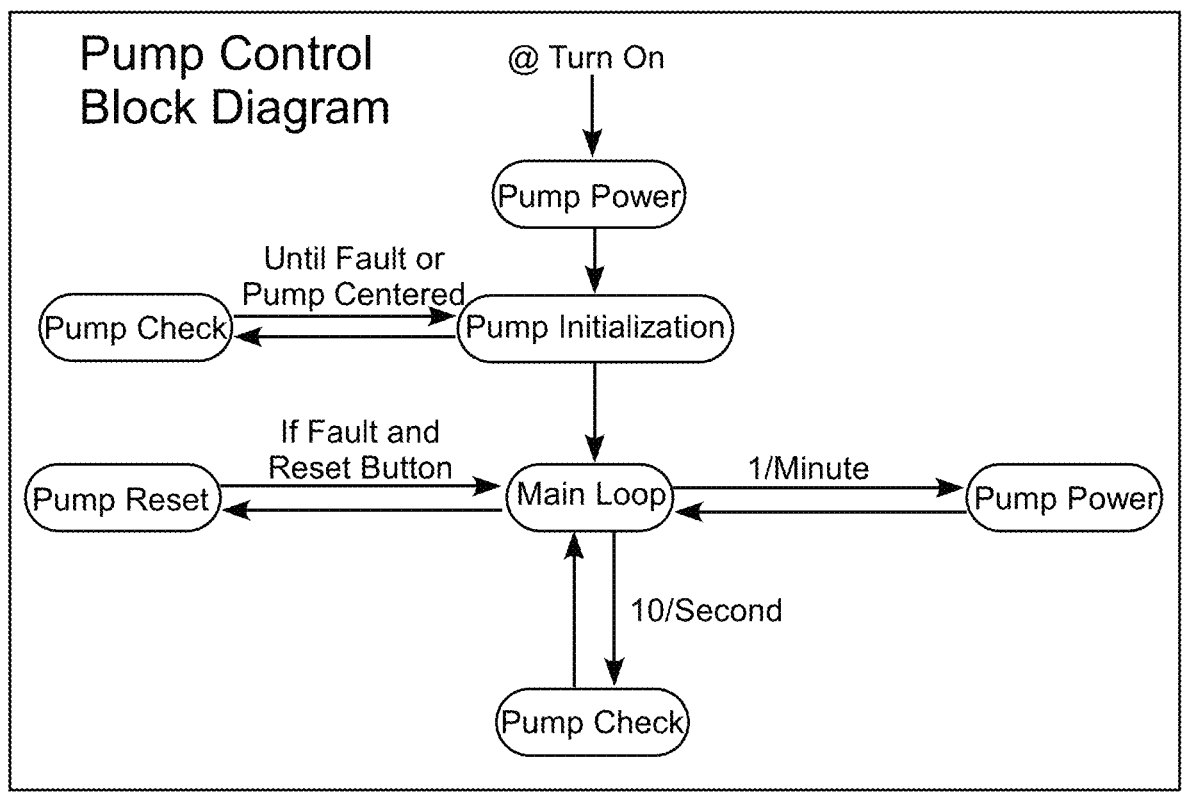
FIG. 16A illustrates a flow chart of an embodiment of a pump control process hereof.
Figure 16B:
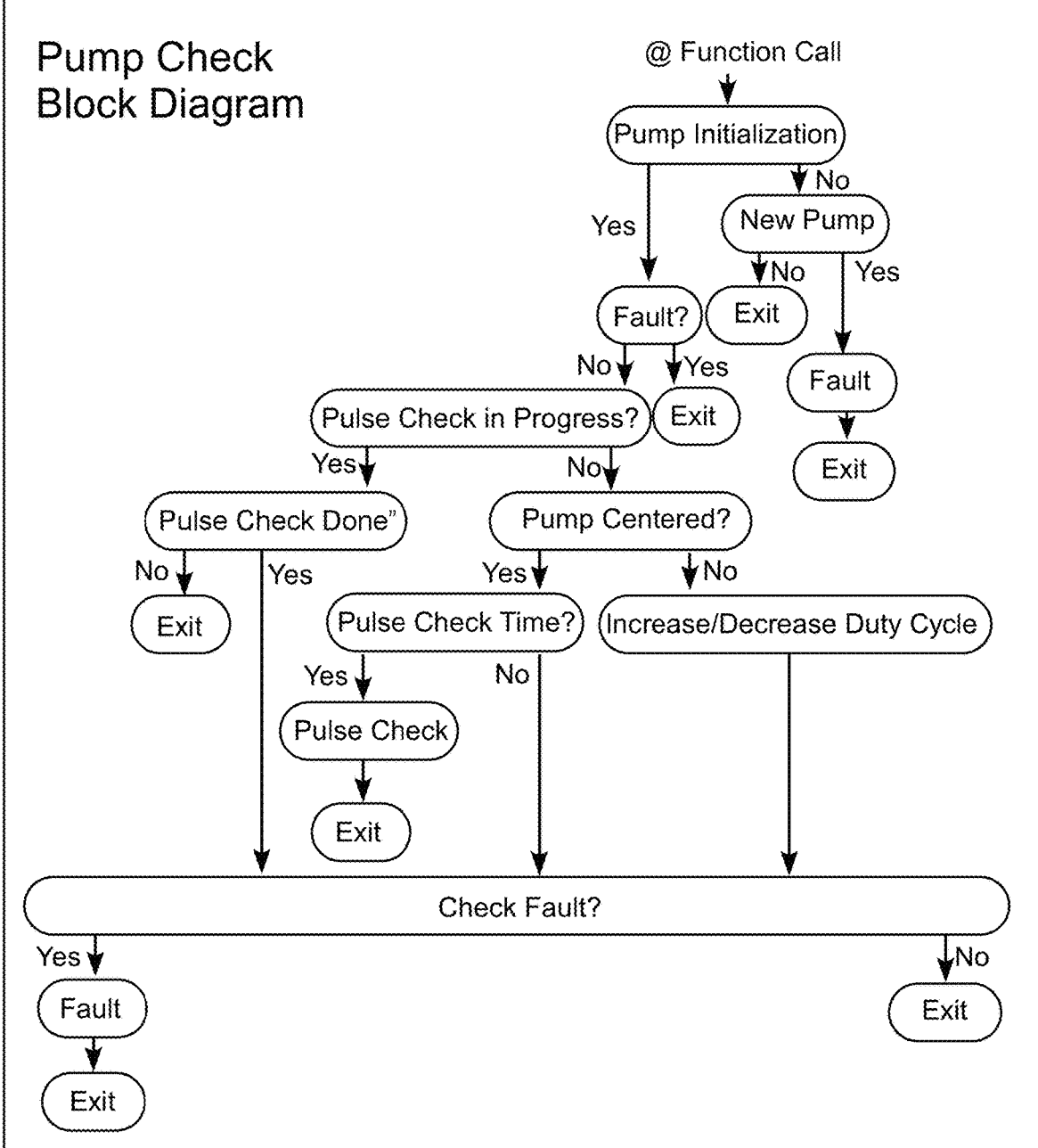
FIG. 16B illustrates an embodiment of a pump check process hereof.

An embodiment of a control procedure and fault detection procedure for a gas detection system or instrument that may be operated in a forced flow mode (that is, using a pneumatic pump to draw environmental gasses to the one or more sensors of the instrument as described in connection with FIG. 3I) is illustrated in FIGS. 16A and 16B. The control procedure and fault protection procedure may be used in connection with a system such as system 400 which may be operated in a forced flow mode as well as in a diffusion mode (that is, relying on diffusion to bring environmental gasses to the one or more sensors of the instrument as illustrated in FIG. 3J). The illustrated procedure is discussed in further detail in U.S. Pat. No. 6,092,992, the disclosure of which is incorporated herein by reference, and provides another independent check of instrument or system operational state. Computer code for the procedure may be stored in memory system 405 and is discussed in connection with the pseudocode set forth in the appendix to the specification of U.S. Pat. No. 6,092,992. Under the illustrated procedure, when the power switch of the gas detection instrument or system such as system 410 is turned on, a pump initialization procedure begins. A control system, which may, for example, include a processor system 404 (for example, including a microprocessor) in communicative connection with memory system 405) and/or control circuitry, preferably first checks to see if motor 406 of pump 406a is connected within the instrument or system 410 by measuring if a motor signal (for example, back emf) is being generated. If no motor signal is detected, the pump initialization procedure is exited and the gas detection instrument may be readily operated in a diffusion mode.

If motor 406 is detected, the duty cycle is set to 100% (percent on) for approximately 0.5 seconds. Microcontroller/processor 404 measures the power available from a power source such as a battery 408, and then sets the duty cycle to a maximum duty cycle previously established for the measured battery voltage. A maximum duty cycle and a minimum duty cycle for given battery voltage ranges may, for example, be established experimentally for a given pump and motor combination to provide an acceptable flow rate. For example, for the motor and pump combination controlled via the pseudocode set forth in U.S. Pat. No. 6,092,992, a maximum duty cycle of 80% and a minimum duty cycle of 5% were experimentally established to provide an acceptable flow rate for a battery voltage of greater than approximately 3.6 volts. For a battery voltage equal to or between approximately 3.6 and 3.3 volts, the maximum and minimum duty cycles were experimentally determined to be 90% and 5%, respectively. For a battery voltage less than approximately 3.3 volts, the maximum and minimum duty cycles were experimentally determined to be 100% and 5%, respectively.

In a number of embodiments, a PUMP CHECK procedure (see FIG. 16B) is initiated after the duty cycle is set to the maximum duty cycle for the measured battery voltage. The PUMP CHECK procedure first determines if a pump has been added to the gas detection instrument since the instrument has been turned on. If the pump is newly added, a fault is preferably indicated and the user is required to actuate a reset button to begin initialization of the newly added pump. Likewise, in a number of embodiments, removal of a pump results in a fault indication requiring the user to actuate the reset button to continue to operate the instrument in the diffusion mode.

The PUMP CHECK procedure is exited if a fault condition has been detected and a fault indication has been given. Upon initialization after turning on the instrument, however, fault indications are preferably delayed for up to 15 seconds for centering. If no fault condition has been detected, the PUMP CHECK procedure determines if a PULSE CHECK procedure is in progress. During initialization, however, the PULSE CHECK procedure is disabled for a period of, for example, 30 seconds in a number of embodiments. If no PULSE CHECK procedure is in progress, processor 404 may, for example, attempt to adjust the duty cycle in a manner to achieve a motor signal (average back emf voltage) centered between a maximum acceptable average voltage and a minimum acceptable average voltage experimentally determined to efficiently provide an acceptable flow rate. For example, for the pump and motor combination in the pseudocode of U.S. Pat. No. 6,092,992, the maximum and minimum motor signals were established to be approximately 1.95 and 1.85 volts, respectively. Processor 404 thus attempts to adjust the duty cycle to achieve a motor signal of approximately 1.90 volts. A motor signal in the range of approximately 1.85 to 1.95 volts may, for example, be considered to be centered, however. If pump motor 10 is not centered within, for example, 15 seconds, a pump fault is indicated by an electronic alarm system 90 such as an alarm light and/or an alarm sound.

If motor 10 is centered, the PUMP CHECK procedure checks whether it is time for a PULSE CHECK procedure. If yes, the PULSE CHECK procedure as described above is initiated. If no, processor 404 checks for faults. As discussed above, during operation of gas detection instrument or system 400 the average back emf or motor signal may, for example, be centered between 1.95 and 1.85 volts to maintain a suitable flow rate. Fault indications are enabled only when the motor signal is maintained in this range. If the duty cycle has been set to the minimum duty or the maximum duty for a defined period of time such as one second or more in controlling motor 406, a fault is indicated. Moreover, if the motor signal is less than approximately 1.4 volts for a defined period of time such as one second or more, a fault is indicated. Further, if the rate of change of the duty cycle is greater than 5% during, for example, a five second interval, a fault is indicated. Like the maximum and minimum duty cycles and the target motor signal range, the 1.4 volt minimum motor signal and 5%/5 second rate of change thresholds or fault conditions are readily determined experimentally for the pump and motor combination in use. If no fault condition is identified, the PUMP CHECK procedure is exited. After initialization, the PUMP CHECK procedure or function may, for example, be called or executed periodically (for example, 10 times per second).

Any time a fault condition is identified, the duty cycle may, for example, be set to its minimum duty cycle for the battery voltage. In a number of embodiments, the PUMP CONTROL procedure checks the battery voltage periodically (for example, once per minute) to set the appropriate maximum and minimum duty cycles.

In the embodiment of the PULSE CHECK procedure set forth in the pseudocode of U.S. Pat. No. 6,092,992, microcontroller 404 determines if the average voltage across motor 10 is less than 1.4 volts after a start-up period of approximately 1.5 seconds if the temperature is greater than or equal to 5° C. If the temperature is less than 5° C., the determination is made after a period of approximately 2 seconds. If the motor signal is less than 1.4 volts after the start-up period, a fault is indicated. The start-up voltage threshold of 1.4 volts may be determined experimentally for a particular pump and motor combination.

Pump and motor combinations may, for example, be tested over a range of load conditions, temperature conditions and battery voltages. Fault parameters or thresholds may, for example, be established by simulating various fault conditions. Various fault detection systems and methods may be used collectively or individually to detect pumping fault conditions in gas detection instruments. Blockage may, for example, be periodically simulated to test the continued operation of such systems and methods.

Figure 16C:
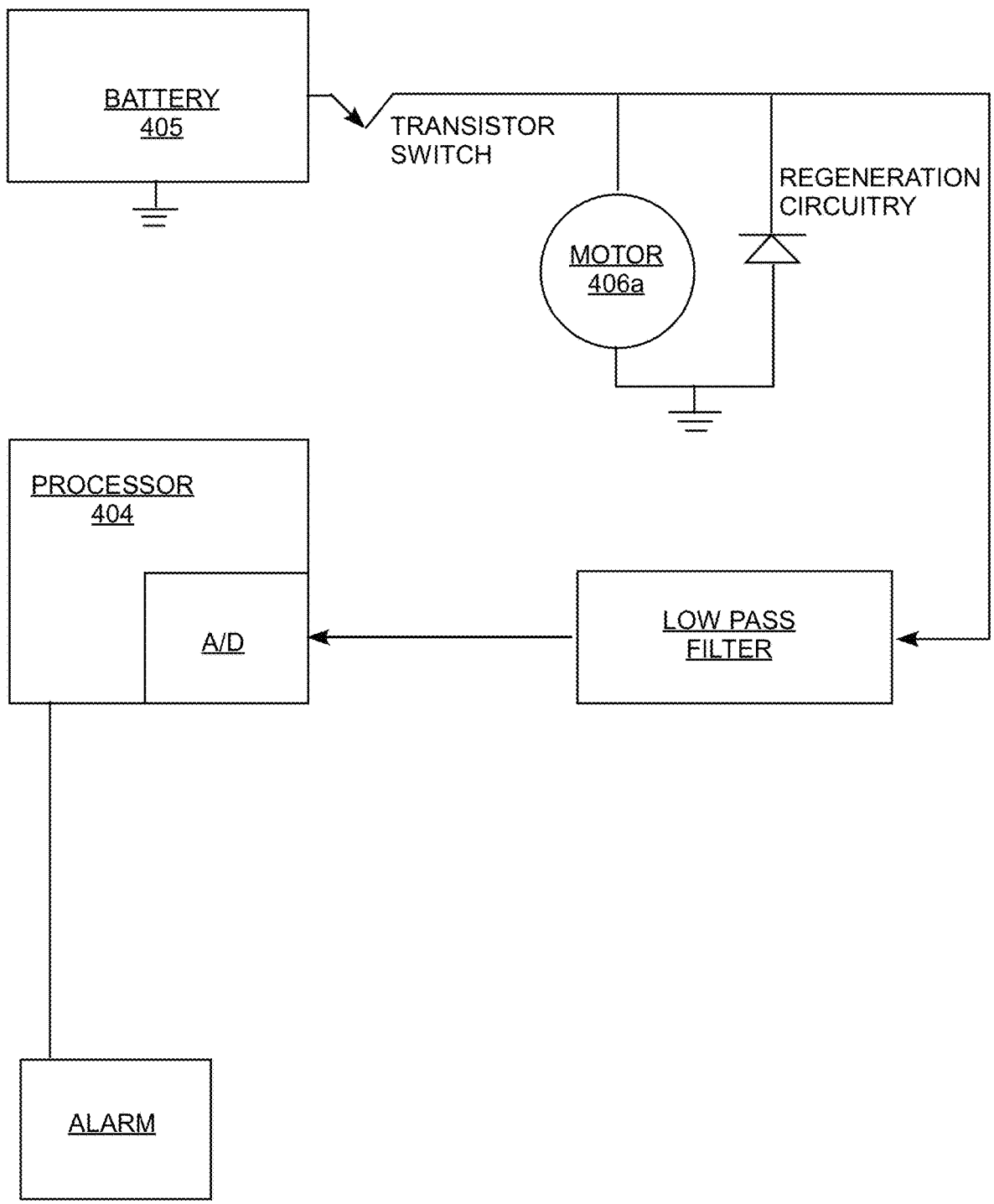
FIG. 16C is a schematic illustration of a control system for effecting the processes of FIGS. 16A and 16B.

FIG. 16C illustrates a system to effect control of pump 406 including motor 406a which drives pump 406 as described above. In the illustrated embodiment, motor 406a receives energy from a battery system 405 via a switch mechanism such as a transistor switch using Pulse Width Modulation (PWM). In PWM, the battery voltage is generally pulsed on and off hundreds of times per second. The time duration or duty cycle of each pulse is varied to control the speed of motor 406a. While the transistor switch is on, battery system 405 supplies power to motor 406a which energizes the windings of motor 406a and causes motor 406a to turn. While transistor switch is off, motor 406a continues to turn because of its momentum and acts like a generator to produce back electromotive force (emf). The energy (that is, the back emf) can be redirected back to motor 406a using a regeneration circuit including, for example, one or more diodes connected across motor 406a. This technique is known as regeneration. The back emf can also be used to provide feedback to control motor 406a.

A motor signal proportional to a voltage across the windings of motor 406a while the transistor switch is in the off state is measured and used to control motor 406a. There are a number of ways in which a motor signal proportional to the voltage across the windings during the off portion of the PWM cycle can be measured. For example, the approximate voltage at any defined instant during the off portion of each cycle can be measured. Further, the approximate average voltage developed across motor 406a during the off portion of the PWM cycle can be measured. In a number of embodiments, the approximate average voltage developed across motor 406a during both the off portion and the on portion of the PWM cycle is measured.

Each of the above measurements is proportional to the voltage contributed by the regeneration phase of the cycle. The voltage contributed by the regeneration phase is, in turn, proportional to the speed of motor 406*a*. Under light load conditions, motor 406*a* runs at a relatively high speed and generates a high voltage. When the load on motor 406*a* increases, motor 406*a* runs at a lower speed (assuming the energizing pulse has not changed) and the voltage decreases. In a number of embodiments, a microprocessor or microcontroller of processor system 404 measures the voltage decrease and then increases the pulse width (or duty cycle) proportionally to compensate for the load until the motor voltage is back to its normal operating value or within its normal operating range. When the load is removed, motor 406*a* will speed up momentarily and increase the voltage. Processor system 404 adjusts the duty cycle until the voltage is again back to its normal operating value or range.

By controlling the motor voltage, the speed of motor 406*a*, and thereby the flow rate of pump 406, are maintained in a relatively small operating range. Efficient motor control maximizes the life of battery system 405. The normal operating conditions of motor 406*a* under light and heavy loads are preferably characterized to determine the maximum and minimum duty cycle required for motor 406*a* over battery voltage changes and operating temperature changes normally experienced during use thereof. These maximum and minimum values may be used to determine normal operating limits for motor 406*a* and to detect problems in the flow system such as a sample line failure or a motor failure. A clogged sample line or a stalled motor condition, for example, is detected by a low average motor voltage. A burned out motor winding or an open commutator circuit is detected by the absence of the regenerated voltage.

A system and a method for detecting more marginal fault conditions, for example, caused by sudden changes in pneumatic loading may also be provided. Such sudden changes may occur, for example, when a liquid is inadvertently drawn into the free end of the sample line or when the sample line is restricted by a crushing force somewhere along its length. In one embodiment, the control system illustrated in FIG. 16C measures the rate of change in the value of the PWM required to maintain the average motor voltage constant. Once a predetermined center point or control point of average motor voltage is obtained, processor system 404 thereafter continuously adjusts the PWM to maintain the voltage constant and computes the rate of change in the PWM. The computed rate of change is continuously compared to an empirically determined normal, acceptable value of rate of change and any deviation in the computed rate greater than this acceptable rate is interpreted by processor system as a flow system failure or fault condition.

In another embodiment processor system 404 causes a momentary shutdown of the PWM supply signal on a periodic basis and subsequently verifies the generation of an acceptable average motor voltage within a set time interval after the resumption of the PWM supply signal. This procedure is referred to as a PULSE CHECK procedure in connection with FIG. 16A. The periodic shutdown may, for example, occur approximately every 15 seconds. This period is sufficiently frequent to monitor pump 406 and sample system performance, but not so frequent as to materially reduce the effective sample flow rate. The PWM shutdown period in this embodiment may, for example, be approximately 0.2 second. This shutdown period is sufficiently long to cause motor 406*a* to stall (that is, to slow or stop) and to allow the checking of the acceleration of motor 406*a* upon resumption of PWM within a predetermined interval of time. In a number of embodiments, the interval chosen for motor 406 to accelerate to a defined average voltage is approximately 1.5 seconds after the resumption of the PWM supply signal. While 1.5 seconds is an appropriate value around room temperatures, at lower temperatures more time may be allowed because of the slower acceleration of motor 406 arising from the "stiffness" of the mechanical components of pump 406 at such lower temperatures. Absent a marginal fault, motor 406*a* will restart successfully (that is, within the defined time interval after the resumption of the PWM motor 406*a* will again be regenerating an acceptable average voltage). A failure to "successfully" restart indicates a fault condition. For example, a marginal fault condition causing an excessive demand for motor torque upon restart is detected as a lower than normal average voltage at the end of the time interval and is interpreted by processor system 404 as a flow system failure. Testing the demand pump 406 for motor torque at a predetermined PWM provides a valuable check for a number of fault conditions.

The foregoing description and accompanying drawings set forth representative embodiments at the present time. Various modifications, additions and alternative designs will, of course, become apparent to those skilled in the art in light of the foregoing teachings without departing from the scope hereof, which is indicated by the following claims rather than by the foregoing description. All changes and variations that fall within the meaning and range of equivalency of the claims are to be embraced within their scope.

What is claimed is:

1. A system, comprising:
   a housing comprising an inlet,
   an electrolyte within the housing,
   a first amperometric electrochemical gas sensor comprising a first working electrode in contact with the electrolyte,
   a second amperometric electrochemical gas sensor comprising a second working electrode and a second counter electrode in contact with the electrolyte, and
   electronic circuitry comprising a control system configured to operate the first amperometric electrochemical in a sensing mode wherein the first amperometric electrochemical gas sensor is responsive to gas in fluid connection with the inlet and in an interrogation mode wherein the first amperometric electrochemical gas sensor is electronically interrogated to test the functionality of the first amperometric electrochemical gas sensor by applying an electric signal to the first amperometric electrochemical gas sensor to electronically simulate a gas response of the first amperometric electrochemical gas sensor by generating a current flow between the first working electrode of the first amperometric electrochemical gas sensor and a first counter electrode of the first amperometric electrochemical gas sensor via the electrolyte; the control system further being configured to operate the second amperometric electrochemical gas sensor in a sensing mode wherein the second amperometric electrochemical gas sensor is responsive to the gas in fluid connection with the inlet and in an interrogation mode wherein the second amperometric electrochemical gas sensor is electronically interrogated to test the functionality of the second amperometric electrochemical gas sensor by applying an electric signal to the second amperometric electrochemical gas sensor to electronically simulate a gas response of the second amperometric electrochemical gas sensor by generating a current flow between the second working electrode of the second amperometric electrochemical gas sensor and the second counter electrode of the second amperometric electrochemical gas sensor via the electrolyte; wherein the control system is further configured to place the first amperometric electrochemical gas sensor in the interrogation mode only if the second amperometric electrochemical gas sensor is in the sensing mode and placing the second amperometric electrochemical gas sensor in the interrogation mode only if the first amperometric electrochemical gas sensor is in the sensing mode.

2. The system of claim 1 wherein the electronic circuitry is further configured to measure a response of the first amperometric electrochemical gas sensor to the electronic simulation thereof and to measure the response of the second amperometric electrochemical gas sensor to the electronic simulation thereof.

3. The system of claim 1 wherein the first counter electrode and the second counter electrode are the same electrode.

4. The system of claim 1 further comprising a reference electrode in contact with the electrolyte and in operative connection with the first working electrode and the second working electrode.

5. A method of operating a gas detection device including a housing including an inlet, an electrolyte within the housing, a first amperometric electrochemical gas sensor including, a first working electrode in contact with the electrolyte, and a second amperometric electrochemical gas sensor including a second working electrode in contact with the electrolyte, comprising:

operating the first amperometric electrochemical in a sensing mode wherein the first amperometric electrochemical gas sensor is responsive to gas in fluid connection with the inlet and in an interrogation mode wherein the first amperometric electrochemical gas sensor is electronically interrogated to test the functionality of the first amperometric electrochemical gas sensor by applying an electric signal to the first amperometric electrochemical gas sensor to electronically simulate a gas response of the first amperometric electrochemical gas sensor by generating a current flow between the first working electrode of the first amperometric electrochemical gas sensor and a first counter electrode of the first amperometric electrochemical gas sensor via the electrolyte;

operating the second amperometric electrochemical gas sensor in a sensing mode wherein the second amperometric electrochemical gas sensor is responsive to the gas in fluid connection with the inlet and in an interrogation mode wherein the second amperometric electrochemical gas sensor is electronically interrogated to test the functionality of the second amperometric electrochemical gas sensor by applying an electric signal to the second amperometric electrochemical gas sensor to electronically simulate a gas response of the second amperometric electrochemical gas sensor by generating a current flow between the second working electrode of the second amperometric electrochemical gas sensor and a second counter electrode of the second amperometric electrochemical gas sensor via the electrolyte;

placing the first amperometric electrochemical gas sensor in the interrogation mode only if the second amperometric electrochemical gas sensor is in the sensing mode; and placing the second amperometric electrochemical gas sensor in the interrogation mode only if the first amperometric electrochemical gas sensor is in the sensing mode.

6. The method of claim 5 further comprising:

measuring a response of the first amperometric electrochemical gas sensor to the electronic simulation thereof; and measuring a response of the second amperometric electrochemical gas sensor to the electronic simulation thereof.

7. The method of claim 5 wherein the first counter electrode and the second counter electrode are the same electrode.

8. The method of claim 5 wherein the gas detection device further includes a reference electrode in contact with the electrolyte and in operative connection with the first working electrode and the second working electrode.

* * * * *

UNITED STATES PATENT AND TRADEMARK OFFICE
CERTIFICATE OF CORRECTION

PATENT NO. : 11,740,201 B2
APPLICATION NO. : 17/163710
DATED : August 29, 2023
INVENTOR(S) : Towner Bennett Scheffler, Michael Alvin Brown and Brian Keith Davis It is certified that error appears in the above-identified patent and that said Letters Patent is hereby corrected as shown below:

In the Claims
Column 46, Line 41, Claim 1 delete "electrochemical" and insert --electrochemical gas sensor--.
Column 47, Line 32, Claim 5 delete "electrochemical" and insert --electrochemical gas sensor--.

Signed and Sealed this
Third Day of September, 2024

Katherine Kelly Vidal
Director of the United States Patent and Trademark Office